US009696323B2

(12) United States Patent
Brasier et al.

(10) Patent No.: US 9,696,323 B2
(45) Date of Patent: Jul. 4, 2017

(54) BIOMARKERS FOR CHAGAS DISEASE RELATED CARDIOMYOPATHY

(71) Applicant: THE BOARD OF REGENTS OF THE UNIVERSITY OF TEXAS SYSTEM, Austin, TX (US)

(72) Inventors: Allan Brasier, Galveston, TX (US); John E. Wiktorowicz, League City, TX (US); Hyunsu Ju, League City, TX (US); Nisha Jain Garg, League City, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/850,113

(22) Filed: Sep. 10, 2015

(65) Prior Publication Data
US 2015/0377911 A1 Dec. 31, 2015

Related U.S. Application Data

(63) Continuation-in-part of application No. PCT/US2014/022510, filed on Mar. 10, 2014.

(60) Provisional application No. 61/775,676, filed on Mar. 10, 2013.

(51) Int. Cl.
*G01N 33/53* (2006.01)
*G01N 33/68* (2006.01)
*G01N 33/569* (2006.01)

(52) U.S. Cl.
CPC ... *G01N 33/6896* (2013.01); *G01N 33/56905* (2013.01); *G01N 2800/28* (2013.01)

(58) Field of Classification Search
None
See application file for complete search history.

(56) References Cited

U.S. PATENT DOCUMENTS

| 4,444,487 | A | 4/1984 | Miller et al. | 399/337 |
|---|---|---|---|---|
| 4,745,055 | A | 5/1988 | Schenk et al. | 435/7.6 |
| 6,535,624 | B1 | 3/2003 | Taylor | 382/128 |
| 2002/0091248 | A1 | 7/2002 | Adams et al. | 536/23.2 |
| 2011/0195425 | A1 | 8/2011 | Selinfreund et al. | 435/6.15 |
| 2012/0316211 | A1 | 12/2012 | Garg | 514/398 |

FOREIGN PATENT DOCUMENTS

| EP | 120694 | 10/1984 |
|---|---|---|
| EP | 125023 | 11/1984 |
| EP | 256654 | 2/1988 |
| WO | WO 88/03565 | 5/1988 |
| WO | WO 2011/127219 | 10/2011 |

OTHER PUBLICATIONS

Doulias et al. (Science Signalling 2013 vol. 6, total 54 pages).*
Bizzozero et al. (J. Neurosci Res 2009 vol. 87, p. 2881-2889).*
Almeida et al. "Subcellular Proteomics and Global Analysis of Posttranslational Modifications to Study Functional Roles of Trypanosoma cruzi Molecules" *The Open Parasitology Journal*, 4: 167-177, 2010.
Ba et al., "Trypanosoma cruzi induces the reactive oxygen species-PARP-1-RelA pathway for up-regulation of cytokine expression in cardiomyocytes", *J Biol Chem*, 285, 11596-606, (2010).
Bern and Montgomery, "An estimate of the burden of Chagas disease in the United States", *Clin Infect Dis* 49, e52-54, (2009).
Brasier et al., "Predicting intermediate phenotypes in asthma using bronchoalveolar lavage-derived cytokines", *Clin Transl Sci*, 3:147-57, (2010).
Carter and Church, "Obesity and breast cancer: the roles of peroxisome proliferator-activated receptor-$\gamma$ and plasminogen activator inhibitor-1", *PPAR Res*, 2009, 345320, (2009).
CDC., "Chagas disease after organ transplantation—Los Angeles, California, 2006", *MMWR Morb Mortal Wkly Rep* 55, 798-800, (2006).
CDC. "Blood donor screening for chagas disease—United States, 2006-2007", *MMWR Morb Mortal Wkly Rep* 56, 141-143, (2007).
Cunha-Neto et al., "Cardiac gene expression profiling provides evidence for cytokinopathy as a molecular mechanism in Chagas' disease cardiomyopathy", *Am J Pathol*, 167, 305-13, (2005).
de Oliveira et al., "Oxidative stress in chronic cardiopathy associated with Chagas disease", *Int J Cardiol*, 116: 357-63, (2007).
Dhiman et al., "Enhanced nitrosative stress during Trypanosoma cruzi infection causes nitrotyrosine modification of host proteins: implications in Chagas' disease", *Am J Pathol*, 173: 728-740, (2008).
Dhiman et al., "Increased myeloperoxidase activity and protein nitration are indicators of inflammation in patients with Chagas' disease", *Clinical and Vaccine Immunology*, 16: 660-666, (2009).
Diez et al., "The use of network analyses for elucidating mechanisms in cardiovascular disease", *Mol Biosyst*, 6: 289-304, (2010).
Dowsey et al., "Informatics and statistics for analyzing 2-d gel electrophoresis images", *Methods Mol Biol*, 604: 239-55, (2010).
Fae et al., "PDIA3, HSPA5 and vimentin, proteins identified by 2-DE in the valvular tissue, are the target antigens of peripheral and heart infiltrating T cells from chronic rheumatic heart disease patients", *J Autoimmun*, 31: 136-41, (2008).
Falkner et al., "Expression of mouse immunoglobulin genes in monkey cells", *Nature*, 298:286, 1982.
Fawcett, "An introduction to ROC analysis", *Pattern Recognition Letters*, 27: 861-74, (2006).
Flavigny et al., "Identification of two novel mutations in the ventricular regulatory myosin light chain gene (MYL2) associated with familial and classical forms of hypertrophic cardiomyopathy", *J Mol Med*, 76: 208-14, (1998).
Friedman and Roosen, "An introduction to multivariate adaptive regression splines", *Stat Methods Med Res*, 4: 197-217, (1995).
George and McCulloch, "Variable Selection Via Gibbs Sampling", *J. American Statistical Association*, 88: 881-89, (1993).
Goldenberg et al., "Transcriptomic alterations in Trypanosoma cruzi-infected cardiac myocytes", *Microbes Infect*, 11: 1140-49, (2009).
Gupta et al., "Trypanosoma cruzi infection disturbs mitochondrial membrane potential and ROS production rate in cardiomyocytes", *Free Radic Biol Med*, 47: 1414-21, (2009).
Gupta et al., "Oxidative Stress in Chagas Disease", *Interdiscip Perspect Infect Dis*, 2009: 190354, (2009).
Hanley and McNeil, "The meaning and use of the area under a receiver operating characteristic (ROC) curve", *Radiology*, 143: 29-36, (1982).
International Search Report and Written Opinion issued in PCT/US2014/022510, mailed on Sep. 9, 2014.

(Continued)

*Primary Examiner* — Jacob Cheu
(74) *Attorney, Agent, or Firm* — Norton Rose Fulbright US LLP

(57) ABSTRACT

Certain embodiments include methods for assessing a subject having a trypanosome infection for the presence or absence of indications of cardiomyopathy.

5 Claims, 16 Drawing Sheets

(56) References Cited

OTHER PUBLICATIONS

Jamaluddin et al., "Role of peroxiredoxin 1 and peroxiredoxin 4 in protection of respiratory syncytial virus-induced cysteinyl oxidation of nuclear cytoskeletal proteins", *J Virol*, 84: 9533-45, (2010).
Junqueira et al., "The endless race between Trypanosoma cruzi and host immunity: lessons for and beyond Chagas disease", *Expert Rev Mol Med*, 12: e29, (2010).
Kabaeva et al., "Systematic analysis of the regulatory and essential myosin light chain genes: genetic variants and mutations in hypertrophic cardiomyopathy", *Eur J Hum Genet*, 10: 741-48, (2002).
Katsumoto et al., "The role of the vimentin intermediate filaments in rat 3Y1 cells elucidated by immunoelectron microscopy and computer-graphic reconstruction", *Biol Cell*, 68: 139-46, (1990).
Koya et al., "Gelsolin Inhibits Apoptosis by Blocking Mitochondrial Membrane Potential Loss and Cytochrome c Release*", *J Biol Chem*, 275: 15343-49, (2000).
Leon and Engman, "Autoimmunity in Chagas heart disease", *Int J Parasitol*, 31: 555-61, (2001).
Leon et al., "A cardiac myosin-specific autoimmune response is induced by immunization with Trypanosoma cruzi proteins", *Infect Immun*, 72: 3410-17, (2004).
Machado et al., "Pathogenesis of Chagas disease: time to move on", *Front Biosci (Elite Ed)*, 4: 1743-58, (2012).
Miseta and Csutora, "Relationship between the occurrence of cysteine in proteins and the complexity of organisms", *Mol Biol Evol*, 17: 1232-39, (2000).
Morrison et al., "Transfer and Expression of Immunoglobulin Genes", *Ann Rev. Immunol*, 2:239, 1984.
Morrison, "Sequentially Derived Mutants of the Constant Region of the Heavy Chain of Murine Immunoglobulins", *J. Immunol.*, 123:793, 1979.
Oikonomou et al., "Gelsolin expression is necessary for the development of modelled pulmonary inflammation and fibrosis", *Thorax*, 64: 467-75, (2009).
Organization, W. H. "Chagas disease: control and elimination", In *Report of the secretariat. WHO, Geneva*, UNDP/World Bank/WHO, (2010).
Patel et al., "Activity and subcellular compartmentalization of peroxisome proliferator-activated receptor alpha are altered by the centrosome-associated protein CAP350", *J Cell Sci*, 118: 175-86, (2005).
Poetter et al., "Mutations in either the essential or regulatory light chains of myosin are associated with a rare myopathy in human heart and skeletal muscle", *Nat Genet*, 13: 63-69, (1996).
Pretzer and Wiktorowicz, "Saturation fluorescence labeling of proteins for proteomic analyses", *Anal Biochem*, 374: 250-262, (2008).
Qi et al., "Peroxisome Proliferator-Activated Receptors Coactivators, and Downstream Targets", *Cell Biochem Biophys*, 32 Spring, 187-204, (2000).
Rakhshandehroo et al., "Peroxisome proliferator-activated receptor alpha target genes", *PPAR Res*, 2010, (2010).
Richard et al., "Hypertrophic cardiomyopathy: distribution of disease genes, spectrum of mutations, and implications for a molecular diagnosis strategy", *Circulation*, 107: 2227-32, (2003).
Silacci et al., "Gelsolin superfamily proteins: key regulators of cellular functions", *Cell Mol Life Sci*, 61: 2614-23, (2004).
Souza et al., "The benefits of using selenium in the treatment of Chagas disease: prevention of right ventricle chamber dilatation and reversion of Trypanosoma cruzi-induced acute and chronic cardiomyopathy in mice", *Mem Inst Oswaldo Cruz*, 105: 746-751, (2010).
Szatmari et al., "PPARgamma regulates the function of human dendritic cells primarily by altering lipid metabolism", *Blood*, 110: 3271-80, (2007).
Tanowitz et al., "Perspectives on Trypanosoma cruzi-induced heart disease (Chagas disease).", *Prog Cardiovasc Dis*, 51: 524-539, (2009).
Teixeira et al., "Proteomic inventory of myocardial proteins from patients with chronic Chagas' cardiomyopathy", *Braz J Med Biol Res*, 39: 1549-62, (2006).
Thomas and Bonchev, "A survey of current software for network analysis in molecular biology", *Hum Genomics*, 4: 353-360, (2010).
Ward et al., "Binding Activities of a repertoire of single immunoglobulin variable domains secreted from *Escherichia coli*", *Nature*, 341:544-546, 1989.
Wen and Garg, "Mitochondrial generation of reactive oxygen species is enhanced at the $Q_0$ site of the complex III in the myocardium of *Trypanosoma cruzi*-infected mice: beneficial effects of an antioxidant", *J Bioenerg Biomembr*, 40, 587-598, (2008).
Wen and Garg, "Proteome expression and carbonylation changes during Trypanosoma cruzi infection and Chagas disease in rats", *Mol Cell Proteomics* 11, M111.010918. Epub 012011, (2012).
Wen et al., "Phenyl-alpha-tert-butyl nitrone reverses mitochondrial decay in acute Chagas' disease", *Am J Pathol*, 169: 1953-1964, (2006).
Wen et al., "Increased oxidative stress is correlated with mitochondrial dysfunction in chagasic patients", *Free Rad Biol Med*, 41, 270-76, (2006).
Wen et al., "Tissue-specific oxidative imbalance and mitochondrial dysfunction during Trypanosoma cruzi infection in mice", *Microbes Infect*, 10: 1201-09, (2008).
Wen et al., "Phenyl-alpha-tert-butyl-nitrone and benzonidazole treatment controlled the mitochondrial oxidative stress and evolution of cardiomyopathy in chronic chagasic Rats", *J Am Coll Cardiol*, 55: 2499-2508, (2010).
Wen et al., "Serum proteomic signature of human chagasic patients for the identification of novel potential protein biomarkers of disease", *Mol Cell Proteomics* 11: 435-52, (2012).
Wiktorowicz et al., "Quantification of cysteinyl S-nitrosylation by fluorescence in unbiased proteomic studies", *Biochemistry* 50: 5601-5614, (2011).
Yan et al., "A complex of two centrosomal proteins, CAP350 and FOP, cooperates with EB1 in microtubule anchoring", *Mol Biol Cell*, 17: 634-44, (2006).
Yang et al., "Decreased SLIM1 expression and increased gelsolin expression in failing human hearts measured by high-density oligonucleotide arrays", *Circulation*, 102: 3046-52, (2000).
Zacks et al., "An overview of chagasic cardiomyopathy: pathogenic importance of oxidative stress", *An Acad Bras Cienc*, 77 : 695-715, (2005).
Zhang and Chait, "ProFound: An Expert System for Protein Identification Using Mass Spectrometric Peptide Mapping Information", *Anal Chem*, 72: 2482-89, (2000).

\* cited by examiner

BIOMARKERS FOR CHAGAS DISEASE RELATED CARDIOMYOPATHY

STATEMENT REGARDING PRIORITY

This Application claims priority to and is a continuation-in-part of International Application PCT/US2014/022510 filed Mar. 10, 2014, and U.S. Provisional Patent Application No. 61/775,676 filed Mar. 10, 2013, each of which is incorporated herein by reference in its entirety.

STATEMENT REGARDING FEDERALLY FUNDED RESEARCH

This invention was made with government support under HHSN272200800048C and HL094802 awarded by the National Institutes of Health. The United States government has certain rights in the invention.

BACKGROUND

Chagas disease, transmitted by injection of *Trypanosoma cruzi* through the bite of an insect vector, is designated as the most important emerging disease in developed countries, with approximately 16-18 million cases of infection in Latin America with 120 million people (~25% of the population) more at risk of infection (Organization, W. H. (2010) Chagas disease: control and elimination, In *Report of the secretariat. WHO, Geneva*, UNDP/World Bank/WHO). In 30-40% of the infected individuals, the disease may progress to irreversible cardiomyopathy after many years, with infected individuals serving as carriers of the organism and exhibiting considerable morbidity and high risk of mortality (Machado et al. (2012) *Front Biosci (Elite Ed)* 4, 1743-58). Unfortunately, there are no vaccines or safe drugs—benznidazole and nifurtimox can be used for treatment of acute infection, but have high toxicity in adults and are ineffective in arresting or reversing the progression of the disease—and as a consequence, the NIH and CDC have recognized Chagas disease as a neglected emergency (Bern and Montgomery, (2009) *Clin Infect Dis* 49, e52-54; CDC. (2006) Chagas disease after organ transplantation—Los Angeles, Calif., 2006, *MMWR Morb Mortal Wkly Rep* 55, 798-800; CDC. (2007) Blood donor screening for chagas disease—United States, 2006-2007, *MMWR Morb Mortal Wkly Rep* 56, 141-143).

Thus, there remains a need for additional compositions and methods for identifying subjects harboring Trypanosomes and particularly those subjects at risk of developing cardiomyopathy.

SUMMARY

Blood serves as a useful tissue capable of detecting and responding to the changes induced in the body during the course of *T. cruzi* infection and disease development. The changes in immune response, oxidative stress, and antioxidant imbalance are detectable in peripheral blood of infected mice (Wen et al., (2008) *Microbes Infect*, 10, 1201-09), and, notably, a strong positive correlation was detected for the disease state-specific changes in the heart-versus-blood level of oxidative stress markers and antioxidants (e.g. glutathione peroxidase, glutathione, manganese superoxide dismutase) (Wen et al., (2008) *Microbes Infect*, 10, 1201-09). Distinct plasma protein-nitrosylation profiles have also been documented in acutely- and chronically-infected chagasic animals (Dhiman et al., (2008) *Am J Pathol*, 173, 728-740). Studies described herein along with documentation of oxidative overload in chagasic humans (Wen et al., (2006) *Free Rad Biol Med*, 41, 270-76; de Oliveira et al., (2007) *Int J Cardiol*, 116, 357-63), support the idea that characterization of plasma proteomes will be useful in identifying the molecular mechanisms that are disturbed during the progression of Chagas disease.

Certain embodiments include assessing the status of a subject by measuring and evaluating the protein levels and/or the levels of protein modification of 1, 2, 3, 4, 5, 6, 7, 8, 9, 10, 11, 12, 13, 14, 15, 16, 17, 18, 19, 20, or more proteins selected from vinculin (SEQ ID NO:1), serum albumin (SEQ ID NO:2), integrin alpha-IIb isoform 3 (SEQ ID NO:3), myeloperoxidase isoform H7 (SEQ ID NO:4), actin (cytoplasmic 2, N-terminal processed) (SEQ ID NO:5), Talin 1 (SEQ ID NO:6), actin (cytoplasmic 1, N-terminal processed) (SEQ ID NO:7), actin (cytoplasmic 1, N-terminal processed) (SEQ ID NO:8), unconventional myosin-IXa (SEQ ID NO:9), peptidyl-prolyl cis-trans isomerase A (SEQ ID NO:10), WD repeat-containing protein 49 (SEQ ID NO:11), Keratin type II cytoskeletal 1 (SEQ ID NO:12), parathyroid hormone 2 receptor (fragment) (SEQ ID NO:13), proteasome subunit beta type-2 (SEQ ID NO:14), ferritin light chain (SEQ ID NO:15), annexin (SEQ ID NO:16), actin (cytoplasmic 1, N-terminal processed) (SEQ ID NO:16), keratin type I cytoskeletal 10 (SEQ ID NO:18), heterogeneous nuclear ribonucleoprotein A1 (Fragment) (SEQ ID NO:19), SH3 domain-binding glutamic acid-rich-like protein 3 (SEQ ID NO:20), Ras-related protein Rap-1b (SEQ ID NO:21), actin (cytoplasmic 1, N-terminal processed) (SEQ ID NO:22), POTE ankyrin domain family member F (SEQ ID NO:23), vimentin (SEQ ID NO:24), protein S100-A11 (SEQ ID NO:25), Isoform 2 of fibrinogen alpha chain (SEQ ID NO:26), tubulin beta chain (SEQ ID NO:27), Myosin regulatory light chain 12B (SEQ ID NO:28), Annexin A3 (SEQ ID NO:29), keratin type I cytoskeletal 10 (SEQ ID NO:30), Actin cytoplasmic 2 N-terminally processed (Fragment) (SEQ ID NO:31), ATP synthase subunit alpha (SEQ ID NO:32) (see table III). The methods further comprising computer implementation of such a method. In certain aspects the subject is diagnosed or at risk of trypanosome infection. In further aspects the subject has a trypanosome infection and is assessed for the presence or absence of indications of cardiomyopathy.

Certain embodiments include methods of assessing a subject having Chagas disease comprising: measuring levels of (i) one or more proteins selected from vimentin, gamma actin, or keratin 10, or (ii) level of cysteinyl-S-nitrosylation (SNO) of one or more of beta actin, annexin A6, ferritin light chain fragment (~0.18 kDa), parathyroid hormone 2 receptor fragment (~20 kDa), or myosin-IXa fragment; wherein elevated levels of the proteins and/or nitrosylation is indicative of risk for developing chagasic cardiomyopathy. Certain protein levels will increase and certain protein levels will decrease as compared to control. SNO modification will either increase or decrease relative to a control. The levels of the markers have been associated with a particular disease state. As SNO modification increases the fluorescence from the modified protein decreases. Likewise, as SNO modification decreases the fluorescence of the lesser-modified protein increases. In certain aspects a SNO modification is associated with cardiomyopathy as is indicated by a negative ratio in the CCM+ group and a positive ratio in the CCM− group. In a further aspect a SNO modification is associated with a non-cardiomyopathic condition in which the CCM− ratio is negative and the CCM+ ratio is positive. Furthermore, an increased or decreased level of a protein can be associated with CCM+ as is indicated by a positive or negative abundance ratio, respectively.

In certain aspects the level of vimentin is measured. In a further aspect the level of gamma actin is measured. In certain aspects the level of keratin 10 is measured. In certain aspects the levels of vimentin and gamma actin are measured. In certain aspects the level of vimentin and keratin 10 are measured. In certain aspects the level of gamma actin and keratin 10 are measured. In certain aspects the level of vimentin, gamma actin, and keratin 10 are measured. In certain aspects protein levels are determined by western blot analysis, mass spectrometry, or image analysis of two-dimensional gels.

In certain aspects the level of modification of ferritin light chain fragment is measured. In certain aspects the level of modification of annexin A6 is measured. In certain aspects the level of modification of myosin-IXa fragment is measured. In certain aspects the level of modification of ferritin light chain fragment and annexin A6 is measured. In certain aspects the level of modification of ferritin light chain fragment and myosin-IXa fragment is measured. In certain aspects the level of modification of annexin A6 and myosin-IXa fragment is measured. In certain aspects the level of modification of ferritin light chain fragment, annexin A6, and myosin-IXa fragment is measured. In certain aspects the modification level of parathyroid hormone receptor and/or β actin are measured. In certain aspects the level of protein modification is measured by saturation fluorescence labeling.

In certain aspects the protein level and/or SNO modification of 1, 2, 3, 4, 5, 6, 7, 8, 9, 10, 11, 12, 13, 14, 15, 16, 17, 18, 19, 20, 21, 2, 23, 24, or 25 of the proteins described Table III are measured.

Certain aspects include a computer-implemented method for assessing a subject for trypanosome infection or cardiomyopathy. In certain aspects a computer implemented method comprises the steps of (a) obtaining protein level measurements of one or more of vimentin, gamma actin, or keratin 10, and/or protein modification measurements of one or more of beta actin, annexin A6, ferritin light chain fragment (~18 kDa), parathyroid hormone 2 receptor fragment (~20 kDa), or myosin-IXa fragment, (b) transforming the obtained measurements to a score or ratio, and (c) determining if the measurements indicate the presence of trypanosome infection or the risk of developing or the presence or absence of cardiomyopathy.

Certain aspects include methods of treating a patient at risk of or having initial indication of chagasic cardiomyopathy comprising: administering a treatment for cardiomyopathy to a patient having elevated levels of (i) one or more proteins selected from vimentin, gamma actin, or keratin 10, or (ii); level of cysteinyl-S-nitrosylation (SNO) of one or more of beta actin, annexin A6, ferritin light chain fragment (~18 kDa), parathyroid hormone 2 receptor fragment (~20 kDa), or myosin-IXa fragment.

The treatment of cardiomyopathy includes administration of vasodilators (e.g., prazosin, hydralazine and the like), angiotensin conversion enzyme inhibitors (e.g., captopril and the like) and the like for symptomatic therapy of dilated cardiomyopathy; and administration of β blockers (e.g., propranolol and the like) and Ca antagonists (e.g., verapamil, diltiazem and the like) to treat hypertrophic cardiomyopathy.

Certain embodiments include detecting evidence of chagasic cardiomyopathy in a biological sample, comprising the step of measuring the level or presence of at least one protein selected from the group consisting of gelsolin (GSN), myosin light chain 2 (MYL2), vimentin (VIM), myosin heavy chain 11 (MYH11), vinculin (VCL), and plasminogen (PLG) in the sample. In an undiagnosed subject, the levels of one or more of the proteins can be indicative of T. cruzi infection. In a subject already diagnosed with T. cruzi infection, the protein levels can be indicative of the severity of disease, e.g., the risk of developing, or the stage of chagasic cardiomyopathy in the subject. Elevated levels of gelsolin (GSN), myosin light chain 2 (MYL2), vimentin (VIM), myosin heavy chain 11 (MYH11), vinculin (VCL), and/or plasminogen (PLG) biomarkers in the samples is indicative of T. cruzi infection, Chagas disease, and/or chagasic cardiomyopathy in the subject. The content of U.S. application Ser. No. 13/470,209 filed May 11, 2012 entitled "Diagnostic Methods for Assessing Risk of Chagas Disease and Heart Failure" is incorporated herein by reference in its entirety.

Certain aspects may include assessment of a subject for risk of developing chagasic cardiomyopathy. Levels of biomarkers are measured and these measurements indicate whether a subject is at risk of developing cardiomyopathy. Certain aspects include measuring the levels of VIM, GSN, MYL2, MYH11, VCL, and PLG. In a further aspect, levels of VIM are measured in combination with one or more of GSN, MYL2, MYH11, VCL, or PLG. In a further aspect, levels of GSN are measured in combination with one or more of VIM, MYL2, MYH11, VCL, or PLG. In still a further aspect, levels of MYL2 are measured in combination with one or more of VIM, GSN, MYH11, VCL, or PLG. Certain aspects include measuring levels of MYH11 in combination with one or more of VIM, GSN, MYL2, VCL, or PLG. In further aspects, levels of VCL are measured in combination with one or more of VIM, GSN, MYL2, MYH11, or PLG. In still a further aspect, levels of PLG are measured in combination with one or more of VIM, GSN, MYL2, MYH11, or VCL.

In certain aspects, the methods include treating a subject identified as (a) having T. cruzi infection, (b) at risk of developing chagasic cardiomyopathy, or (c) diagnosed with chagasic cardiomyopathy. Treatments can include anti-trypanosome treatments, or preventive or therapeutic treatments for cardiomyopathy, or a combination of both.

Certain aspects include methods for screening blood comprising measuring the levels of one or more of VIM, GSN, MYL2, MYH11, VCL, and PLG proteins. An increased level of one or more of these proteins is indicative of Trypanosome contamination. In certain aspects blood is screened prior to or during banking. In a further aspect, the methods can further comprise conducting confirmatory testing if the levels of one or more of the biomarkers are elevated.

Certain embodiments are directed to serodiagnostic kits for determining whether a subject is infected with Trypanosoma cruzi and/or staging the severity of Chagas disease, said kit comprising: (a) an antibody directed against VIM, GSN, MYL2, MYH11, VCL, and/or PLG, wherein said antibody is linked to a reporter molecule; (b) a buffer; and c) a reagent for detection of the reporter molecule.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The term "antigen" as used herein is defined as a compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. Epitopes can be formed both from contiguous amino acids or noncontiguous amino acids juxtaposed by tertiary folding of a protein.

The term "antibody" as used herein includes immunoglobulin molecules and immunologically active portions of immunoglobulin molecules, i.e., molecules that contain an antigen binding site that specifically binds (immunoreacts with) an antigen. A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., Nature 341:544-546, 1989); and (vi) a F(ab')$_2$ fragment. Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Falkner et al., Nature 298:286, 1982; Morrison, J. Immunol. 123:793, 1979; Morrison et al., Ann Rev. Immunol 2:239, 1984).

The term "animal" as used herein refers to living multicellular vertebrate organisms, a category that includes, for example, mammals and birds. The term mammal includes both human and non-human mammals. Similarly, the term "subject" includes both human and veterinary subjects. The term mammal includes dogs, cats, cattle, horses, goats, sheep, and other domesticated mammals, as well as non-domesticated mammals. In particular embodiments, the animal is a triatome (the insect vector of *T. cruzi*) host, e.g., a human, opossum, raccoon, armadillo, squirrel, rat, or mouse.

The term "diagnostic" refers to identifying the presence or nature of a pathologic condition. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis.

"Prognosis" is a probability that a pathologic condition will develop (e.g., result in additional sequelae) or progress (e.g., increase in severity).

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
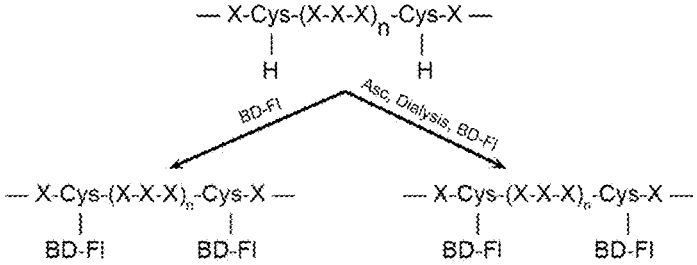
FIG. 1. Saturation fluorescence labeling with uncharged cysteine-specific BODIPY-FL-maleimide (BD) dye. Three cases are presented focusing on the degree of cysteine modification reversible by Asc (i.e., SNO). All assume that the protein abundance does not change with the treatment. Case A demonstrates a canonical protein structure with no SNO before treatment with BD, after labeling, and after Asc-treatment and labeling. No change in protein spot fluorescence will be observed unless the protein abundance changes. This is quantified by the ratios of ratios as described in the Methods. Case B demonstrates the partial SNO after treatment and the resultant ratio of ratios upon Asc-treatment and labeling. Here ratios less than 1 are expressed as the negative reciprocal. Case C demonstrates the complete SNO and the ratio of ratios after Asc-reversal. If the protein abundance changes due to the cardiomyopathy, with or without SNO, the ratio of ratios will normalize the values. Taken from ref [Wiktorowicz et al., (2011) *Biochemistry* 50, 5601-5614.].

In 30-40% of trypanosome infected individuals disease may progress to irreversible cardiomyopathy after many years with infected individuals serving as carriers of the organism and exhibiting considerable morbidity and high risk of mortality (Machado et al., (2012) *Front Biosci* (*Elite Ed*) 4, 1743-58). Unfortunately, there are no vaccines or safe drugs—benznidazole and nifurtimox can be used for treatment of acute infection, but have high toxicity in adults and are ineffective in arresting or reversing the progression of the disease. Accordingly, it is crucial that biomarkers and molecular pathways are identified that could classify the disease state, detect asymptomatic individuals who are at risk of developing chagasic cardiomyopathy, identify new therapies to arrest or prevent the progression of symptomatic clinical disease, and develop tools, methods and kits to assess the efficacy of new therapies.

Distinct cardiac and plasma proteins have been identified as being oxidized/nitrated in acute and chronic chagasic animals and humans (Dhiman et al., (2008) *Am J Pathol* 173, 728-40; Wen and Garg, (2012) *Mol Cell Proteomics* 11, M111.010918. Epub 012011; Wen et al., (2012) *Mol Cell Proteomics* 11, 435-52), and there is a direct correlation between cardiac and peripheral blood level of protein oxidation in chagasic mice (Wen et al., (2008) *Microbes Infect* 10, 1201-09). These observations suggest that pathological processes leading to the development of chagasic cardiomyopathy in patients cause characteristic changes in the concentration/oxidation of proteins in the blood and generate a detectable disease-specific molecular phenotype. The inventors have identified combinations of proteins and oxidatively modified proteins (cysteinyl-S-nitrosylated, SNO) that can be used to assess the risk of developing irreversible cardiomyopathy. Certain embodiments include one or more of:

Identifying and/or using a set of proteins whose concentration and/or SNO modifications can be measured in a patient with or without diagnosed Chagas disease to indicate the presence of trypanosome infection and/or cardiomyopathy. The predictive proteins can include, but are not limited to vimentin, gamma actin, and keratin 10. The predictive SNO proteins include, but are not limited to beta actin, annexin A6, ferritin light chain fragment (~18 kDa), parathyroid hormone 2 receptor fragment (~20 kDa), and a myosin-IXa fragment.

Identifying and/or using a set of proteins whose concentration or SNO modifications can be measured in a patient with Chagas cardiomyopathy that would indicate progression of cardiomyopathy, or the patient's response to treatment.

Formulating a predictive model consisting of weighted combinations of the same measured levels of specific proteins and SNO modified proteins that indicate risk for developing cardiomyopathy.

Clinical Human Cohorts.

The initial phase of one study utilized representative PBMC samples from seropositive chagasic patients that were clinically characterized in Argentina according to published protocols (Wen et al., (2012) *Mol Cell Proteomics* 11, 435-52). In the state of Salta, at the border of Argentina-Bolivia, Chagas disease is endemic. Patients were tested to be seropositive for *T. cruzi* infection, characterized for cardiac function, and grouped as:

CCM− group. The CCM− group included 25 seropositive, asymptomatic subjects with no indication of cardiac involvement (i.e., no echocardiography abnormalities, preserved systolic function (ejection fraction (EF) ≥55%), no left ventricular dilatations, and negligible-to-minor EKG alterations).

CCM+ group. The CCM+ group included 28 seropositive, symptomatic chagasic patients with a degree of systolic dysfunction (EF: ≤40-54%) and/or left ventricular dilatation (diastolic diameter ≥57 mm).

Classification of Chagas disease was done according to the NYHA Guidelines.

The inventors employ a rigorous blood collection and storage protocol to ensure sample quality. Briefly, heparinized blood (10 ml/subject) is centrifuged at 1000 g, 4° C. for 20 min and the resulting buffy-coat transferred to a new tube containing percoll (1.084 g/L) cushion. After centrifugation as above, PBMCs lying at the PBS-percoll interface are transferred to a new tube, and washed with cold PBS. PBMC pellets are stored at −80° C. for future use.

Saturation Fluorescence Labeling and Cysteinyl-S-Nitrosylation by Fluorescence (SNOFlo).

After cysteine (cysteic acid) content was determined by amino acid analysis (Model L8800, Hitachi High Technologies America, Pleasanton, Calif.), the proteins obtained from PBMCs of Chagasic patients (+/−cardiomyopathy) by urea/thiourea extraction were split into two equal pools. One pool was processed for quantitative saturation fluorescence labeling with uncharged BODIPY FL-maleimide (BD) at a dye-to-protein thiol ratio of greater than 50:1 ratio. This saturation fluorescence labeling method has yielded high accuracy (>91%) in quantifying blinded protein samples (Pretzer and Wiktorowicz, (2008) *Anal Biochem* 374, 250-262).

The second pool was first treated with 6 mM ascorbic acid (Asc) to remove S-nitrosyl (SNO) groups from cysteine residues. These samples were then dialyzed against the urea/thiourea extraction buffer, after which the proteins were labeled with BD as above.

The BD-labeled proteins were separated using two-dimensional gel electrophoresis (2DE) employing an IPGphor multiple sample IEF device (Pharmacia, Piscataway, N.J.) in the first dimension, and Protean Plus and Criterion Dodeca cells (Bio-Rad, Hercules, Calif.) in the second dimension (Jamaluddin et al., (2010) *J Virol* 84, 9533-45). Sample aliquots were first loaded onto 11 cm dehydrated precast immobilized pH gradient (IPG) strips (Bio-Rad), and rehydrated overnight. IEF was performed at 20° C. with the following parameters: 50 Volts, 11 h; 250 V, 1 h; 500 V, 1 h; 1000 V, 1 h; 8000 V, 2 h; 8000 V, 6 h. The IPG strips were then be incubated in 4 mL of equilibration buffer (6 M urea, 2% SDS, 50 mM Tris-HCl, pH 8.8, 20% glycerol) containing 10 µl/mL tri-2 (2-carboxyethyl) phosphine (Geno Technology, Inc., St. Louis, Mo.) for 15 minutes at 22° C. with shaking. The samples were incubated in another 4 mL of equilibration Buffer with 25 mg/mL iodoacetamide for 15 min at 22° C. with shaking in order to ensure protein S-alkylation of any residual reduced thiol groups. Electrophoresis was performed at 150 V for 2.25 h, 4° C. with precast 8-16% polyacrylamide gels in Tris-glycine buffer (25 mM Tris-HCl, 192 mM glycine, 0.1% SDS, pH 8.3) (Pretzer and Wiktorowicz, (2008) *Anal Biochem* 374, 250-262).

Protein Fluorescence Staining. After electrophoresis, the gels were directly imaged at 100 µm resolution using the GE Healthcare Typhoon Trio Proteomic Imaging System to quantify BD-labeled proteins (>90% of human proteins contain at least one cysteine (Miseta and Csutora, (2000) *Mol Biol Evol* 17, 1232-39). A gel containing the most common features was selected by Nonlinear Samespots software (see below) as the reference gel for the entire set of gels. The gel was destained in 20% ethanol/10% acetonitrile, washed with water, and scanned at 485/550 nm (ex/em). The exposure time was adjusted to achieve a value of ~55,000-63,000 pixel intensity (16-bit saturation) from the most intense protein spots on the gel.

Measurement of Relative Spot Intensities.

The 2D gel images were analyzed using Progenesis/SameSpots software (Nonlinear Dynamics, Ltd. Newcastle Upon Tyne, UK). The reference gel was selected according to quality and number of spots. Spots boundaries were established after automated "pixel to pixel" matching with manual adjustment, boundaries were examined to ensure proper distinction, and the gel images were used to obtain the quantitative spot data. This strategy ensures that spot numbers and outlines were identical across all gels in the experiment, eliminating problems with unmatched spots (Dowsey et al., (2010) *Methods Mol Biol* 604, 239-55; 13, 14) as well as ensuring that the greatest number of protein spots and their spot volumes were accurately detected and quantified. Spot volumes were normalized using a software-calculated bias value assuming that the great majority of spot volumes did not change in abundance.

SNOFlo Data Processing.

SNOFlo uses a thiol-reactive fluorescent label to detect free thiols in proteins. The presence of a nitrosyl (NO) group will prevent the labeling of thiols, so that when compared to the same sample for which all NO groups have been removed (Asc+ treatment), SNO labeled proteins will yield spot volumes less than the Asc+ treatment (no NO modification; FIG. 1) (Wiktorowicz et al., (2011) *Biochemistry* 50, 5601-14). However, since one goal was to establish classifiers of chagasic cardiomyopathy, variation in protein intensities (spot volumes) may reflect changes in SNO status, changes in protein abundance, or both. Treatment of half of a patient PBMC extract with Asc removes all NOs, and spot volume ratio within Asc+ treatment, but across patient cardiac status, yields an estimate of the change in protein abundance, while spot volume ratios within Asc-treatment yields a combined estimate of change in SNO and/or protein abundance. Thus in order to normalize the SNO from abundance changes, the inventors calculate a ratio of ratios of Asc− ratios with Asc+ treatment ratios of each protein spot and a normalized SNO ratio according to the equations as follows:

$$\text{Ratio of ratios} = \frac{[BD_{Asc-}^{Exp} / BD_{Asc-}^{Ctrl}]}{[BD_{Asc+}^{Exp} / BD_{Asc+}^{Ctrl}]} = \frac{\Delta[Cys\text{-NO}]}{\Delta[\text{protein}]}$$

where BD=normalized BODIPY fluorescence intensity of a protein spot, $Asc^-$=non-Asc treated, $Asc^+$=Asc treated, Exp=CCM+, Ctrl=CCM−.

However, since particular statistical model building software requires single values from each patient within his/her cohort, only the Asc−/Asc+, and Asc+ ratios were used to determine classifiers, as follows:

$$\text{Normalized SNO Ratio} = \frac{[BD_{Asc-}]}{[BD_{Asc+}]} = \frac{[Cys\text{-NO}]}{[\text{protein}]}$$

to reflect the SNO status of each protein spot, or:

$$\text{Protein Abundance Ratio} = \frac{[BD_{Asc+}^{Exp}]}{[BD_{Asc+}^{Ctrl}]} = \Delta[\text{protein}]$$

to reflect the difference in protein abundance CCM+ to CCM−.

Protein Identification.

Selected 2DE spots were picked robotically, trypsin-digested, and peptide masses identified by MALDI TOF/TOF (AB Sciex 5800, Foster City, Calif.). Data were analyzed with the Applied Biosystems software package included 4000 Series Explorer (v. 3.6 RC1) with Oracle Database Schema Version (v. 3.19.0), Data Version (3.80.0) to acquire both MS and MS/MS spectral data. The instrument was operated in positive ion reflectron mode, mass range was 850-3000 Da, and the focus mass was set at 1700 Da. For MS data, 2000-4000 laser shots were acquired and averaged from each sample spot. Automatic external calibration was performed using a peptide mixture with reference masses 904.468, 1296.685, 1570.677, and 2465.199.

Following MALDI MS analysis, MALDI MS/MS was performed on several (5-10) abundant ions from each sample spot. A 1 kV positive ion MS/MS method was used to acquire data under post-source decay (PSD) conditions. The instrument precursor selection window was +/−3 Da. For MS/MS data, 2000 laser shots were acquired and averaged from each sample spot. Automatic external calibration was performed using reference fragment masses 175.120, 480.257, 684.347, 1056.475, and 1441.635 (from precursor mass 1570.700).

Applied Biosystems GPS Explorer™ (v. 3.6) software was used in conjunction with MASCOT to search the respective protein database using both MS and MS/MS spectral data for protein identification. Protein match probabilities were determined using expectation values and/or MASCOT protein scores. MS peak filtering included the following parameters: mass range 800 Da to 4000 Da, minimum S/N filter=10, mass exclusion list tolerance=0.5

Da, and mass exclusion list (for some trypsin and keratin-containing compounds) included masses 842.51, 870.45, 1045.56, 1179.60, 1277.71, 1475.79, and 2211.1. For MS/MS peak filtering, the minimum S/N filter=10 (Wen and Garg, (2012) *Mol Cell Proteomics* 11, M111.010918. Epub 012011; Wen et al., (2012) *Mol Cell Proteomics* 11, 435-52).

For protein identification, the *Homo sapiens* taxonomy was searched in the NCBI database. Other parameters included the following: selecting the enzyme as trypsin; maximum missed cleavages=1; fixed modifications included carbamidomethyl (C) for 2-D gel analyses only; variable modifications included oxidation (M); precursor tolerance was set at 0.2 Da; MS/MS fragment tolerance was set at 0.3 Da; mass=monoisotopic; and peptide charges were only considered as +1 ((Wen and Garg, (2012) *Mol Cell Proteomics* 11, M111.010918. Epub 012011; Wen et al., (2012) *Mol Cell Proteomics* 11, 435-52).

Protein identification was performed using a Bayesian algorithm (Zhang and Chait, (2000) *Anal Chem* 72, 2482-89) where matches were indicated by expectation score, an estimate of the number of matches that would be expected in that database if the matches were completely random. In some circumstances, confirmation of the protein identification was performed by LC-MS/MS (Orbitrap Velos, ThermoFinnegan, San Jose, Calif.).

Statistical Analysis.

Statistical comparisons were performed using SPSSv18 (SPSS, Inc., Chicago, Ill.) and R.

Multivariate Adaptive Regression Splines (MARS). Log base 2-transformed differential protein expression data and differential protein SNO data were used for MARS modeling. The MARS model specified 6 possible basis functions. MARS is a non-parametric regression method that uses piecewise linear spline functions (basis functions) as predictors. The basis functions are combinations of independent variables and so this method allows detection of feature interactions and performs well with complex data structures (Friedman and Roosen, (1995) *Stat Methods Med Res* 4, 197-217). MARS uses a two-stage process for constructing the optimal classification model. The first half of the process involves addition of basis functions until a user-specified number of basis functions have been reached. In the second stage, MARS deletes basis functions in order, starting with the basis function that contributes the least to the model until an optimum model is reached. Ten-fold generalized cross-validation was used to avoid over-fitting the classification model (Salford Systems, Inc).

Stochastic Search Variable Selection (SSVS). Stochastic variable search is a procedure that selects promising subsets of predictor variables in the defined design matrix, which is based on embedding the entire regression setup in a hierarchical Bayes normal mixture model, where latent variables are used to specify choices of subsets (George and McCulloch, (1993) *J. American Statistical Association* 88, 881-89). Those subsets with higher probability can be identified by their more frequent appearance in the Gibbs sample. The inventors explored different methods to improve the classification accuracy, having fewer misclassifications while using fewer predictors. The WinBUGS software for Bayesian analysis using Markov Chain Monte Carlo (MCMC) method was used.

Proteomic Analyses.

In one study the chagasic cohort consisted of 53 patients in total (25 CCM−; 28 CCM+) in which each sample was split in two with one treated with ascorbate (to reverse SNO modifications) and the other processed without ascorbate. After labeling and spot fluorescence quantification, the first treatment reflects the protein concentration, while the second reflects the degree of SNO modification. Both are useful for establishing candidate classifiers for CCM.

Thus 106 2D gels were analyzed, resulting in the detection of 635 protein spots after filtering and manual examination of the gel images. Two separate ratios of each treatment class with respect to the comparison of CCM+ to CCM− patients were calculated as indicated above. Submitted for statistical analyses were the abundance ratio of each spot (Asc+) CCM+:CCM−, and the normalized SNO ratio (Asc−/Asc+) of CCM+ separately from CCM−.

Statistical Analyses.

Multivariate Adaptive Regression Splines (MARS) is a nonparametric, multivariate regression method that can estimate complex nonlinear relationships by a series of spline functions of the predictor variables. Regression splines seek to find thresholds and breaks in relationships between variables and are very well suited for identifying changes in the behavior of individuals or processes over time. As a nonparametric approach, MARS does not make any underlying assumptions about the distribution of the predictor variables of interest. This characteristic is useful in chagasic cardiomyopathy modeling because protein expression values are not normally distributed, as would be required for the application of classical modeling techniques such as logistic regression. The basic concept behind spline models is to model using potentially discrete linear or nonlinear functions of any analyte over differing intervals. The resulting piecewise curve, referred to as a spline, is represented by basis functions within our model. Other studies have shown that MARS is a superior method in the prediction of non-parametric datasets to phenotypes (Brasier et al., (2010) *Clin Transl Sci* 3, 147-57). To reduce over-fitting, the inventors restricted their analysis to models that incorporated one or fewer interaction terms.

The MARS model specified 15 possible basis functions and allowed only 1 interaction term. Ten-fold cross-validation, a more accurate way to measure how efficiently the classifier has learned a concept base using the training set, was used to avoid over-fitting the classification model (Salford Systems, Inc).

The 2D gel electrophoresis data were initially analyzed using Student's t-test, and was performed on two separate classes of data derived from the 635 protein spots that were quantified. The first was performed on the ratio of SNO signal (Asc−) and abundance signal (Asc+); this ratio normalized the SNO signal (Asc−) against the protein abundance indicator (Asc+) for each protein spot. Of the 635 spots detected by 2D gel electrophoresis, 23 had significant p-values (<0.05) for Asc−/Asc+. The second class of data considered only the change in protein abundance (Asc+) between CCM− and CCM+ patients. From this analysis, 13 spots exhibited significant p-values between CCM− and CCM+ patients. Between the two classes of data, the common spots were spot 267, spot 650, and spot 735. The 33 spots in total were used to create a classification model using MARS.

Figure 2:
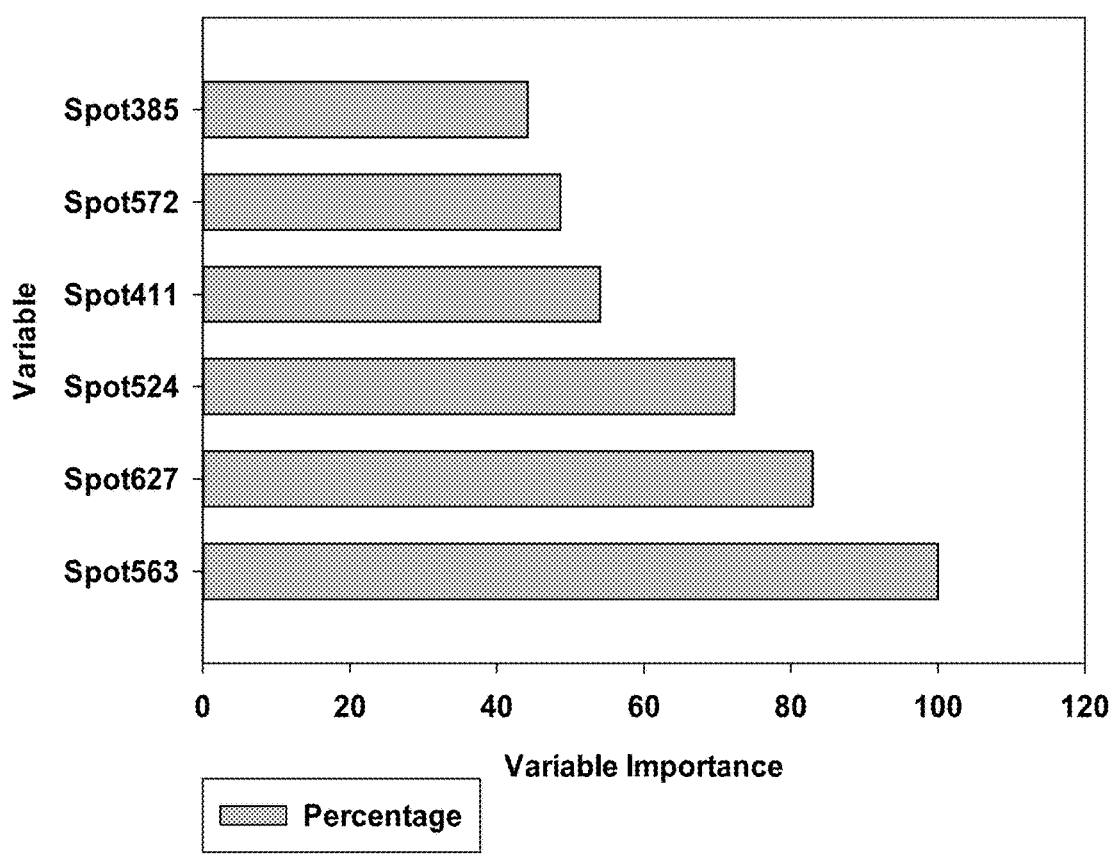
FIG. 2. Variable Importance for MARS model of CCM+. Variable importance was computed for each feature in the MARS model. Y-axis, percent contribution for each analyte.

The inventors used the log 2 transform of all the data present in the modeling process, with a possible maximum of 15 basis functions and 1 possible interaction term. This resulted in a model with 6 variables whose relative importance to the model is shown in FIG. 2, where spot 563 (100%) was the most influential and spot 385 the least. This model resulted in 100% accuracy for classifying CCM+/CCM− patients. The distributions of each spot selected in the MARS model are shown in the box plots (FIGS. 5-10).

Figure 3:
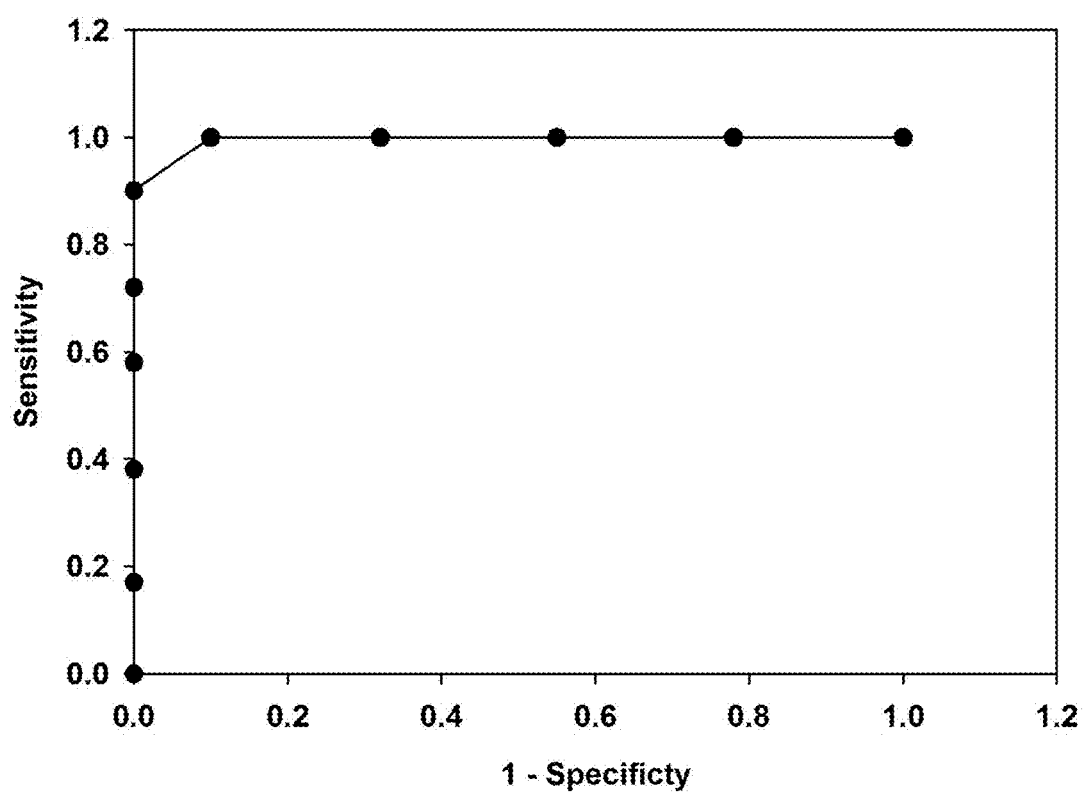
FIG. 3. ROC analysis. Shown is a Receiver Operating Characteristic (ROC) curve for the predictive model for CCM+. Y-axis, Sensitivity; X-axis, 1-Specificity.

The MARS model was unable to produce a highly accurate classifier of CCM+. The resultant model was able to accurately predict CCM− status with 100% accuracy, but only 78% accuracy for the CCM+ patients. This resulted in an overall accuracy of 89%. The AUC (area under the curve) for such a model is 0.99 (FIG. 3).

The optimal MARS model is represented by 6 basis functions. The resultant classification model for these 6 basis functions is Y=1.03427+0.586711*BF2−0.178427*BF5−0.638033*BF10−0.263085*BF11−0.244576*BF12+2.64392*BF14 (Table I).

Figure 11:
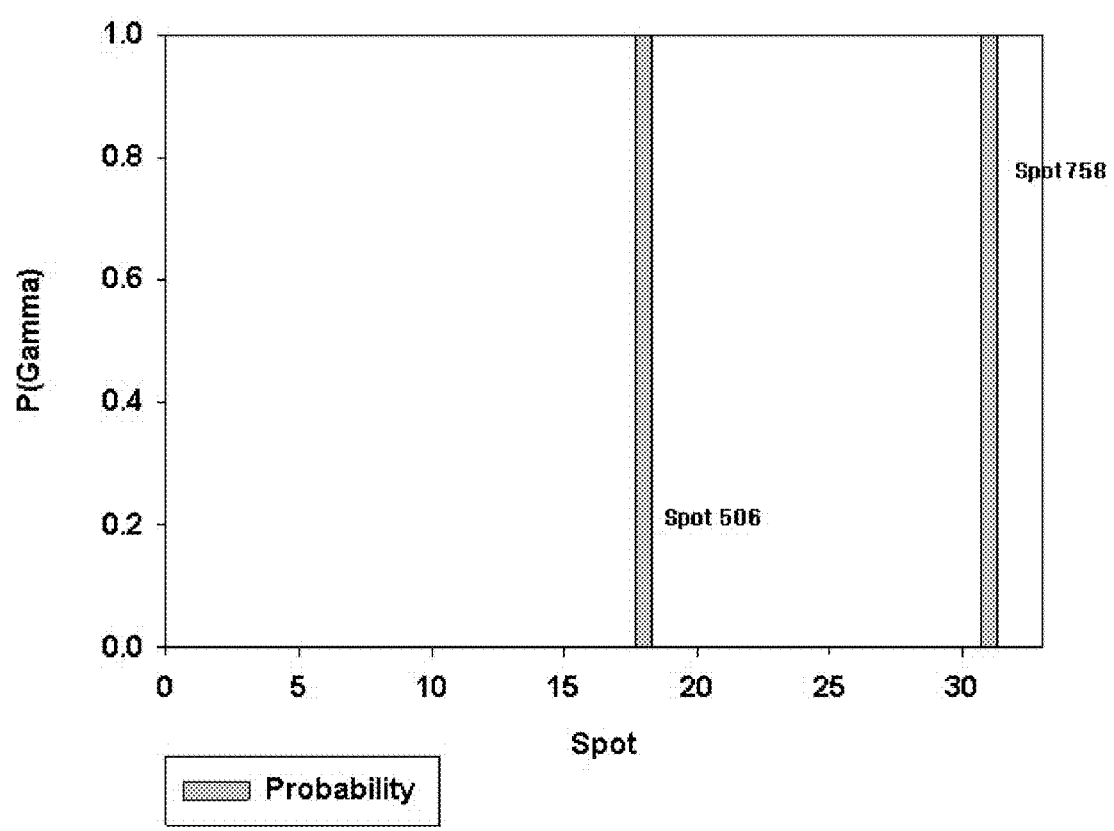
FIG. 11. Probability of inclusion parameters from Stochastic Search Variable Selection model.
Figure 12:
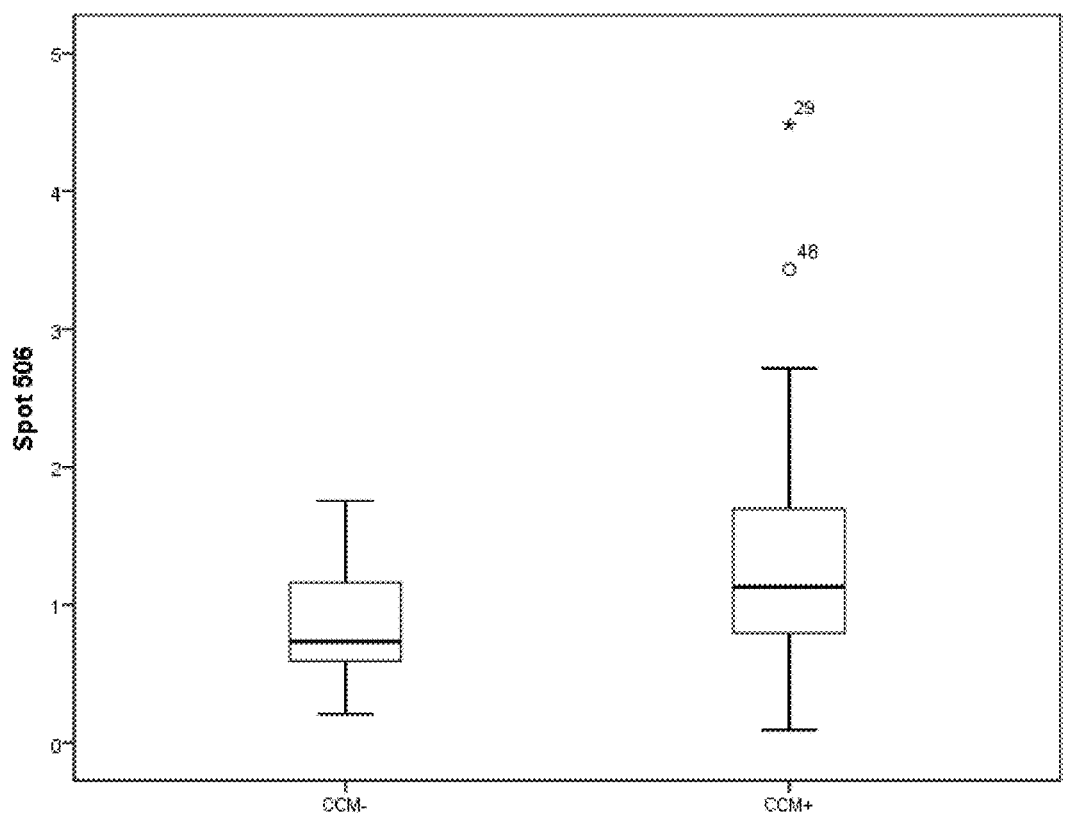
FIG. 12. SSVS model differential 2DE spot abundance in chagasic cardiomyopathy. Shown is a box-plot comparison of 2DE spot values between CCM+ and CCM− for spot 506, SNO modified parathyroid hormone receptor.
Figure 13:
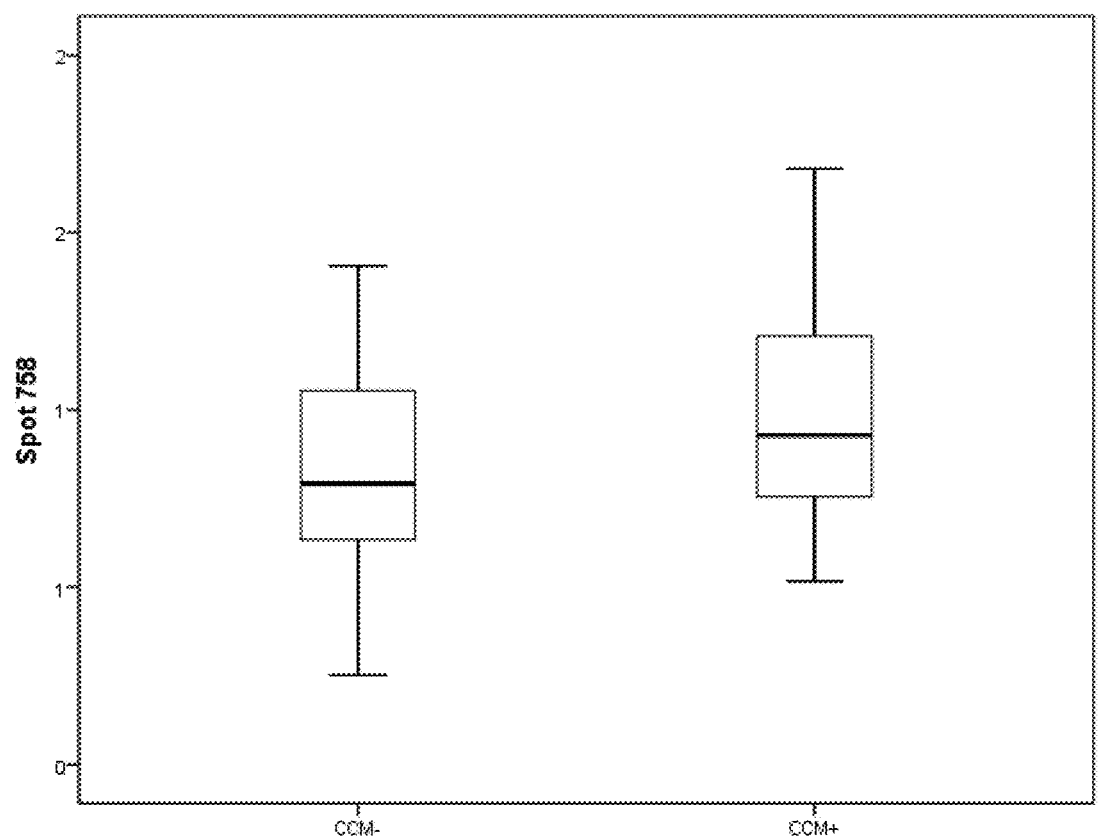
FIG. 13. SSVS model box-plot comparison of 2DE spot values between CCM+ and CCM− for spot 758, SNO modified beta actin.

The optimal Stochastic Search Variable Selection (SSVS) model with spike and slab priors identified spots 506 and 758 to differentiate CCM+ from CCM− patients. The marginal probability of each spot of being selected is shown in the probability plot (FIG. 11). The distributions of protein expression by disease classification are shown in the box plots (FIGS. 12 and 13). The Gibbs sampler method for SSVS allows for the interrogation of the model space efficiently without fitting all possible models with the inferences not driven by the model assumptions. The Bayesian hierarchical methods to variable selection and classification are complementary approaches of omic data in that the uncertainty in the model choice can be incorporated into the analysis. For analysis of the data with 33 spots, the 25,000 iterations of the MCMC were completed by removing the first 1000 for burn-in and saving every $5^{th}$ iteration. In the case of a binary outcome, the latent probit model in which posteriors distribution for the latent indicator variables are estimated via MCMC could be used.

Figure 4:
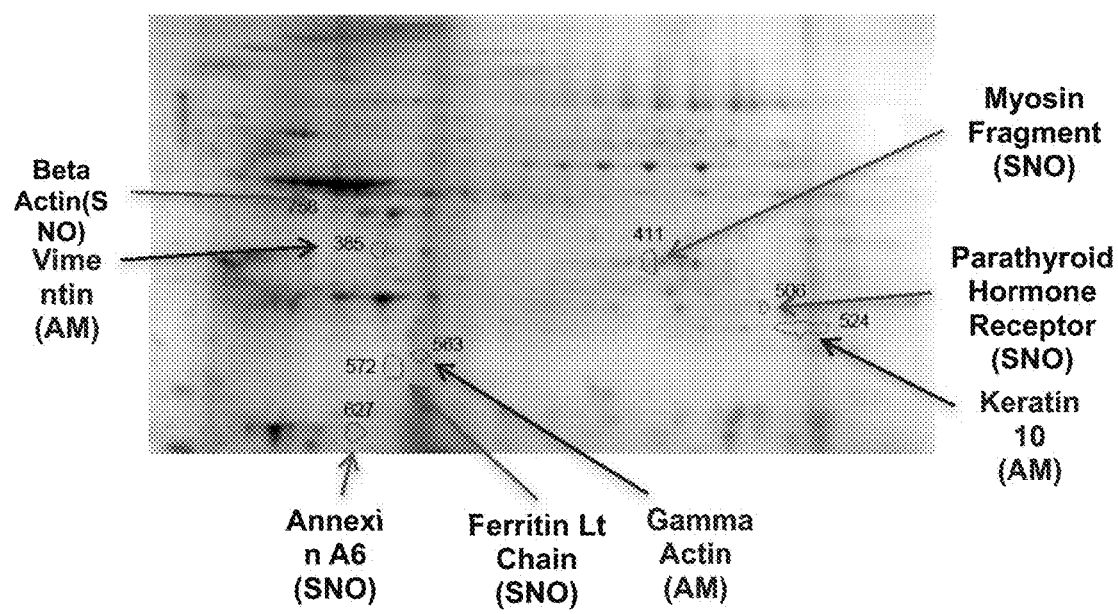
FIG. 4. 2DE images. Shown is a reference gel of 2DE of proteins from the chagasic study subjects. The locations and identities of protein spots that contribute to the prediction of chagasic cardiomyopathy are indicated. SNO=proteins whose SNO modification is discriminatory; AM=proteins whose abundance is discriminatory.
Figure 5:
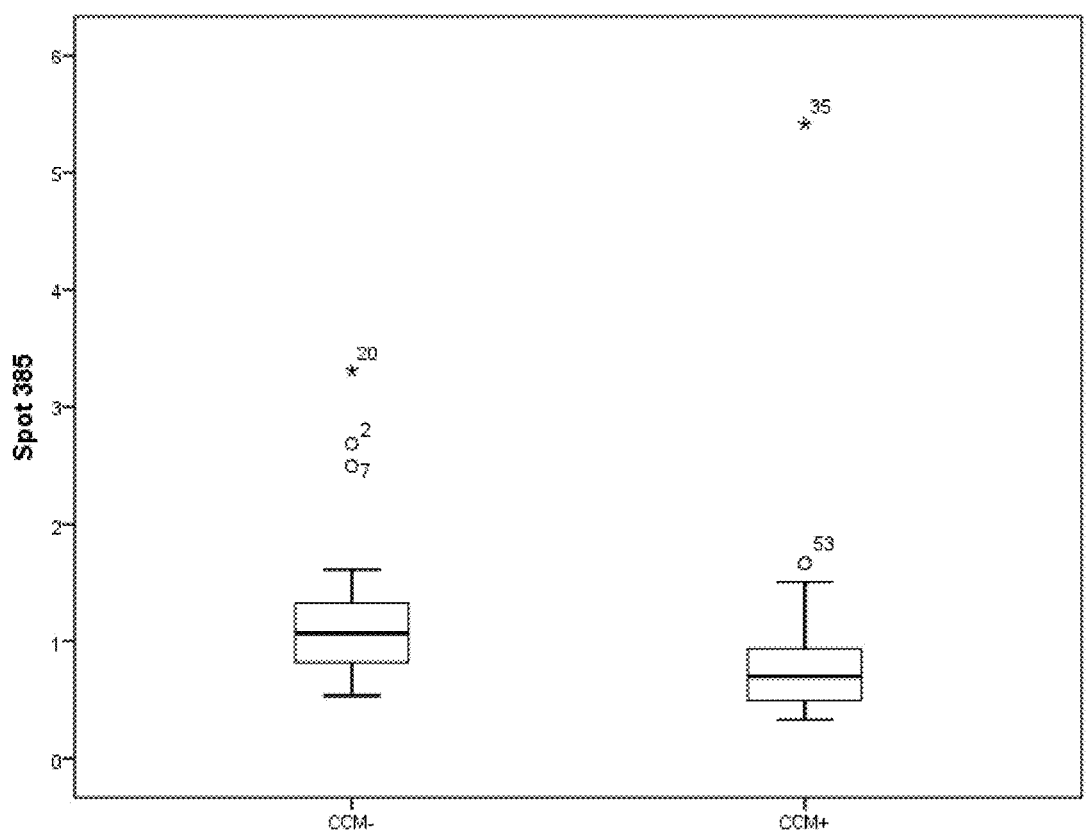
FIG. 5. Box plot of spot 385 identified as an abundance modulated vimentin.
Figure 6:
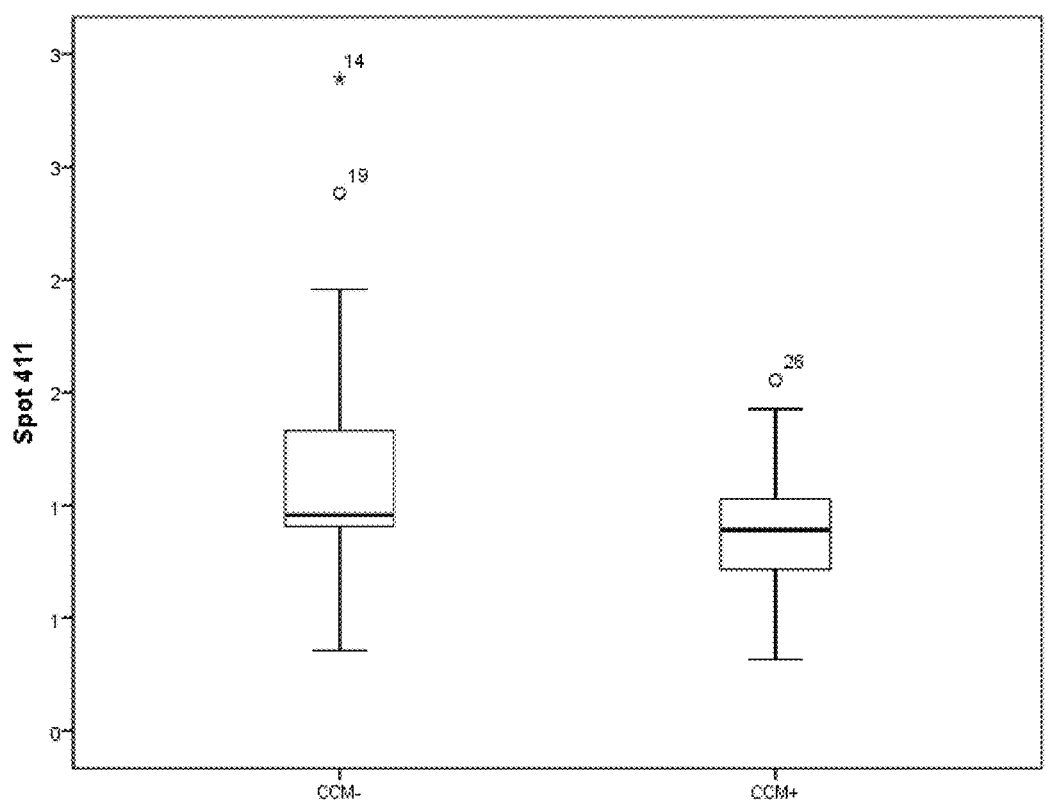
FIG. 6. Box plot of spot 572 identified as an SNO modified ferritin light-chain.
Figure 7:
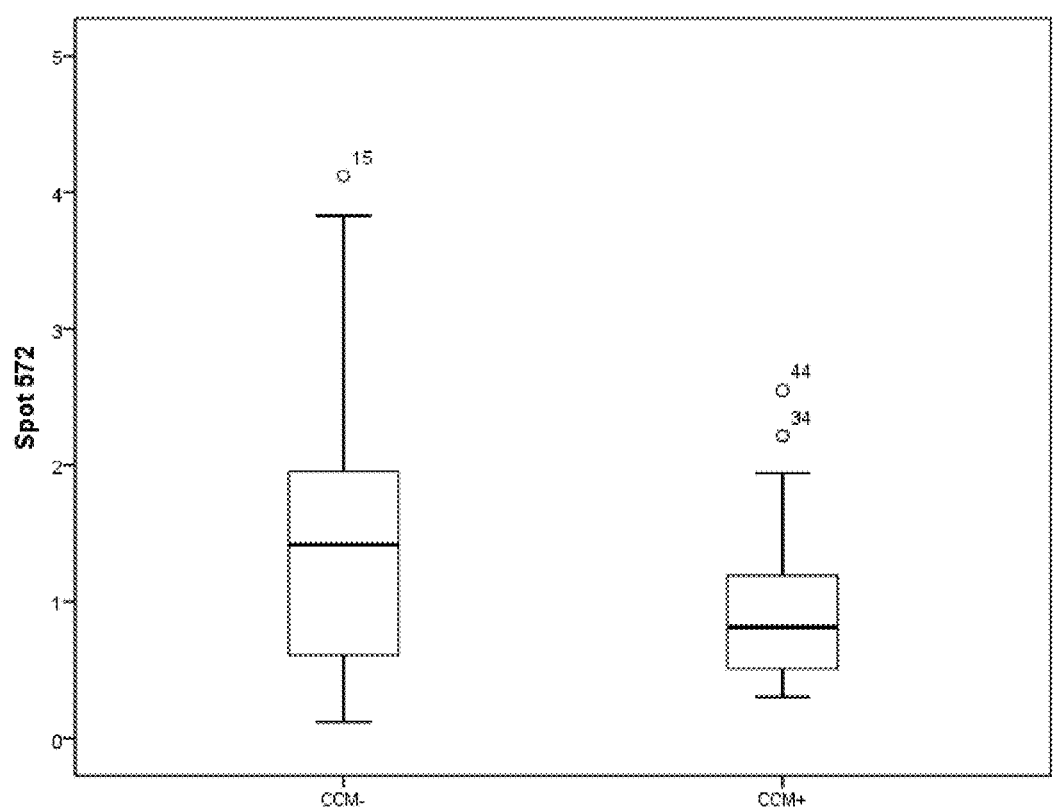
FIG. 7. Box plot of spot 411 identified as an SNO modified myosin fragment.
Figure 8:
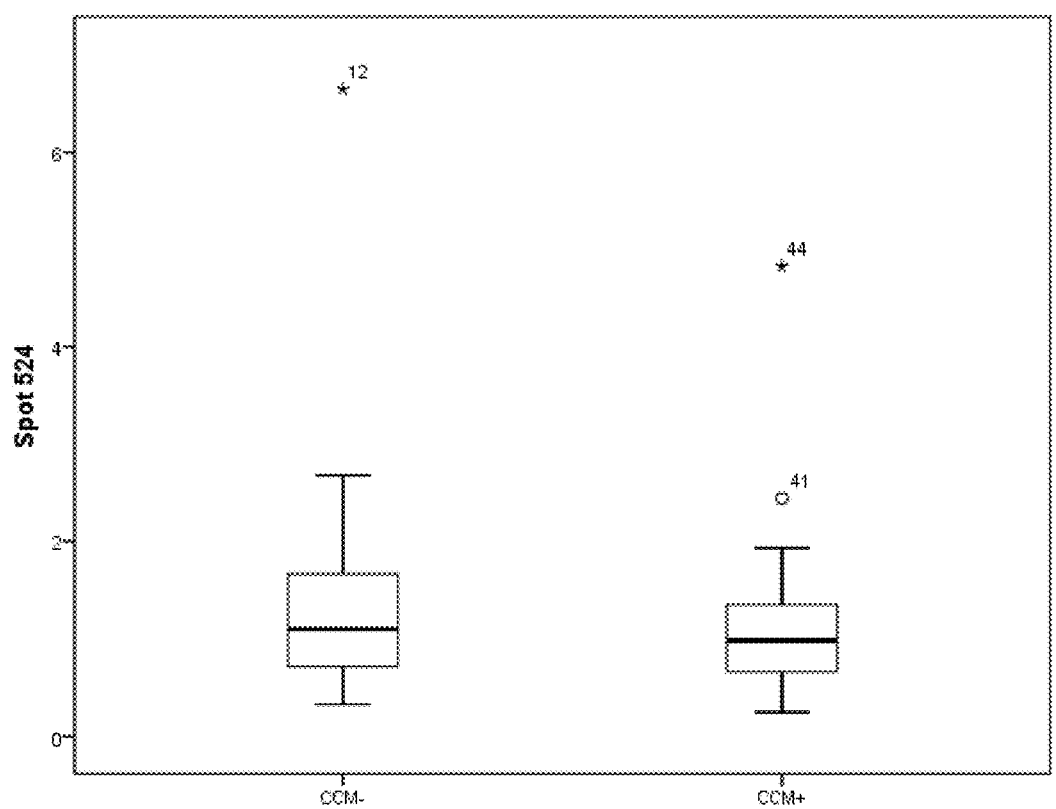
FIG. 8. Box plot of spot 524 identified as an abundance modulated keratin 10.
Figure 9:
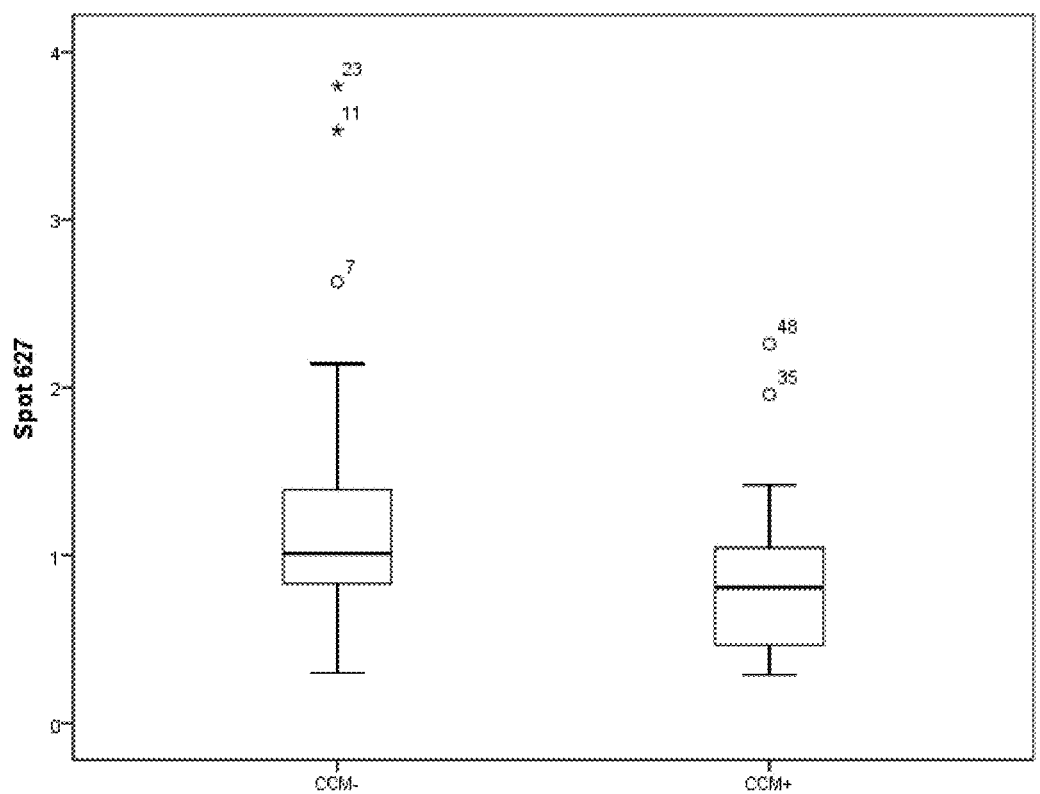
FIG. 9. Box plot of spot 627 identified as an SNO modified annexin A6.
Figure 10:
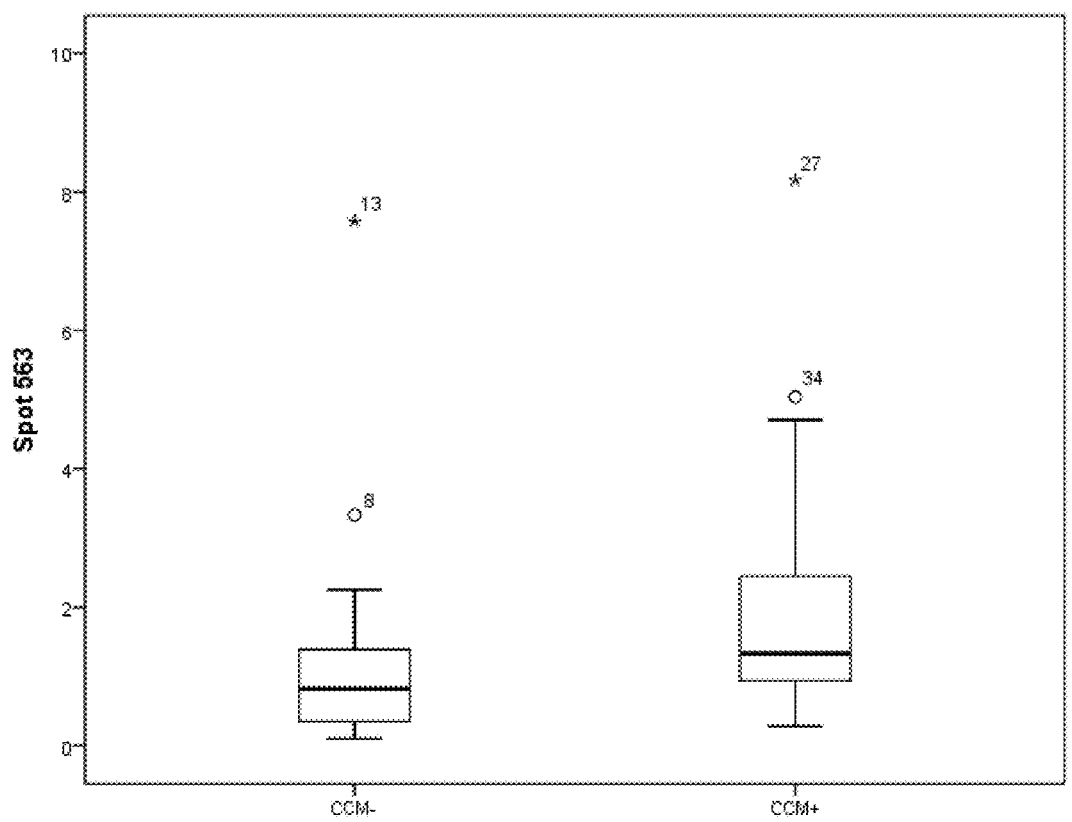
FIG. 10. Box plot of spot 563 identified as an abundance modulated gamma actin.

The positions of the MARS and the SSVS selected spots are shown in the SameSpots selected reference gel (FIG. 4), with each spot showing its identity and its selection criterion (either abundance or SNO). The protein IDs and other quantitative information are shown in Table II.

Evaluation of the model performance is seen by analysis of the area under the Receiver Operating Characteristic (ROC) curve (AUC), where sensitivity vs. 1-specificity was plotted. In the ROC analysis, a diagonal line (45 degree slope) starting at zero indicates that the output was a random guess, whereas an ideal classifier with a high true positive rate and low false positive rate will curve positively and strongly towards the upper left quadrant of the plot (Fawcett, (2006) *Pattern Recognition Letters* 27, 861-74). The AUC is equivalent to the probability that two cases, one chosen at random from each group, are correctly ordered by the classifier (Hanley and McNeil, (1982) *Radiology* 143, 29-36). The AUC for the CCM+ model is 0.998.

TABLE I

MARS Basis Functions.

| $B_m$ | Definition | $a_m$ | Variable descriptor |
|---|---|---|---|
| BF2 | $(1.07 - \text{Spot } 385)_+$ | 5.87E−1 | Spot 385 (vimentin-abundance) |
| BF5 | $(\text{Spot } 572 - 0.72))_+$ | 1.78E−1 | Spot 572 (ferritin light chain-SNO) |
| BF10 | $(1.09 - \text{Spot } 563)_+$ | 6.38E−1 | Spot 563 (gamma actin-abundance) |
| BF11 | $(\text{Spot } 627 - 0.29)_+$ | 2.63E−1 | Spot 627 (annexin A6-SNO) |
| BF12 | $(\text{Spot } 524 - 0.25)_+$ | 2.45E−1 | Spot 524 (keratin 10-abundance) |
| BF14 | $(0.75 - \text{Spot } 411))_+$ | 2.64 | Spot 411 (myosin fragment-SNO) |

Shown are the basis functions (BF) for the MARS model for chagasic cardiomyopathy where, Bm = each individual basis function, $a_m$ = coefficient of the basis function, $(y)_+$ = max(0, y). The actual model is: Y = 1.03427 + 0.586711*BF2 − 0.178427*BF5 − 0.638033*BF10 − 0.263085*BF11 − 0.244576*BF12 + 2.64392*BF14, where BF2 = max(0, 1.07265 − Spot 385), BF5 = max(0, Spot 572 − 0.721195), BF10 = max(0, 1.9067 − Spot 563), BF11 = max(0, Spot 627 − 0.288306), BF12 = max(0, Spot 524 − 0.248617), and BF14 = max(0, 0.74921 − Spot 411)

TABLE II

Spot identities obtained by mass spectrometry. Both abundance and normalized SNO classifiers are provided. t-test values refer to either abundance or SNO ratios, whichever is provided. SSVS denotes spots were selected by Stochastic Search Variables Selection, not t-test. Identities with MS Scores greater than 56 have significance levels of identification greater than 95%.

| No. | Protein name | SwissProt Accession | pI | MW (kDa) | MS Score | Abundance CCM+:CCM− | t test (p) | CCM+ SNO Ratio | CCM− SNO Ratio |
|---|---|---|---|---|---|---|---|---|---|
| 1 | Vimentin | F5H288 | 5.72 | 29 | 171 | 1.43 | 0.006 | | |
| 2 | Ferritin-light chain | PO2792 | 5.80 | 18 | 74 | | 0.023 | −1.04 | 1.52 |
| 3 | γ-Actin | I3L1U9 | 5.99 | 18 | 137 | −1.82 | 0.031 | | |
| 4 | Annexin A6 | E5RIU8 | 5.47 | 15 | 103 | | 0.040 | −1.18 | 1.30 |
| 5 | Keratin 10 | P13645 | 9.34 | 19 | 286 | 1.54 | 0.046 | | |
| 6 | Myosin-IXa fragment | | 7.98 | 26 | 46 | | 0.038 | −1.11 | 1.15 |
| 7 | Parathyroid hormone receptor | H7C0B0 | 8.92 | 20 | 42 | | SSVS | 1.36 | −1.15 |
| 8 | β-Actin | B4E335 | 5.44 | 38 | 624 | | SSVS | −1.02 | −1.23 |

TABLE III

Summary of proteins selected.
SUMMARY OF PROTEINS SELECTED BY p-VALUE AND RATIOS (ABUNDANCE OR RoR)

| No. | Protein name | Accession No. | pI (Gel) | MW (kD) (Gel) |
|---|---|---|---|---|
| 1 | Vincolin | P18208 | 7.53 | 99 |
| 2 | Serum albumin (Fragment) | H0YA55 | 5.97 | 63 |
| 3 | Isoform 3 of Integrin alpha-IIb | P08514-3 | 4.19 | 55 |
| 4 | Isoform H7 of Myeloperoxidase | P05164-3 | 0.41 | 56 |
| 5 | Actin, cytoplasmic 2, N-terminally processed | F5H0N0 | 6.41 | 41 |
| 6 | Talin 1 | Q5TCU6 | 5.18 | 32 |
| 7 | Actin, cytoplasmic 1, N-terminally processed | B4E335 | 4.88 | 30 |
| 8 | Actin, cytoplasmic 1, N-terminally processed | B4DW52 | 7.51 | 26 |
| 9 | Unconventional myosin-IXa | H3BMM1 | 7.98 | 26 |
| 10 | Peptidyl-prolyl cis-trans isomerase A | P62937 | 8.03 | 26 |
| 11 | WD repeat-containing protein 49 | F8WBC8 | 8.84 | 23 |
| 12 | Keratin, type II cytoskeletal 1 | P04264 | 7.12 | 20 |
| 13 | Parathyroid hormone 2 receptor (Fragment) | H7C0B0 | 8.92 | 20 |
| 14 | Proteasome subunit beta type-2 | P49721 | 7.95 | 19 |
| 15 | Ferritin light chain | P02792 | 5.8 | 18 |
| 16 | Annexin | E5RIU8 | 5.47 | 15 |
| 17 | Actin, cytoplasmic 1, N-terminally processed | G5E9RD | 5.12 | 15 |
| 18 | Keratin, type I cytoskeletal 10 | P13645 | 7.71 | 15 |
| 19 | Heterogeneous nuclear ribonucleoprotein A1 (Fragment) | F6W646 | 7.26 | 15 |
| 20 | SH3 domain-binding glutamic acid-rich-like protein 3 | Q9H299 | 4.32 | 10 |
| 21 | Ras-related protein Rap-1b | B4E335 | 4.4 | 0 |
| 22 | Actin, cytoplasmic 1, N-terminally processed | B4E335 | 5.44 | 38 |
| 23 | Actin, cytoplasmic 1, N-terminally processed | B4E335 | 7.47 | 78 |
| 24 | POTE ankyrin domain family member F | A5A3E0 | 6.57 | 41 |
| 25 | Vimentin | F5H288 | 5.72 | 29 |
| 26 | Protein S100-A11 | P31949 | 6.9 | 10 |
| 27 | Isoform 2 of Fibrinogen alpha chain | P02671-2 | 8.84 | 41 |
| 28 | Tubulin beta chain | Q5JP53 | 0.33 | 34 |
| 29 | Myosin regulatory light chain 12B | O14950 | 4.38 | 17 |
| 30 | Annexin A3 | P12429 | 6.09 | 28 |
| 31 | Keratin, type 1 cytoskeletal 10 | P13645 | 9.34 | 19 |
| 32 | Actin, cytoplasmic 2, N-terminally processed (Fragment) | I3L1U9 | 5.99 | 18 |
| 33 | ATP synthase subunit alpha | ABK092 | 5.64 | 16 |

| No. | MS ID Expectation Value | Abundance Ratio | p-Value (Asc+ <0.05) | Ratio of Ratios | p-Value (Asc− <0.05) | Selection Criterion |
|---|---|---|---|---|---|---|
| 1 | 1.9905E−19 | 1.32 | 0.182504 | −1.32 | 0.044584 | RoR |
| 2 | 1.5811E−12 | −1.25 | 0.204533 | 1.69 | 0.033111 | |
| 3 | 1.2559E−22 | 1.17 | 0.339162 | −1.06 | 0.027258 | |
| 4 | 9.9763E−04 | 1.75 | 0.125809 | −1.71 | 0.045972 | |
| 5 | 1.9905E−06 | 1.30 | 0.034774 | −1.34 | 0.047502 | |
| 6 | 1.5811E−14 | −1.07 | 0.350146 | 1.26 | 0.034137 | |
| 7 | 1.2559E−42 | −1.10 | 0.291819 | 1.17 | 0.006024 | |
| 8 | 3.9715E−09 | 1.13 | 0.116141 | −1.27 | 0.023729 | |
| 9 | 1.9905E+00 | −1.02 | 0.516115 | −1.13 | 0.037733 | |
| 10 | 7.9245E−07 | −1.10 | 0.195105 | 1.14 | 0.021102 | |
| 11 | 1.9905E+00 | 1.37 | 0.413441 | 1.09 | 0.042012 | |
| 12 | 3.9716E−11 | −1.09 | 0.61982 | −1.27 | 0.012075 | |
| 13 | 5.0000E+00 | −1.33 | 0.051258 | 1.50 | 0.033418 | |
| 14 | 5.0000E−04 | −1.08 | 0.532056 | −1.23 | 0.02477 | |
| 15 | 3.1548E−03 | 1.23 | 0.08741 | −1.15 | 0.023404 | |
| 16 | 3.9716E−06 | 1.44 | 0.150651 | −1.38 | 0.040421 | |
| 17 | 3.9716E−15 | 1.05 | 0.915841 | −1.19 | 0.020184 | |
| 18 | 1.5811E+00 | −1.00 | 0.214532 | −1.20 | 0.045743 | |
| 19 | 5.0000E−06 | −1.47 | 0.016761 | 1.52 | 0.043125 | |
| 20 | 9.9763E−31 | 1.29 | 0.029492 | −1.30 | 0.032468 | |
| 21 | 1.2559E−01 | 1.23 | 0.180346 | −1.22 | 0.040693 | |
| 22 | 3.1548E−58 | −1.01 | 0.956162 | 1.15 | 0.037653 | |
| 23 | 3.1548E−41 | 1.50 | 0.158319 | −1.44 | 0.02411 | |
| 24 | 6.2946E−08 | 1.39 | 0.0115 | −1.35 | | Abundance |
| 25 | 6.2946E−13 | 1.43 | 0.00623 | −1.41 | | |
| 26 | 1.9905E−20 | −1.60 | 0.037919 | 1.19 | | |
| 27 | 3.1548E−01 | −1.45 | 0.035493 | 1.04 | | |
| 28 | 6.2946E−08 | −1.20 | 0.034097 | 1.19 | | |
| 29 | 7.0245E−28 | −1.19 | 0.047581 | 1.07 | | |
| 30 | 9.9753E−51 | −1.41 | 0.027378 | 1.34 | | |
| 31 | 1.9905E−24 | 1.55 | 0.046182 | −1.35 | | |
| 32 | 1.5811E−09 | −1.83 | 0.030027 | 2.47 | | |
| 33 | 2.5050E−05 | 1.27 | 0.038451 | 1.17 | | |

Figures 15A, 15B, 15C, 15D:
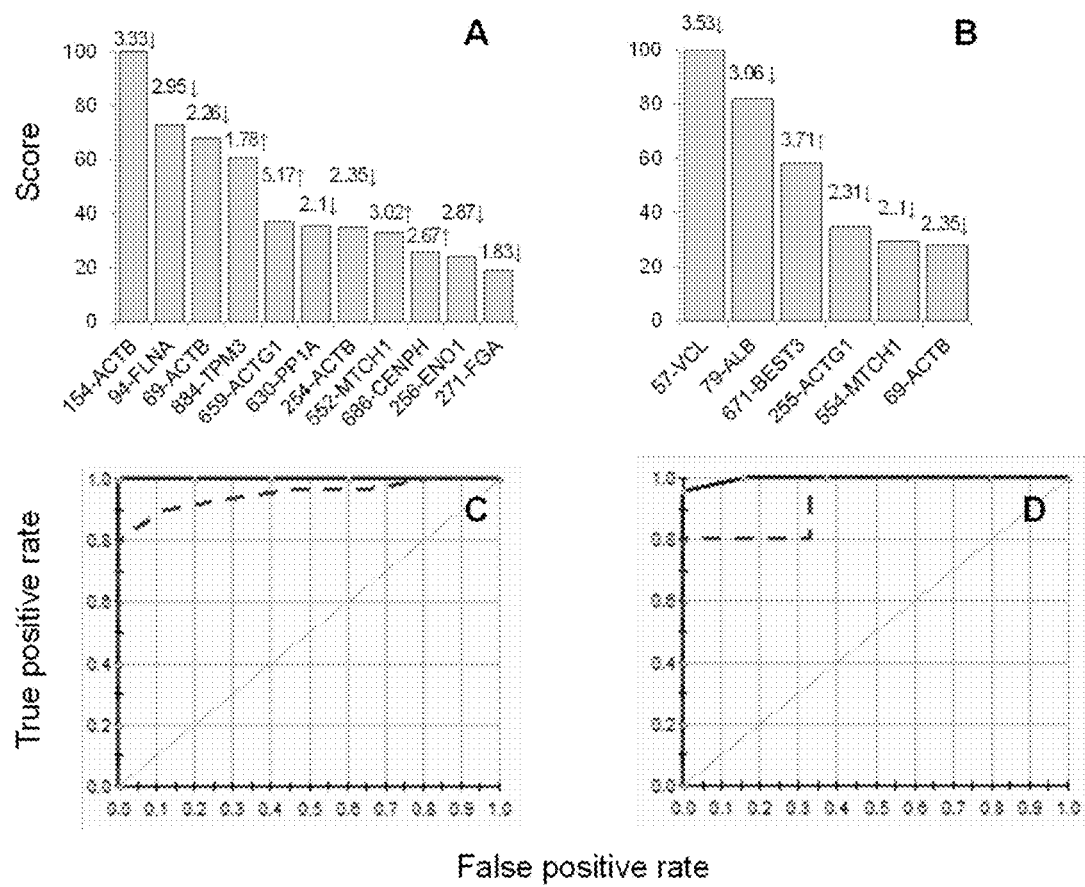
FIG. 15A-15D. MARS analysis of differentially abundant protein spots in C/A (clinically asymptomatic chagasic) subjects.

MARS analysis of differentially abundant protein spots in C/A (clinically asymptomatic chagasic) subjects. Input to the model were protein spots that were differentially expressed at p<0.001 in C/A (84 spots, n=25) subjects with respect to N/H (normal healthy) controls (n=30). 10-fold cross-validation was employed (FIG. 15A and FIG. 15C) and 80% testing/20% training (FIG. 15C and FIG. 15D) approaches to assess the fit of the model for testing dataset. Shown are the protein spots identified with high ranking (score >20) by CV (FIG. 15A) and 80/20 (FIG. 15B) approaches for creating the MARS model for classifying C/A from N/H subjects. Protein spots in FIG. 15A and FIG. 15B are identified as spot #-protein name and fold change (increase ↑, decrease ↓) are plotted on each bar. The ROC curves show the prediction success of the CV (FIG. 15C) and 80/20 models (FIG. 15D). curves: training data ((AUC/ROC: 1.00), and testing data (AUC/ROC: 0.96 for CV and 0.933 for 80/20).

Figures 16A, 16B, 16C, 16D:
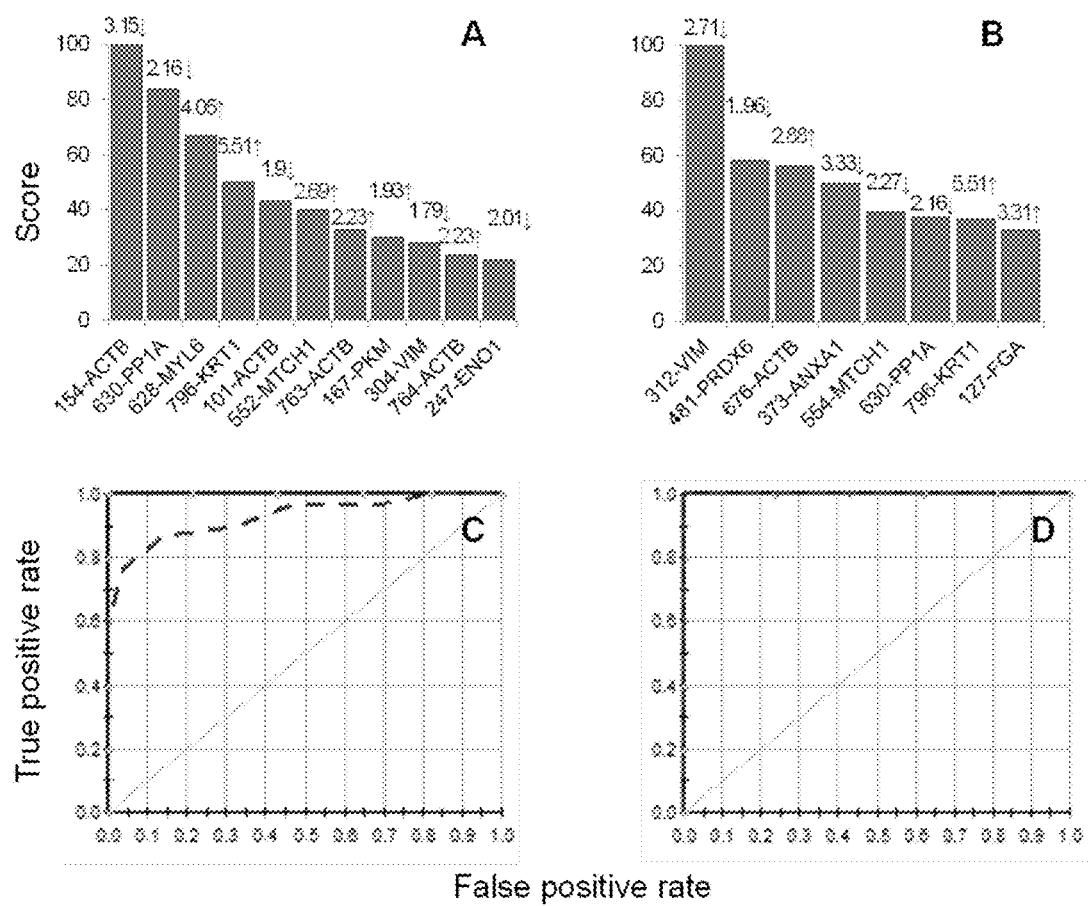
FIG. 16A-16D. MARS analysis of differentially abundant protein spots in C/S (clinically symptomatic chagasic) subjects.

MARS analysis of differentially abundant protein spots in C/S (clinically symptomatic chagasic) subjects. Input to the model were protein spots that were differentially expressed at p<0.001 in C/S (87 spots, n=25) subjects with respect to N/H controls (n=30). 10-fold cross-validation was employed (FIG. 16A and FIG. 16C) and 80% testing/20% training (FIG. 16C and FIG. 16D) approaches to assess the fit of the model for testing dataset. Shown are the protein spots identified with high ranking (score >20) by CV (FIG. 16A) and 80/20 (FIG. 16B) approaches for creating the MARS model for classifying C/S subjects from N/H subjects. Protein spots in FIG. 16A and FIG. 16B are identified as spot #-protein name and fold change (increase ↑, decrease ↓) are plotted on each bar. The ROC curves show the prediction success of the CV (FIG. 16C) and 80/20 models (FIG. 16D). curves: training data ((AUC/ROC: 1.00), and testing data (AUC/ROC: 0.926 for CV and 1.0 for 80/20).

Certain embodiments include biomarkers identified in a previous study. Parasite persistence and oxidative damage in the heart are known to be of pathological significance during Chagas disease (Zacks et al., (2005) *An Acad Bras Cienc*, 77, 695-715; Gupta et al., (2009) *Interdiscip Perspect Infect Dis*, 2009, 190354). Infected rats treated with an anti-parasite drug (BZ) and/or antioxidant (PBN) showed that the beneficial effects of these treatments in controlling parasite- and oxidative stress-induced pathology, respectively (Wen et al., (2006) *Am J Pathol*, 169, 1953-1964; Wen et al., (2010) *J Am Coll Cardiol*, 55, 2499-2508), are reflected in a plasma proteome profile of chagasic rats. In the previous study the inventors identified 92 proteins that were differentially expressed or oxidized in chagasic plasma. Functional analysis allocated a majority of these proteins to inflammation/immunity and lipid metabolism categories, and to molecular pathways associated with cardiovascular dysfunction, e.g., myocardial infarction, hypertrophy, and fibrosis, and pulmonary embolism and hypertension. Some proteins in chagasic rats treated with PBN and/or BZ were allocated to curative pathways (immune regulation and cardiac remodeling). The 2D-GE results were validated by Western blotting. It was demonstrated that the disease-associated increased expression of GSN and VIM, and release of cardiac MYL2 in the plasma of chagasic rats was normalized by PBN/BZ treatment. Increased plasma levels of GSN, MYL2, and VIM were directly correlated with the severity of cardiac disease in human chagasic patients. This is the first study demonstrating that the plasma oxidative and inflammatory response profile and plasma detection of cardiac proteins parallel the pathologic events contributing to Chagas disease development. These findings have utility in diagnosing disease severity and designing suitable therapy for management of human chagasic patients.

Inflammation/Immune Response.

Ingenuity Pathway Analysis (IPA) is a highly curated and comprehensive software used for the integration of proteins into networks and pathways with biological meaning (Thomas and Bonchev, (2010). *Hum Genomics*, 4, 353-360). Network analysis of the plasma proteome profile of chagasic rats identified four major sub-networks linked to host response to *T. cruzi* infection and disease development (Table V). The maximal numbers of the differentially expressed plasma proteins (19 proteins) in chagasic rats were associated with antigen presentation and inflammatory response category (Table V) and indicators of persistent inflammation, known to be of pathological significance in Chagas disease (Dhiman et al., (2009) *Clinical and Vaccine Immunology*, 16, 660-666; Tanowitz et al., (2009) *Prog Cardiovasc Dis*, 51, 524-539; Junqueira et al., (2010) *Expert Rev Mol Med*, 12, e29). Following functional analysis of the inflammation-associated proteins, 12 proteins (APOA1, APOE, C3, CFB, CFH, FGB, GSN, KRT10, PLG, SCG2, SERPINA1, and SERPINC1) were identified as being involved in immune cell trafficking and cell movement of leukocytes, granulocytes, phagocytes, neutrophils, and dendritic and antigen presenting cells. Some of the differentially expressed proteins in inflammation category were associated with activation (APOE, C3, CFH, GC and PLG), chemotaxis (C3, SCG2, SERPINA1, SERPINC1), and infiltration of leukocytes (APOA1, APOE, C3, PLG, KRT10) and neutrophils (C3, CFB, CFH, PLG). Up regulation of APOE, APOA1, APOH, GC and PLG in chagasic plasma was indicative of activation, binding and accumulation of macrophages in the disease state. Of the 19 differentially expressed inflammation-associated proteins, 11 proteins (APOE, C3, CFB, CFH, GSN, KRT10, SCG2, SERPINA1, SERPINC1, GC, and PLG) were carbonylated in chagasic plasma. PBN treatment prevented the oxidative modification of five of these proteins (i.e., CFB, CFH, SERPRINA1, SERPINC1, and PLG). Interestingly, PBN treatment also normalized or regulated the expression of several inflammation-associated proteins, including APOH, APOE, CFH, PLG and SCG2 in acutely infected rats and APOH, GC, GSN and PLG in chronically infected rats; while the expression level of CFB, GSN, C3, and SERPINC1 was partly regulated by PBN in infected rats (Tables IVa-IVb). Other proteins (APOE, C3, KRT3, and SCG2) were exposed to oxidation due to *T. cruzi*-induced, acute oxidative stress, but were normalized in expression and oxidation during the chronic phase.

Treatment of rats with anti-parasite drug (BZ) was not effective in preventing protein carbonylation. These observations indicate that oxidative stress plays an important role in modulating the host immune response against *T. cruzi*. ROS elicit inflammatory cytokines (e.g. TNF-α, IFN-γ, IL-1α) in cardiomyocytes infected by *T. cruzi* (Gupta et al., (2009) *Free Radio Biol Med*, 47, 1414-21; Ba et al., (2010) *J Biol Chem*, 285, 11596-606). Inflammatory pathology was controlled in chronically infected experimental animals and human patients by enhancing the antioxidant status, which was also beneficial in preserving the cardiac function during Chagas disease (Wen et al., (2006) *Am J Pathol*, 169, 1953-1964; Wen et al., (2010) *J Am Coll Cardiol*, 55, 2499-2508; Ba et al., (2010) *J Biol Chem*, 285, 11596-606; Souza et al., (2010) *Mem Inst Oswaldo Cruz*, 105, 746-751). Recent observations indicate that the mitochondrial release of ROS due to electron transport chain dysfunction and enhanced release of electrons to molecular oxygen is the primary source of oxidative stress in the heart (Wen and Garg, (2008) *J Bioenerg Biomembr,* 40, 587-598).

Lipid Metabolism.

Seventeen of the differentially expressed proteins in chagasic plasma, i.e., AFM, C4BPA, CACNA1D, DLGAP2, GC, KNG1, MUG1, MYLPF, MY05A, MY05B, PRPH, PZP, RAI14, and SCG2, were allotted to the lipid metabolism/molecular transport/small molecule biochemistry category (Table V) and functionally linked by IPA network analysis to lipid, fatty acid, and carbohydrate metabolism. A majority of the proteins in this category, i.e., ALB, APOA1, APOA4, APOE, APOH, C3, GC, GNAQ, MY05A, PLG, SCD2, SERPINA1, SERPINC1 and VIM, were linked to the synthesis, metabolism, transport, and modification of lipids and fatty acids, and to uptake and release or efflux of lipids, eicosanoids, and cholesterol. PBN/BZ-treated/infected rats exhibited normalization in the expression of 13 of the proteins linked to lipid/fatty acid metabolism (Tables IVa-IVb). These data provide the first indication that lipid/fatty acid metabolism is dysregulated and of pathologic significance in Chagas disease. The observation of increased expression of CEP350 in chagasic rat plasma provides clues to the pathologic mechanism involved in altered lipid/fatty acid metabolism during Chagas disease. CEP350 is a large centrosome-associated protein with a CAP-Gly domain typically found in cytoskeleton-associated proteins (Yan et al., (2006) *Mol Biol Cell,* 17, 634-44; Patel et al., (2005) *J Cell Sci,* 118, 175-86). CEP350 interacts with other centrosomal proteins (e.g. FGFR1) and has been implicated in the mechanisms underlying microtubule anchoring and organization at the centrosome (Yan et al., (2006) *Mol Biol Cell,* 17, 634-44). Interestingly, CEP350 is also shown to alter the activity and sub-cellular compartmentalization of members of the peroxisome proliferator-activated receptors family (PPARα, PPARβ/δ, and PPARγ) (Patel et al., (2005) *J Cell Sci,* 118, 175-86) that heterodimerize with retinoid X receptors (RXRs) to function as transcription factors, and play essential roles in the regulation of cell differentiation and lipid/fatty acid metabolism (Qi et al., (2000) *Cell Biochem Biophys,* 32 Spring, 187-204; Szatmari et al., (2007) *Blood,* 110, 3271-80). Besides CEP350, SERPINs and GPT that were up regulated in chagasic plasma and function in inflammatory response/tissue remodeling and amino acid metabolism, respectively, also belong to the network of proteins regulated by PPARs (Carter and Church, (2009) *PPAR Res,* 2009, 345320; Rakhshandehroo et al., (2010) *PPAR Res,* 2010).

Cardiovascular disease-associated proteins. Twenty-four of the differentially expressed proteins, i.e., AFM, ALB, APOA1, APOA4, APOE, APOH, C3, CFB, CFH, FGB, GC, GNAQ, GSN, HPX, ITIH4, KNG1, MY05A, PLG, SCD2, SCG2, SERPINA1, SERPINC1, SERPINF1, and VIM, were linked to cardiovascular function, skeletal and muscular disorders, and cardiovascular diseases (Table V). Of these, nine proteins (APOA1, APOE, APOH, C3, KNG1, PLG, SCG2, SERPINC1, and SERPINF1) play a functional role in the proliferation of endothelial cells, while several others correlate with angiogenesis (APOE, APOH, PLG, SCG2, SERPINC1, and SERPINF1), thrombosis or thromboembolism (APOE, APOH, CFB, GNAQ, PLG, and SERPINC1), myocardial ischemia and infarction (ALB, C3, FGB, GSN, PLG, APOA1, APOE, PLG, and SERPINC1), and atherosclerosis (APOA1, APOA4, APOE, and PLG) (Diez et al., (2010) *Mol Biosyst,* 6, 289-304). The latter findings indicate that endothelial cell dysfunction plays a role in the progression of Chagas disease and demonstrate that the plasma proteome profile is a useful indicator of clinical disease status.

Biomarkers of Chagas Disease.

An objective of the studies described below was to identify the diagnostic biomarkers of Chagas disease. Western blot analysis using antibodies specific to GSN, MYL2, and VIM validated the 2D-GE plasma profile of chagasic rats and demonstrated that GSN, MYL2, and VIM are indeed increased in the plasma of chagasic rats. There was a direct correlation in plasma levels of GSN, MYL2, and VIM and disease severity in human chagasic patients. Further, PBN/BZ-mediated control of cardiac pathology and preservation of heart contractile function in chagasic rats (Wen et al., (2006) *Am J Pathol,* 169, 1953-64; Wen et al., (2010) *J Am Coll Cardiol,* 55, 2499-508) was associated with normalized plasma levels of GSN, MYL2, and VIM similar to that noted in normal controls. These findings indicate GSN, MYL2, and VIM can be used as protein biomarkers of Chagas disease.

Pathologic Significance of GSN, MYL2, and VIM in Cardiovascular Diseases.

Besides their importance as diagnostic markers in Chagas disease observed herein, GSN, MYL2, and VIM play a significant role in heart disease. GSN is an actin-binding protein, and a member of the gelsolin/villin superfamily (Silacci et al., (2004) *Cell Mol Life Sci,* 61, 2614-23), located intracellularly (cytosol, mitochondria) and extracellularly (blood, plasma) (Koya et al., (2000) *J Biol Chem,* 275, 15343-49). It is a key regulator of actin filament assembly and disassembly and is involved in maintaining cell structure and motility (Silacci et al., (2004) *Cell Mol Life Sci,* 61, 2614-23). Increased GSN expression is associated with interstitial fibrosis and inflammation (Oikonomou et al., (2009) *Thorax,* 64, 467-75), likely due to the GSN-mediated destabilization of cytoskeleton and increased movement of platelets and immune infiltrate, and $GSN^{-/-}$ mice are shown to develop decreased pulmonary fibrosis and inflammation (Oikonomou et al., (2009) *Thorax,* 64, 467-75). In the heart, GSN catalyzes the disassembly and degradation of myocardial proteins (Yang et al., (2000) *Circulation,* 102, 3046-52), and its increased expression is detected in failing human hearts (Yang et al., (2000) *Circulation,* 102, 3046-52). It has been suggested that GSN interacts with hypoxia inducible factor 1 (HIF1A), a master transcriptional regulator of the cellular and systemic responses to hypoxia, that is known to play an essential role in the pathophysiology of ischemic cardiovascular disease (Richard et al., (2003) *Circulation,* 107, 2227-32).

MYL2 (myosin regulatory light chain 2) is a cardiac-specific protein. MYL2 dimerizes with cardiac myosin beta (or slow) heavy chain, and its phosphorylation by $Ca^+$ triggers cardiac contractions. Mutations in MYL2 or abnormalities in MYL2 expression are associated with cardiomyopathy (Richard et al., (2003) *Circulation,* 107, 2227-32), heart failure (Poetter et al., (1996) *Nat Genet,* 13, 63-69), and left ventricular hypertrophy and familial hypertrophy (Flavigny et al., (1998) *J Mol Med,* 76, 208-14; Kabaeva et al., (2002) *Eur J Hum Genet,* 10, 741-48). Expression of MYL2 is altered in chagasic hearts (Cunha-Neto et al., (2005) *Am J Pathol,* 167, 305-13) and isolated cardiomyocytes infected by *T. cruzi* (Goldenberg et al., (2009) *Microbes Infect,* 11, 1140-49), and it is suggested that *T. cruzi*-induced immunoglobulin G autoantibodies and delayed type hypersensitivity to cardiac myosin contribute to disease pathogenesis (Leon and Engman, (2001) *Int J Parasitol,* 31, 555-61; Leon et al., (2004) *Infect Immun,* 72, 3410-17). Certain aspects of the described studies provide the first evidence that the plasma release of MYL2 is linked to disease severity in chagasic patients and indicative of the extent of cardiac muscle injury during Chagas disease development.

VIM is a member of the intermediate filament network, and it is primarily expressed by mesenchymal cells and found in connective tissue. Along with microtubules and actin microfilaments, VIM plays an important role in maintaining cell shape, integrity of the cytoplasm, and stabilizing cytoskeletal interactions (Katsumoto et al., (1990) *Biol Cell*, 68, 139-46). Vimentin is also shown to be localized in the carotid artery and heart valves and serves as a target antigen of peripheral and heart-infiltrating T cells during valvular disease (Fae et al., (2008) *J Autoimmun*, 31, 136-41). Increased detection of vimentin in the heart is indicative of a fibrotic process, as infiltrating fibroblasts replace damaged cardiomyocytes in disease conditions and has been identified by proteomic inventory of myocardial proteins in patients with Chagas disease (Teixeira et al., (2006) *Braz J Med Biol Res*, 39, 1549-62). Results obtained through IPA analysis indicated that VIM modulates NOS2 and is indirectly linked to IL-1β and TNF-α expression in the disease state.

It is demonstrated herein that depletion of high-abundance plasma proteins enhanced the protein discovery of low-abundance proteins by 2D-GE. Pathological events, i.e., persistent inflammation and oxidative stress, associated with Chagas heart disease, and the beneficial effects of antioxidant and anti-parasite therapies in preserving the cardiac function, were reflected in the plasma protein profile of experimentally infected rodents. These proteomic studies provide the first indication that lipid/fatty acid metabolism is dysregulated and of pathologic significance in Chagas disease. Importantly, protein biomarkers (GSN, MYL2, VIM, MYH11, VCL, and PLG) were identified that have utility in diagnosing the presence or severity of Chagas disease, and/or identifying the patients at risk of developing clinical symptoms of Chagas disease.

Certain embodiments are directed to methods of detecting Chagas disease in a biological sample, comprising the step of measuring the presence of at least one protein selected from the group consisting of GSN, MYL2, VIM, MYH11, VCL, and PLG in said sample, wherein elevated levels of GSN, MYL2, VIM, MYH11, VCL, and PLG is indicative of Chagas disease in the subject from which the sample was obtained. Generally, the biological sample is a diagnostic sample from a human or non-human animal. Representative samples include but are not limited to a tissue sample, a plasma sample, or a blood sample. Generally, GSN, MYL2, VIM, MYH11, VCL, and PLG may be detected by any assay known to one of ordinary skill in this art. Representative assays include but are not limited to a Western blot assay, an ELISA assay, an immunofluorescence assay, an immunoprecipitation assay, and a radioimmunoassay. Preferably, the assay determines the concentration of GSN, MYL2, VIM, MYH11, VCL, or PLG in said sample to be ≥50% greater than normal controls. Normal controls are mammals not having cardiac disease or are not at risk of developing heart failure due to chagasic or other etiologies.

In yet another embodiment of the present invention, there is provided a serodiagnostic kit for determining the presence and/or severity of Chagas disease, said kit comprising: (a) the antibody directed against GSN, MYL2, VIM, MYH11, VCL, and/or PLG, wherein the antibody is linked to a reporter molecule; (b) a buffer; and, (c) a reagent for detection of the reporter molecule. Useful antibodies directed against GSN, MYL2, VIM, MYH11, VCL, and PLG are well known to those with ordinary skill in this art. Representative reporter molecules include but are not limited to luciferase, horseradish peroxidase, P-galactosidase, and fluorescent labels.

TABLE IVa

List of Genes/Proteins Differentially Expressed in Response to *T. Cruzi* Infection

| Spot# | Gene Name | Protein Name | Accession No. | Putative Biological Function | Putative Cellular Location |
|---|---|---|---|---|---|
| 12, 180 | KRT1 | Keratin, type II | gi/120474989 | Oxidative stress response | Membrane |
| 34 | TTC37 | KIAA0372 gene product | gi/149058911 | Protein binding | N/A |
| 37, 593 | SRPRB | Bal-667 | gi/33086638 | Iron homeostasis | Extracellular |
| 49, 673 | IGH-1_ | Igh-1a protein | gi/299352 | Antigen binding | Extracellular |
| 52, 54, 302 | TF | Transferrin | gi/1854476 | Transport | Extracellular |
| 53, 225 | SroTP | Serotransferrin | gi/61556986 | Proteolysis | Membrane |
| 72 | IDH3A | Isocitrate dehydrogenase 3a | gi/149041700 | Metabolism | Mitochondria |
| 73, 705, 787 | ALB | Alpha-1-inhibitor 3 | gi/83816939 | Inflammatory response | Extracellular |
| 77 | MUG1 | Murinoglobulin-1 | gi/12831225 | Acute-phase response | Extracellular |
| 88 | IGHG-_ | g-2a immunoglobulin heavy chain | gi/1220486 | Antigen binding | N/A |
| 94 | FGB | Fibrinogen beta chain | gi/124106312 | Signal transduction | Membrane |
| 106 | CDK5RAP2 | CDK5 regulatory associated protein 2 | gi/109476582 | tRNA modification | Cytoplasm |
| 115, 123 | SERPINAL1 | Alpha-1-antiproteinase | gi/112889 | Acute phase response | Extracellular |
| 149 | PUS1 | Pseudouridine synthase 1 | gi/149063707 | tRNA processing | Mitochondria |
| 153 | MYL2 | Myosin, light polypeptide 2 | gi/149067749 | Muscle contraction | Cytosol |
| 177 | AIM | Alpha-1-macroglobulin precursor | gi/21955142 | Protein binding | Extracellular |
| 181 | SERPINA3L | Serine protease inhibitor A3L | gi/2507387 | Inhibitory protein | Extracellular |
| 184, 257, 328 | CFH | Complement inhibitory factor H | gi/l5485713 | Immune response | Cytoplasm |
| 207, 555 | CCHL1A1 | Calcium channel alpha-1 subunit | gi/1184038 | Transport | Membrane |
| 215 | GPT | Glutamic pyruvic transaminase 1 | gi/149066073 | Gluconeogenesis | Cytoplasm |
| 266 | CEP350 | Centrosome-associated protein 350 | gi/18027304 | Cytoskeleton | Cytoplasm |

TABLE IVa-continued

List of Genes/Proteins Differentially Expressed in Response to *T. Cruzi* Infection

| Spot# | Gene Name | Protein Name | Accession No. | Putative Biological Function | Putative Cellular Location |
|---|---|---|---|---|---|
| 299 | UMPS | Uridine monophosphate synthetase | gi/149060638 | Metabolism | Cytoplasm |
| 315 | ITIH4 | Inter-alpha-inhibitor H4 heavy chain | gi/126722991 | Metabolism | Extracellular |
| 334 | ZNF689 | Zinc finger, HIT type 6 | gi/157818873 | Transcription | Nucleus |
| 341 | Nmag_2782 | Na7Ca$^+$ antiporter | gi/8825638 | Transport | Membrane |
| 355, 359 | PLG | Plasminogen | gi/16758216 | Tissue remodeling | Extracellular |
| 382, 385, 378, 572, 578, 595 | CFB | Complement factor B | gi|49027999 | Immune response | Extracellular |
| 389 | GSN | Gelsolin | gi/149038928 | Cytoskeleton | Cytosol |
| 430 | SCD2 | Stearyl-CoA desaturase 2 | gi/1763027 | Fatty acid synthesis | Membrane |
| 434, 678 | COG1 | Component of golgi complex 1 | gi/149054700 | Transport | Membrane |
| 439 | C4BPA | C4b-binding protein alpha | gi/2493792 | Innate immunity | Extracellular |
| 452 | AFM | Afamin, Albumin-binding | gi/60688254 | Transport | Extracellular |
| 464 | IGH-6 | Immunoglobulin heavy chain 6 | gi/62201965 | Antigen binding | N/A |
| 479 | IGHM | Ig mu chain C region | gi/111977 | Immune response | Membrane |
| 493 | ZFP637 | Zinc finger protein 637 | gi/201027426 | Protein binding | Intracellular |
| 515 | CES1C/ES2 | Carboxylesterase | gi/468766 | Metabolism | Endoplasmic reticulum |
| 524 | ERCC4 | DNA repair endonuclease XPF like | gi/109487684 | DNA repair | Nucleus |
| 551, 587, 908 | C3 | Complement C3 | gi/158138561 | Inflammation | Extracellular |
| 559 | HPX | Hemopexin | gi/122065203 | Heme scavenging | Extracellular |
| 571 | GC | Group specific component | gi/51260133 | Vitamin D binding | Extracellular |
| 576, 620 | Ac2-248 | SERPIN-like protein | gi/32527753 | Inflammation response | Extracellular |
| 586, 614 | SERPINC1 | Serine/cysteine peptidase inhibitor | gi/58865630 | Blood clotting | Extracellular |
| 592 | DNASE1L1 | Deoxyribonuclease 1-like | gi/149029874 | DNA catabolism | Endoplasmic reticulum |
| 604 | APOH | Beta-2-glycoprotein 1 | gi/57528174 | Transport | Cell surface |
| 606 | GC | Vitamin D binding protein | gi/203927 | Transport | Extracellular |
| 627 | MAP1 | LMW T-kininogen I | gi/205085 | Acute-phase response | Extracellular |
| 638 | LOC501738 | Immune activating receptor | gi/264681503 | Receptor activity | N/A |
| 649 | SYNE2 | Nesprin-2 like | gi/109478368 | Cytoskeleton | Nuclear |
| 651 | DSTN | Destrin | gi/75991707 | Actin binding | Cytoplasm |
| 655 | DLGAP2 | Disks large-associated protein 2 | gi/16758774 | Synapse transmission | Membrane |
| 672 | SERPINF | Serine/cysteine peptidase inhibitor | gi/29293811 | Inhibitory protein | Extracellular |
| 676 | rCG33447 | Hypothetical | gi/149052919 | N/A | N/A |
| 691 | APOA4 | Apolipoprotein A-IV | gi/114008 | Lipid binding | Extracellular |
| 860 | KRT10 | Keratin, type I | gi/57012436 | Protein binding | Intermediate filament |
| 966 | Hypothetical | CMRF-35-like molecule-7 | gi/109511428 | Immunity | Membrane |
| 897 | MY05A | Myosin Va | gi/149019170 | Myosin complex | Cytoplasm |
| 715 | SERPINA1 | Proteinase inhibitor-like | gi/930263 | Protein binding | Extracellular |
| 724 | ALB | Serum albumin | gi/158138568 | Transport | Extracellular |
| 728 | SYMPK | Symplekin-C | gi/62531221 | Protein binding | Nucleus |
| 733 | DECR2 | 2,4-dienoyl-CoA reductase | gi/25282441 | Metabolism | Peroxisome |
| 740 | PRPH | Peripherin | gi/166063971 | Cytoskeleton | Intermediate filament |
| 745 | PFKFB1 | 6-phosphofructo-2-kinase 1 | gi/77020248 | Metabolism | Cytoplasm |
| 749 | MY05B | Myosin-Vb | gi/8393817 | Myosin complex | Intracellular |
| 766 | SCG2 | Secretogranin 2 | gi/149016236 | Inflammation | Extracellular |
| 779, 909 | VIM | Vimentin | gi/149021116 | Cell integrity | Cytoplasm |
| 796 | Hypothetical p | | gi/109468251 | N/A | N/A |
| 814 | RBM15B | RNA binding motif 15B | gi/109483938 | RNA splicing | Nucleoplasm |
| 817 | BRPF1 | Bromodomain/PHD finger-containing protein 1 | gi/109472470 | Transcription | Cytoplasm |
| 820, 1081 | BFAR | Bifunctional apoptosis regulator | gi/61557021 | Apoptosis | Membrane |
| 827 | GNAT | Guanine binding protein | gi/84662745 | N/A | Cytoplasm |
| 832 | PSMB | Proteasome beta-type subunit RN3 | gi/9653292 | Protein catabolism | Cytoplasm |
| 867 | RAI14 | Ankycorbin | gi/58865464 | N/A | Cytoplasm |
| 881 | CHD4 | Chromodomain helicase DNA binding protein 4 | gi/149049419 | Transcription | Nucleus |
| 900 | rCG25416 | Transferrin region | gi/149018747 | N/A | N/A |
| 906 | APOE | Apolipoprotein E | gi/149056721 | Oxidative stress response | Chylomicron |
| 979 | rCG25357 | | gi/149018900 | N/A | N/A |
| 992 | APOA1 | Apolipoprotein A-I | gi/2145143 | Transport | Membrane |
| 1019 | ZNHIT6 | Hypothetical protein FLJ20729 | gi/149026162 | Protein binding | Pre-snoRNP complex |

TABLE IVb

Differential Expression in Response to *T. Cruzi* Infection

| Spot# | MW (Da) | pI | e-value p < 0.001 | RN* | RA* | RAP* | RC* | RCP* | RCB* | RCPB* |
|---|---|---|---|---|---|---|---|---|---|---|
| 12, 180 | 65059.2 | 8.04 | 9.102E−09 | 4.70 | 4.03 | 21.47 | 9.92 | 7.22 | 9.47 | 11.17 |
| 34 | 68849.3 | 6.22 | 0.001 | 2.29 | 0.64 | 0.37 | 0.31 | 0.45 | 0.37 | 0.25 |
| 37, 593 | 109545.9 | 8.35 | 5.319E−08 | 2.14 | 5.33 | 14.38 | 6.46 | 6.48 | 3.21 | 8.61 |
| 49, 673 | 52500 | 7.23 | 0.132 | 7.89 | 9.90 | 19.12 | 50.91 | 13.39 | 3.98 | 4.48 |
| 52, 54, 302 | 78538.3 | 6.94 | 5.55E−08 | 9.83 | 5.80 | 9.80 | 2.85 | 14.45 | 0.60 | 8.06 |
| 53, 225 | 78512.5 | 7.14 | 1.671E−07 | 6.78 | 6.20 | 8.76 | 2.05 | 15.12 | 1.72 | 5.60 |
| 72 | 30334.3 | 5.83 | 6.694E−07 | 39.31 | 10.26 | 18.10 | 76.03 | 16.43 | 83.09 | 13.00 |
| 73, 705, 787 | 165038.2 | 5.7 | 6.561E−09 | 86.41 | 19.56 | 46.94 | 136.2 | 38.67 | 216.9 | 28.67 |
| 77 | 166589.9 | 5.68 | 0.00007856 | 28.44 | 16.28 | 16.3 | 47.41 | 8.675 | 107.7 | 20.1 |
| 88 | 52242.6 | 8.15 | 1.24E−08 | 2.54 | 1.45 | 74.61 | 38.51 | 40.49 | 4.75 | 17.20 |
| 94 | 54827.9 | 7.9 | 0.0008907 | 0.33 | 0.51 | 1.84 | 1.87 | 2.55 | 0.55 | 0.53 |
| 106 | 208168.7 | 5.27 | 0.001 | 1.47 | 0.85 | 1.70 | 2.22 | 6.94 | 2.21 | 1.67 |
| 115, 123 | 46277.6 | 5.7 | 0.272 | 11.10 | 6.35 | 22.27 | 10.54 | 10.96 | 8.36 | 18.61 |
| 149 | 44463.4 | 8.1 | 0.000911 | 6.34 | 1.67 | 0.78 | 6.50 | 4.39 | 1.16 | 1.17 |
| 153 | 17669.7 | 4.96 | 0.00004491 | 9.21 | 3.03 | 27.07 | 38.86 | 10.34 | 2.37 | 2.66 |
| 177 | 168421.9 | 6.46 | 2.312E−10 | 2.88 | 1.84 | 3.71 | 28.06 | 1.60 | 2.77 | 2.87 |
| 181 | 46419.1 | 5.48 | 0.007 | 1.83 | 3.57 | 3.99 | 17.08 | 1.90 | 7.53 | 3.22 |
| 184, 257, 328 | 144813.9 | 6.52 | 0.001 | 3.69 | 9.51 | 4.54 | 2.46 | 5.85 | 6.15 | 3.32 |
| 207, 555 | 13893.9 | 6.52 | 0.0001206 | 15.79 | 10.78 | 13.23 | 13.97 | 9.12 | 11.32 | 18.65 |
| 215 | 50475.5 | 6.63 | 2.201E−08 | 3.47 | 1.20 | 1.73 | 26.17 | 1.97 | 3.23 | 1.98 |
| 266 | 166809.6 | 8.63 | 0.012 | 0.56 | 0.22 | 0.75 | 0.56 | 0.54 | 1.43 | 1.22 |
| 299 | 33345.2 | 6.02 | 0.00001753 | 2.05 | 1.45 | 1.92 | 0.66 | 1.17 | 1.17 | 2.01 |
| 315 | 103861.8 | 5.82 | 0.00001561 | 1.93 | 2.95 | 6.24 | 7.00 | 8.23 | 5.19 | 3.92 |
| 334 | 53374.8 | 5.51 | 4.73E−08 | 26.07 | 0.59 | 0.61 | 1.00 | 0.71 | 1.05 | 0.45 |
| 341 | 11217.6 | 8.91 | 5.217E−06 | 1.87 | 1.50 | 0.59 | 1.10 | 1.10 | 1.44 | 6.59 |
| 355, 359 | 93213.9 | 6.79 | 0.00001998 | 3.15 | 4.34 | 2.99 | 3.15 | 2.20 | 3.29 | 3.45 |
| 382, 385, 378, 572, 578, 595 | 83735.6 | 6.05 | 1.675E−10 | 5.91 | 43.78 | 33.76 | 30.02 | 3.29 | 23.45 | 5.94 |
| 389 | 86314.2 | 5.76 | 6.661E−14 | 6.51 | 70.05 | 37.55 | 38.06 | 4.32 | 44.17 | 8.39 |
| 430 | 3479.7 | 9.9 | 2.661E−09 | 11.28 | 40.97 | 22.40 | 9.29 | 8.21 | 13.65 | 11.38 |
| 434, 678 | 72098.8 | 8.06 | 1.465E−08 | 29.10 | 110.5 | 55.14 | 34.52 | 24.63 | 43.20 | 30.09 |
| 439 | 64277.8 | 7.06 | 9.889E−09 | 4.21 | 1.72 | 4.04 | 13.64 | 14.99 | 1.36 | 7.56 |
| 452 | 54205.3 | 5.8 | 5.923E−09 | 25.61 | 13.68 | 18.92 | 17.57 | 10.01 | 59.65 | 55.78 |
| 464 | 69059.5 | 5.69 | 0.00004813 | 5.89 | 7.22 | 3.89 | 3.22 | 6.65 | 4.66 | 7.97 |
| 479 | 38189.1 | 6.72 | 1.038E−11 | 2.72 | 21.09 | 23.96 | 10.08 | 32.56 | 8.65 | 14.62 |
| 493 | 31712.4 | 9.5 | 6.464E−07 | 3.75 | 14.49 | 9.82 | 5.45 | 13.46 | 17.41 | 12.88 |
| 515 | 59196.9 | 5.51 | 5.223E−07 | 17.08 | 3.74 | 6.87 | 8.05 | 7.78 | 24.22 | 19.57 |
| 524 | 110025.1 | 9.2 | 9.067E−09 | 120.8 | 32.57 | 53.74 | 55.47 | 21.96 | 68.54 | 30.55 |
| 551, 587, 908 | 187745.9 | 6.06 | 1.64E−11 | 7.046 | 146.9 | 88.04 | 46.76 | 54.1 | 32.88 | 31.97 |
| 559 | 52059.6 | 7.58 | 0.167 | 26.14 | 16.11 | 24.39 | 38.23 | 27.58 | 17.91 | 22.98 |
| 571 | 55079.6 | 5.65 | 9.36E−12 | 37.07 | 11.96 | 7.84 | 74.44 | 38.63 | 3.75 | 24.61 |
| 576, 620 | 67191 | 6.85 | 1.098E−07 | 10.86 | 14.95 | 18.08 | 16.62 | 16.66 | 2.38 | 11.23 |
| 586, 614 | 52714 | 6.18 | 3.838E−06 | 63.42 | 48.70 | 50.44 | 57.02 | 38.00 | 132.20 | 75.38 |
| 592 | 32437 | 6.31 | 1.664E−07 | 21.16 | 20.04 | 15.61 | 12.37 | 31.55 | 11.70 | 17.68 |
| 604 | 39743.2 | 8.58 | 6.515E−06 | 18.54 | 10.78 | 17.48 | 22.81 | 23.66 | 67.12 | 26.76 |
| 606 | 55089.6 | 5.65 | 0.006 | 15.31 | 5.92 | 9.60 | 9.50 | 5.58 | 11.27 | 10.14 |
| 627 | 48757 | 6.29 | 1.263E−07 | 108.9 | 20.28 | 30.23 | 45.81 | 54.85 | 44.92 | 38.20 |
| 638 | 24023.2 | 9.41 | 0.00001901 | 3.11 | 4.73 | 4.42 | 5.82 | 5.92 | 4.69 | 12.14 |
| 649 | 442636.4 | 5.29 | 1.843E−08 | 52.04 | 10.43 | 40.69 | 33.92 | 37.11 | 26.48 | 25.27 |
| 651 | 18806.7 | 8.19 | 3.884E−10 | 23.61 | 109.0 | 94.03 | 176.80 | 57.85 | 37.12 | 51.53 |
| 655 | 111348.9 | 6.82 | 6.158E−10 | 48.96 | 280.6 | 240.6 | 254.70 | 149.20 | 151.30 | 122.60 |
| 672 | 46493.2 | 6.04 | 0.00003611 | 9.02 | 3.59 | 7.34 | 3.45 | 17.65 | 23.29 | 10.52 |
| 676 | 20157.4 | 9.14 | 0.00001667 | 13.09 | 19.5 | 14.69 | 49.61 | 42.59 | 24.67 | 17.95 |
| 691 | 44428.7 | 5.12 | 1.996E−06 | 46.70 | 42.11 | 49.99 | 39.11 | 16.29 | 65.41 | 14.52 |
| 860 | 56698.6 | 5.1 | 4.594E−08 | 6.32 | 2.94 | 3.06 | 3.63 | 5.79 | 2.64 | 20.82 |
| 966 | 9215.8 | 7.93 | 3.917E−09 | 12.66 | 76.58 | 53.33 | 87.53 | 59.29 | 49.99 | 28.90 |
| 897 | 96579.8 | 9.48 | 5.875E−06 | 24.00 | 9.21 | 4.82 | 16.65 | 31.94 | 11.65 | 19.24 |
| 715 | 22867.8 | 6.06 | 2.851E−07 | 6.35 | 12.36 | 10.83 | 24.11 | 32.20 | 30.96 | 12.93 |
| 724 | 70709.9 | 6.09 | 5.902E−07 | 1.19 | 3.31 | 1.72 | 0.46 | 2.23 | 2.19 | 11.17 |
| 728 | 33433.1 | 4.97 | 1.601E−11 | 0.84 | 1.00 | 0.76 | 0.49 | 1.13 | 2.21 | 7.89 |
| 733 | 31614.4 | 8.51 | 0.0006324 | 1.71 | 1.90 | 2.24 | 2.06 | 2.44 | 1.67 | 7.42 |
| 740 | 54063.5 | 5.32 | 0.0001771 | 14.90 | 5.56 | 7.81 | 4.46 | 7.33 | 4.02 | 13.03 |
| 745 | 55301 | 6.78 | 3.474E−08 | 8.56 | 4.94 | 4.51 | 4.17 | 3.21 | 2.30 | 8.93 |
| 749 | 215240.6 | 6.53 | 6.828E−10 | 5.53 | 9.51 | 4.71 | 2.88 | 1.70 | 2.46 | 19.91 |
| 766 | 61578.7 | 4.69 | 0.000699 | 3.94 | 5.60 | 3.20 | 3.16 | 6.32 | 3.79 | 14.46 |
| 779, 909 | 4131.2 | 9.75 | 2.984E−09 | 1.52 | 6.85 | 5.45 | 36.40 | 6.88 | 3.08 | 7.28 |
| 796 | 53156.7 | 8.32 | 1.702E−07 | 10.25 | 8.42 | 9.97 | 7.48 | 8.33 | 5.11 | 11.64 |
| 814 | 96223.1 | 9.85 | 4.256E−07 | 1.65 | 1.41 | 0.60 | 0.63 | 1.56 | 3.61 | 13.27 |
| 817 | 151416.4 | 8.55 | 0.024 | 10.16 | 21.83 | 12.14 | 8.66 | 29.59 | 25.15 | 31.35 |
| 820, 1081 | 53617.2 | 6.44 | 0.006 | 4.77 | 3.19 | 4.59 | 31.17 | 2.20 | 13.38 | 5.61 |
| 827 | 42416.4 | 5.48 | 4.658E−09 | 11.89 | 15.94 | 17.91 | 3.82 | 17.80 | 10.78 | 12.84 |
| 832 | 15426.5 | 6.82 | 0.014 | 2.47 | 3.16 | 6.23 | 1.86 | 7.55 | 3.47 | 8.94 |
| 867 | 106502 | 5.64 | 0.0002925 | 4.34 | 5.72 | 2.56 | 2.86 | 3.00 | 2.41 | 12.07 |
| 881 | 111042 | 5.43 | 2.167E−10 | 11.78 | 5.61 | 13.92 | 17.58 | 6.68 | 28.89 | 8.62 |
| 900 | 66991.6 | 6.41 | 9.426E−08 | 20.46 | 9.26 | 25.94 | 22.29 | 44.00 | 7.06 | 18.89 |

TABLE IVb-continued

Differential Expression in Response to *T. Cruzi* Infection

| Spot# | MW (Da) | pI | e-value p < 0.001 | RN* | RA* | RAP* | RC* | RCP* | RCB* | RCPB* |
|---|---|---|---|---|---|---|---|---|---|---|
| 906 | 27354.1 | 7.93 | 0.004 | 43.97 | 56.73 | 49.40 | 26.45 | 87.74 | 74.42 | 57.50 |
| 979 | 3285.6 | 9.5 | 2.003E−07 | 20.05 | 55.99 | 59.46 | 45.31 | 41.38 | 31.72 | 31.72 |
| 992 | 29869.1 | 5.51 | 8.784E−07 | 15.55 | 41.44 | 34.51 | 32.12 | 57.94 | 38.11 | 39.05 |

N/A: No match available in public information databases,
pI: Isoelectric pH,
MW: molecular weight
*Average Normalized Density × 100,000

TABLE V

IPA network analysis of differentially expressed plasma proteins in Chagasic rats

| ID | Molecules in Network | Score | Focus Molecules | Top Functions |
|---|---|---|---|---|
| 1 | Actin, ALB, APOA1, APOA4, APOE, APOH, C3, CFB, CFH, CFHR1, CFP, CHD4, Cytokeratin, DSTN, FGB, Fibrinogen, GSN, HPX, IgG, KRT1, KRT3, KRT4, KRT10, KRT12, KRT13, KRT23, KRT6B, PLG, SERPINF, SERPINF1, SETX, TF, TMPRSS6, TRY6, VIM | 41 | 19 | Antigen Presentation, Humoral Immune Response, Inflammatory Response |
| 2 | AFM, APP, BRPF3, C4BPA, CACNA1D, COL25A1, DLGAP2, GAB1/2, GC, GRB2, heparin, INSR, KCNMA1, KNG1 (includes EG: 16644), Met dimer, MUG1, MYLPF, MY05A, MY05B, MY05C, PFKFB2, PIK3AP1, PIK3R1, PLA2G2D, PLA2G2E, PRPH, PZP, RAI14, SCG2, SERPINC1, SLC23A1, SNX8, VPS13A, YWHAZ, ZNF32 | 36 | 17 | Lipid Metabolism, Molecular Transport, Small Molecule Biochemistry |
| 3 | ATG4C.BFAR, C10RF25, CASP8, CEBPB, CEP350, CIDEC, CRAT, DSCR3, ESR1, GNAQ, GPT, HNF4A, IDH3A, ITIH4, LGMN, MINA, MYC, PEPD, PPARG, PUS1, PUS3, SCD2, SERPINA1, SLC25A19, SQRDL (includes EG:58472), SRPRB, SYMPK, TMEM176A, TMEM176B, TRUB2, TTC37, UMPS, YME1L1, ZNHIT6 | 29 | 14 | Cellular Development, Free Radical Scavenging, Molecular Transport |

I. Biomarkers

Biomarkers can be used to both define a disease state as well as to provide a means to predict physiological and clinical manifestations of a disease. Three commonly discussed ways in which biomarkers can be used clinically are: (1) to characterize a disease state, i.e. establish a diagnosis, (2) to demonstrate the progression of a disease, and (3) to predict the progression of a disease, i.e. establish a prognosis. Establishing putative biomarkers for such uses typically requires a statistical analysis of relative changes in biomarker expression either cross-sectionally and/or over time (longitudinally). For example, in a state or diagnostic biomarker analysis, levels of one or more biomarkers are measured cross-sectionally, e.g. in patients with disease and in normal control subjects, at one point in time and then related to the clinical status of the groups. Statistically significant differences in biomarker expression can be linked to presence or absence of disease, and would indicate that the biomarkers could subsequently be used to diagnose patients as either having disease or not having disease. In a progression analysis, levels of one or more biomarkers and clinical status are both measured longitudinally. Statistically significant changes over time in both biomarker expression and clinical status would indicate that the biomarkers under study could be used to monitor the progression of the disease. In a prognostic analysis, levels of one or more biomarkers are measured at one point in time and related to the change in clinical status from that point in time to another subsequent point in time. A statistical relationship between biomarker expression and subsequent change in clinical status would indicate that the biomarkers under study could be used to predict disease progression.

Results from prognostic analyses can also be used for disease staging and for monitoring the effects of drugs. The prediction of variable rates of decline for various groups of patients allows them to be identified as subgroups that are differentiated according to disease severity (i.e. less versus more) or stage (i.e. early versus late). Also, patients treated with a putative disease-modifying therapy may demonstrate an observed rate of decline that does not match the rate of decline predicted by the prognostic analysis. This could be considered evidence of drug or treatment efficacy.

II. Computer Implementation

Embodiments of assays described herein or the analysis thereof may be implemented or executed by one or more computer systems. One such computer system is illustrated in FIG. 12. In various embodiments, computer system may be a server, a mainframe computer system, a workstation, a network computer, a desktop computer, a laptop, or the like. For example, in some cases, the analysis described herein or the like may be implemented as a computer system. Moreover, one or more of servers or devices may include one or more computers or computing devices generally in the form of a computer system. In different embodiments these various computer systems may be configured to communicate with each other in any suitable way, such as, for example, via a network.

As illustrated, the computer system includes one or more processors 510 coupled to a system memory 520 via an input/output (I/O) interface 530. Computer system 500 further includes a network interface 540 coupled to I/O interface 530, and one or more input/output devices 550, such as cursor control device 560, keyboard 570, and display(s) 580. In some embodiments, a given entity (e.g., analysis of subjects for trypanosome infection and/or cardiomyopathy) may be implemented using a single instance of computer system 500, while in other embodiments multiple such systems, or multiple nodes making up computer system 500, may be configured to host different portions or instances of embodiments. For example, in an embodiment some elements may be implemented via one or more nodes of computer system 500 that are distinct from those nodes implementing other elements (e.g., a first computer system may implement an assessment of a hybrid latent variable assessment or system while another computer system may implement data gathering, scaling, classification etc.).

In various embodiments, computer system 500 may be a single-processor system including one processor 510, or a multi-processor system including two or more processors 510 (e.g., two, four, eight, or another suitable number). Processors 510 may be any processor capable of executing program instructions. For example, in various embodiments, processors 510 may be general-purpose or embedded processors implementing any of a variety of instruction set architectures (ISAs), such as the x86, POWERPC®, ARM®, SPARC®, or MIPS® ISAs, or any other suitable ISA. In multi-processor systems, each of processors 510 may commonly, but not necessarily, implement the same ISA. Also, in some embodiments, at least one processor 510 may be a graphics-processing unit (GPU) or other dedicated graphics-rendering device.

System memory 520 may be configured to store program instructions and/or data accessible by processor 510. In various embodiments, system memory 520 may be implemented using any suitable memory technology, such as static random access memory (SRAM), synchronous dynamic RAM (SDRAM), nonvolatile/Flash-type memory, or any other type of memory. As illustrated, program instructions and data implementing certain operations, such as, for example, those described herein, may be stored within system memory 520 as program instructions 525 and data storage 535, respectively. In other embodiments, program instructions and/or data may be received, sent or stored upon different types of computer-accessible media or on similar media separate from system memory 520 or computer system 500. Generally speaking, a computer-accessible medium may include any tangible storage media or memory media such as magnetic or optical media—e.g., disk or CD/DVD-ROM coupled to computer system 500 via I/O interface 530. Program instructions and data stored on a tangible computer-accessible medium in non-transitory form may further be transmitted by transmission media or signals such as electrical, electromagnetic, or digital signals, which may be conveyed via a communication medium such as a network and/or a wireless link, such as may be implemented via network interface 540.

In an embodiment, I/O interface 530 may be configured to coordinate I/O traffic between processor 510, system memory 520, and any peripheral devices in the device, including network interface 540 or other peripheral interfaces, such as input/output devices 550. In some embodiments, I/O interface 530 may perform any necessary protocol, timing or other data transformations to convert data signals from one component (e.g., system memory 520) into a format suitable for use by another component (e.g., processor 510). In some embodiments, I/O interface 530 may include support for devices attached through various types of peripheral buses, such as a variant of the Peripheral Component Interconnect (PCI) bus standard or the Universal Serial Bus (USB) standard, for example. In some embodiments, the function of I/O interface 530 may be split into two or more separate components, such as a north bridge and a south bridge, for example. In addition, in some embodiments some or all of the functionality of I/O interface 530, such as an interface to system memory 520, may be incorporated directly into processor 510.

Network interface 540 may be configured to allow data to be exchanged between computer system 500 and other devices attached to a network, such as other computer systems, or between nodes of computer system 500. In various embodiments, network interface 540 may support communication via wired or wireless general data networks, such as any suitable type of Ethernet network, for example; via telecommunications/telephony networks such as analog voice networks or digital fiber communications networks; via storage area networks such as Fiber Channel SANs, or via any other suitable type of network and/or protocol.

Input/output devices 550 may, in some embodiments, include one or more display terminals, keyboards, keypads, touch screens, scanning devices, voice or optical recognition devices, or any other devices suitable for entering or retrieving data by one or more computer system 500. Multiple input/output devices 550 may be present in computer system 500 or may be distributed on various nodes of computer system 500. In some embodiments, similar input/output devices may be separate from computer system 500 and may interact with one or more nodes of computer system 500 through a wired or wireless connection, such as over network interface 540.

Figure 14:
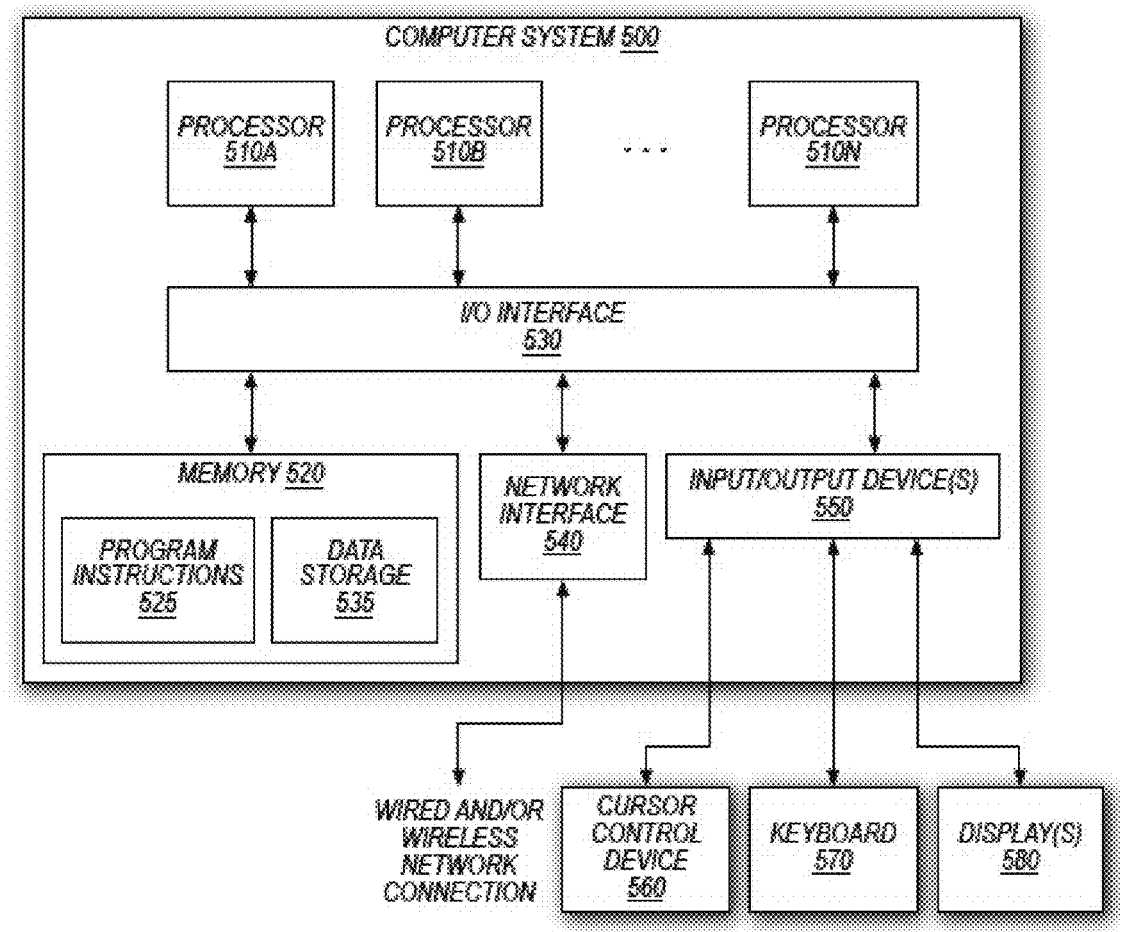
FIG. 14. Illustration of computer implementation.

As shown in FIG. 14, memory 520 may include program instructions 525, configured to implement certain embodiments described herein, and data storage 535, comprising various data accessible by program instructions 525. In an embodiment, program instructions 525 may include software elements of embodiments illustrated herein. For example, program instructions 525 may be implemented in various embodiments using any desired programming language, scripting language, or combination of programming languages and/or scripting languages (e.g., C, C++, C#, JAVA®, JAVASCRIPT®, PERL®, etc). Data storage 535 may include data that may be used in these embodiments. In other embodiments, other or different software elements and data may be included.

A person of ordinary skill in the art will appreciate that computer system 500 is merely illustrative and is not intended to limit the scope of the disclosure described herein. In particular, the computer system and devices may include any combination of hardware or software that can perform the indicated operations. In addition, the operations performed by the illustrated components may, in some embodiments, be performed by fewer components or distributed across additional components. Similarly, in other embodiments, the operations of some of the illustrated components may not be performed and/or other additional operations may be available. Accordingly, systems and methods described herein may be implemented or executed with other computer system configurations.

The invention claimed is:

1. A method of detecting Chagas disease related cardiomyopathy (CCM) in a subject having Chagas disease comprising:
   (a) obtaining a blood sample from the subject; and
   (b) detecting risk for Chagas disease related cardiomyopathy by
      (i) measuring protein levels and cysteinyl-S-nitrosylation (SNO) levels of actin (cytoplasmic isoforms 1 or 2), keratin type II, POTE Ankyrin domain family member E, Ras-related protein Rap1B, serum albumin, or SH3 domain binding glutamic acid-rich-like protein 3 in the blood sample from the subject and
      (ii) calculating a ratio of an SNO ratio to a protein abundance ratio for the proteins, wherein (1) the SNO ratio is the SNO level in the sample over the SNO level in a control and (2) protein abundance ratio is the abundance of the proteins detected after treatment of the sample to remove SNO groups over the protein level in a control after treatment of the control to remove SNO groups,
   wherein the ratio of an SNO ratio to a protein abundance ratio for the proteins is an indicator of Chagas disease related cardiomyopathy.

2. The method of claim 1, wherein protein levels are determined by image analysis of two-dimensional gels.

3. The method of claim 1, wherein the level of cysteinyl-S-nitrosylation (SNO) is measured by saturation fluorescence labeling.

4. A method of treating a patient at risk of chagasic cardiomyopathy comprising:
   administering a treatment for cardiomyopathy to a patient identified as being at risk for Chagas disease related cardiomyopathy using the method of claim 1.

5. The method of claim 4, wherein the patient is an asymptomatic patient.

* * * * *

SEQUENCE LISTING

<160> NUMBER OF SEQ ID NOS: 32

<210> SEQ ID NO 1
<211> LENGTH: 1134
<212> TYPE: PRT
<213> ORGANISM: Homo sapien

<400> SEQUENCE: 1

```
Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
        195                 200                 205

Met Lys Ile Phe Val Thr Thr Lys Asn Ser Lys Asn Gln Gly Ile Glu
    210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
                245                 250                 255

Ala Trp Ala Ser Lys Asp Thr Glu Ala Met Lys Arg Ala Leu Ala Ser
            260                 265                 270

Ile Asp Ser Lys Leu Asn Gln Ala Lys Gly Trp Leu Arg Asp Pro Ser
        275                 280                 285

Ala Ser Pro Gly Asp Ala Gly Glu Gln Ala Ile Arg Gln Ile Leu Asp
    290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
                325                 330                 335

Asp Leu Arg Ala Arg Gly Gln Gly Ser Ser Pro Val Ala Met Gln Lys
            340                 345                 350

Ala Gln Gln Val Ser Gln Gly Leu Asp Val Leu Thr Ala Lys Val Glu
        355                 360                 365
```

```
Asn Ala Ala Arg Lys Leu Glu Ala Met Thr Asn Ser Lys Gln Ser Ile
370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
                405                 410                 415

Lys Ile Ala Glu Leu Cys Asp Asp Pro Lys Glu Arg Asp Asp Ile Leu
                420                 425                 430

Arg Ser Leu Gly Glu Ile Ser Ala Leu Thr Ser Lys Leu Ala Asp Leu
                435                 440                 445

Arg Arg Gln Gly Lys Gly Asp Ser Pro Glu Ala Arg Ala Leu Ala Lys
450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
                485                 490                 495

Ile Glu Gln Ala Gln Arg Trp Ile Asp Asn Pro Thr Val Asp Asp Arg
                500                 505                 510

Gly Val Gly Gln Ala Ala Ile Arg Gly Leu Val Ala Glu Gly His Arg
                515                 520                 525

Leu Ala Asn Val Met Met Gly Pro Tyr Arg Gln Asp Leu Leu Ala Lys
530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
                565                 570                 575

Gln Asp Ser Leu Lys Asp Leu Lys Ala Arg Met Gln Glu Ala Met Thr
                580                 585                 590

Gln Glu Val Ser Asp Val Phe Ser Asp Thr Thr Thr Pro Ile Lys Leu
                595                 600                 605

Leu Ala Val Ala Ala Thr Ala Pro Pro Asp Ala Pro Asn Arg Glu Glu
610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Ala Val Gly Thr Ala Asn Lys Ser
                645                 650                 655

Thr Val Glu Gly Ile Gln Ala Ser Val Lys Thr Ala Arg Glu Leu Thr
                660                 665                 670

Pro Gln Val Val Ser Ala Ala Arg Ile Leu Leu Arg Asn Pro Gly Asn
                675                 680                 685

Gln Ala Ala Tyr Glu His Phe Glu Thr Met Lys Asn Gln Trp Ile Asp
690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
                725                 730                 735

Cys Lys Val Ala Met Ala Asn Ile Gln Pro Gln Met Leu Val Ala Gly
                740                 745                 750

Ala Thr Ser Ile Ala Arg Arg Ala Asn Arg Ile Leu Leu Val Ala Lys
                755                 760                 765

Arg Glu Val Glu Asn Ser Glu Asp Pro Lys Phe Arg Glu Ala Val Lys
                770                 775                 780

Ala Ala Ser Asp Glu Leu Ser Lys Thr Ile Ser Pro Met Val Met Asp
```

```
                785                 790                 795                 800
Ala Lys Ala Val Ala Gly Asn Ile Ser Asp Pro Gly Leu Gln Lys Ser
                    805                 810                 815

Phe Leu Asp Ser Gly Tyr Arg Ile Leu Gly Ala Val Ala Lys Val Arg
                820                 825                 830

Glu Ala Phe Gln Pro Gln Glu Pro Asp Phe Pro Pro Pro Pro Pro Asp
            835                 840                 845

Leu Glu Gln Leu Arg Leu Thr Asp Glu Leu Ala Pro Pro Lys Pro Pro
        850                 855                 860

Leu Pro Glu Gly Glu Val Pro Pro Arg Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
            900                 905                 910

Ser Ser Lys Pro Gly Ile Pro Ala Ala Glu Val Gly Ile Gly Val Val
        915                 920                 925

Ala Glu Ala Asp Ala Ala Asp Ala Ala Gly Phe Pro Val Pro Pro Asp
930                 935                 940

Met Glu Asp Asp Tyr Glu Pro Glu Leu Leu Leu Met Pro Ser Asn Gln
945                 950                 955                 960

Pro Val Asn Gln Pro Ile Leu Ala Ala Ala Gln Ser Leu His Arg Glu
                965                 970                 975

Ala Thr Lys Trp Ser Ser Lys Gly Asn Asp Ile Ile Ala Ala Ala Lys
            980                 985                 990

Arg Met Ala Leu Leu Met Ala Glu Met Ser Arg Leu Val Arg Gly Gly
        995                 1000                1005

Ser Gly Thr Lys Arg Ala Leu Ile Gln Cys Ala Lys Asp Ile Ala
    1010                1015                1020

Lys Ala Ser Asp Glu Val Thr Arg Leu Ala Lys Glu Val Ala Lys
    1025                1030                1035

Gln Cys Thr Asp Lys Arg Ile Arg Thr Asn Leu Leu Gln Val Cys
    1040                1045                1050

Glu Arg Ile Pro Thr Ile Ser Thr Gln Leu Lys Ile Leu Ser Thr
    1055                1060                1065

Val Lys Ala Thr Met Leu Gly Arg Thr Asn Ile Ser Asp Glu Glu
    1070                1075                1080

Ser Glu Gln Ala Thr Glu Met Leu Val His Asn Ala Gln Asn Leu
    1085                1090                1095

Met Gln Ser Val Lys Glu Thr Val Arg Glu Ala Glu Ala Ala Ser
    1100                1105                1110

Ile Lys Ile Arg Thr Asp Ala Gly Phe Thr Leu Arg Trp Val Arg
    1115                1120                1125

Lys Thr Pro Trp Tyr Gln
    1130

<210> SEQ ID NO 2
<211> LENGTH: 454
<212> TYPE: PRT
<213> ORGANISM: Homo sapien
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2
```

-continued

```
Xaa Phe Ser Lys Phe Arg Tyr Leu Tyr Glu Ile Ala Arg Arg His Pro
1               5                   10                  15

Tyr Phe Tyr Ala Pro Glu Leu Leu Phe Phe Ala Lys Arg Tyr Lys Ala
                20                  25                  30

Ala Phe Thr Glu Cys Cys Gln Ala Ala Asp Lys Ala Ala Cys Leu Leu
            35                  40                  45

Pro Lys Leu Asp Glu Leu Arg Asp Glu Gly Lys Ala Ser Ser Ala Lys
        50                  55                  60

Gln Arg Leu Lys Cys Ala Ser Leu Gln Lys Phe Gly Glu Arg Ala Phe
65                  70                  75                  80

Lys Ala Trp Ala Val Ala Arg Leu Ser Gln Arg Phe Pro Lys Ala Glu
                85                  90                  95

Phe Ala Glu Val Ser Lys Leu Val Thr Asp Leu Thr Lys Val His Thr
                100                 105                 110

Glu Cys Cys His Gly Asp Leu Leu Glu Cys Ala Asp Asp Arg Ala Asp
            115                 120                 125

Leu Ala Lys Tyr Ile Cys Glu Asn Gln Asp Ser Ile Ser Ser Lys Leu
        130                 135                 140

Lys Glu Cys Cys Glu Lys Pro Leu Leu Glu Lys Ser His Cys Ile Ala
145                 150                 155                 160

Glu Val Glu Asn Asp Glu Met Pro Ala Asp Leu Pro Ser Leu Ala Ala
                165                 170                 175

Asp Phe Val Glu Ser Lys Asp Val Cys Lys Asn Tyr Ala Glu Ala Lys
                180                 185                 190

Asp Val Phe Leu Gly Met Phe Leu Tyr Glu Tyr Ala Arg Arg His Pro
            195                 200                 205

Asp Tyr Ser Val Val Leu Leu Leu Arg Leu Ala Lys Thr Tyr Glu Thr
        210                 215                 220

Thr Leu Glu Lys Cys Cys Ala Ala Ala Asp Pro His Glu Cys Tyr Ala
225                 230                 235                 240

Lys Val Phe Asp Glu Phe Lys Pro Leu Val Glu Glu Pro Gln Asn Leu
                245                 250                 255

Ile Lys Gln Asn Cys Glu Leu Phe Glu Gln Leu Gly Glu Tyr Lys Phe
            260                 265                 270

Gln Asn Ala Leu Leu Val Arg Tyr Thr Lys Lys Val Pro Gln Val Ser
        275                 280                 285

Thr Pro Thr Leu Val Glu Val Ser Arg Asn Leu Gly Lys Val Gly Ser
        290                 295                 300

Lys Cys Cys Lys His Pro Glu Ala Lys Arg Met Pro Cys Ala Glu Asp
305                 310                 315                 320

Tyr Leu Ser Val Val Leu Asn Gln Leu Cys Val Leu His Glu Lys Thr
                325                 330                 335

Pro Val Ser Asp Arg Val Thr Lys Cys Cys Thr Glu Ser Leu Val Asn
            340                 345                 350

Arg Arg Pro Cys Phe Ser Ala Leu Glu Val Asp Glu Thr Tyr Val Pro
        355                 360                 365

Lys Glu Phe Asn Ala Glu Thr Phe Thr Phe His Ala Asp Ile Cys Thr
        370                 375                 380

Leu Ser Glu Lys Glu Arg Gln Ile Lys Lys Gln Thr Ala Leu Val Glu
385                 390                 395                 400

Leu Val Lys His Lys Pro Lys Ala Thr Lys Glu Gln Leu Lys Ala Val
                405                 410                 415
```

```
Met Asp Asp Phe Ala Ala Phe Val Glu Lys Cys Cys Lys Ala Asp Asp
                420                 425                 430

Lys Glu Thr Cys Phe Ala Glu Glu Gly Lys Lys Leu Val Ala Ala Ser
            435                 440                 445

Gln Ala Ala Leu Gly Leu
        450

<210> SEQ ID NO 3
<211> LENGTH: 1039
<212> TYPE: PRT
<213> ORGANISM: Homo sapien

<400> SEQUENCE: 3

Met Ala Arg Ala Leu Cys Pro Leu Gln Ala Leu Trp Leu Leu Glu Trp
1               5                   10                  15

Val Leu Leu Leu Leu Gly Pro Cys Ala Ala Pro Pro Ala Trp Ala Leu
                20                  25                  30

Asn Leu Asp Pro Val Gln Leu Thr Phe Tyr Ala Gly Pro Asn Gly Ser
            35                  40                  45

Gln Phe Gly Phe Ser Leu Asp Phe His Lys Asp Ser His Gly Arg Val
        50                  55                  60

Ala Ile Val Val Gly Ala Pro Arg Thr Leu Gly Pro Ser Gln Glu Glu
65                  70                  75                  80

Thr Gly Gly Val Phe Leu Cys Pro Trp Arg Ala Glu Gly Gly Gln Cys
                85                  90                  95

Pro Ser Leu Leu Phe Asp Leu Arg Asp Glu Thr Arg Asn Val Gly Ser
            100                 105                 110

Gln Thr Leu Gln Thr Phe Lys Ala Arg Gln Gly Leu Gly Ala Ser Val
        115                 120                 125

Val Ser Trp Ser Asp Val Ile Val Ala Cys Ala Pro Trp Gln His Trp
130                 135                 140

Asn Val Leu Glu Lys Thr Glu Glu Ala Glu Lys Thr Pro Val Gly Ser
145                 150                 155                 160

Cys Phe Leu Ala Gln Pro Glu Ser Gly Arg Arg Ala Glu Tyr Ser Pro
                165                 170                 175

Cys Arg Gly Asn Thr Leu Ser Arg Ile Tyr Val Glu Asn Asp Phe Ser
            180                 185                 190

Trp Asp Lys Arg Tyr Cys Glu Ala Gly Phe Ser Ser Val Val Thr Gln
        195                 200                 205

Ala Gly Glu Leu Val Leu Gly Ala Pro Gly Gly Tyr Tyr Phe Leu Gly
210                 215                 220

Leu Leu Ala Gln Ala Pro Val Ala Asp Ile Phe Ser Ser Tyr Arg Pro
225                 230                 235                 240

Gly Ile Leu Leu Trp His Val Ser Ser Gln Ser Leu Ser Phe Asp Ser
                245                 250                 255

Ser Asn Pro Glu Tyr Phe Asp Gly Tyr Trp Gly Tyr Ser Val Ala Val
            260                 265                 270

Gly Glu Phe Asp Gly Asp Leu Asn Thr Thr Glu Tyr Val Val Gly Ala
        275                 280                 285

Pro Thr Trp Ser Trp Thr Leu Gly Ala Val Glu Ile Leu Asp Ser Tyr
290                 295                 300

Tyr Gln Arg Leu His Arg Leu Arg Gly Glu Gln Met Ala Ser Tyr Phe
305                 310                 315                 320

Gly His Ser Val Ala Val Thr Asp Val Asn Gly Asp Gly Arg His Asp
                325                 330                 335
```

```
Leu Leu Val Gly Ala Pro Leu Tyr Met Glu Ser Arg Ala Asp Arg Lys
            340                 345                 350

Leu Ala Glu Val Gly Arg Val Tyr Leu Phe Leu Gln Pro Arg Gly Pro
            355                 360                 365

His Ala Leu Gly Ala Pro Ser Leu Leu Leu Thr Gly Thr Gln Leu Tyr
            370                 375                 380

Gly Arg Phe Gly Ser Ala Ile Ala Pro Leu Gly Asp Leu Asp Arg Asp
385                 390                 395                 400

Gly Tyr Asn Asp Ile Ala Val Ala Ala Pro Tyr Gly Gly Pro Ser Gly
                405                 410                 415

Arg Gly Gln Val Leu Val Phe Leu Gly Gln Ser Glu Gly Leu Arg Ser
            420                 425                 430

Arg Pro Ser Gln Val Leu Asp Ser Pro Phe Pro Thr Gly Ser Ala Phe
            435                 440                 445

Gly Phe Ser Leu Arg Gly Ala Val Asp Ile Asp Asp Asn Gly Tyr Pro
450                 455                 460

Asp Leu Ile Val Gly Ala Tyr Gly Ala Asn Gln Val Ala Val Tyr Arg
465                 470                 475                 480

Ala Gln Pro Val Val Lys Ala Ser Val Gln Leu Leu Val Gln Asp Ser
            485                 490                 495

Leu Asn Pro Ala Val Lys Ser Cys Val Leu Pro Gln Thr Lys Thr Pro
            500                 505                 510

Val Ser Cys Phe Asn Ile Gln Met Cys Val Gly Ala Thr Gly His Asn
            515                 520                 525

Ile Pro Gln Lys Leu Ser Leu Asn Ala Glu Leu Gln Leu Asp Arg Gln
            530                 535                 540

Lys Pro Arg Gln Gly Arg Arg Val Leu Leu Leu Gly Ser Gln Gln Ala
545                 550                 555                 560

Gly Thr Thr Leu Asn Leu Asp Leu Gly Gly Lys His Ser Pro Ile Cys
                565                 570                 575

His Thr Thr Met Ala Phe Leu Arg Asp Glu Ala Asp Phe Arg Asp Lys
            580                 585                 590

Leu Ser Pro Ile Val Leu Ser Leu Asn Val Ser Leu Pro Pro Thr Glu
            595                 600                 605

Ala Gly Met Ala Pro Ala Val Val Leu His Gly Asp Thr His Val Gln
            610                 615                 620

Glu Gln Thr Arg Ile Val Leu Asp Cys Gly Glu Asp Val Cys Val
625                 630                 635                 640

Pro Gln Leu Gln Leu Thr Ala Ser Val Thr Gly Ser Pro Leu Leu Val
            645                 650                 655

Gly Ala Asp Asn Val Leu Glu Leu Gln Met Asp Ala Ala Asn Glu Gly
                660                 665                 670

Glu Gly Ala Tyr Glu Ala Glu Leu Ala Val His Leu Pro Gln Gly Ala
            675                 680                 685

His Tyr Met Arg Ala Leu Ser Asn Val Glu Gly Phe Glu Arg Leu Ile
            690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
            740                 745                 750
```

-continued

```
Gln Ile Arg Ser Lys Asn Ser Gln Asn Pro Asn Ser Lys Ile Val Leu
        755                 760                 765

Leu Asp Val Pro Val Arg Ala Glu Ala Gln Val Glu Leu Arg Gly Asn
770                 775                 780

Ser Phe Pro Ala Ser Leu Val Val Ala Ala Glu Glu Gly Arg Glu
785                 790                 795                 800

Gln Asn Ser Leu Asp Ser Trp Gly Pro Lys Val Glu His Thr Tyr Glu
                805                 810                 815

Leu His Asn Asn Gly Pro Gly Thr Val Asn Gly Leu His Leu Ser Ile
                820                 825                 830

His Leu Pro Gly Gln Ser Gln Pro Ser Asp Leu Leu Tyr Ile Leu Asp
                835                 840                 845

Ile Gln Pro Gln Gly Gly Leu Gln Cys Phe Pro Gln Pro Val Asn
    850                 855                 860

Pro Leu Lys Val Asp Trp Gly Leu Pro Ile Pro Ser Pro Ser Pro Ile
865                 870                 875                 880

His Pro Ala His His Lys Arg Asp Arg Gln Ile Phe Leu Pro Glu
                885                 890                 895

Pro Glu Gln Pro Ser Arg Leu Gln Asp Pro Val Leu Val Ser Cys Asp
                900                 905                 910

Ser Ala Pro Cys Thr Val Val Gln Cys Asp Leu Gln Glu Met Ala Arg
                915                 920                 925

Gly Gln Arg Ala Met Val Thr Val Leu Ala Phe Leu Trp Leu Pro Ser
            930                 935                 940

Leu Tyr Gln Arg Pro Leu Asp Gln Phe Val Leu Gln Ser His Ala Trp
945                 950                 955                 960

Phe Asn Val Ser Ser Leu Pro Tyr Ala Val Pro Pro Leu Ser Leu Pro
                965                 970                 975

Arg Gly Glu Ala Gln Val Trp Thr Gln Leu Leu Arg Ala Leu Glu Glu
            980                 985                 990

Arg Ala Ile Pro Ile Trp Trp Val  Leu Val Gly Val Leu  Gly Gly Leu
            995                 1000                1005

Leu Leu  Leu Thr Ile Leu Val  Leu Ala Met Trp Lys  Val Gly Phe
    1010                1015                1020

Phe Lys  Arg Asn Arg Pro Pro  Leu Glu Glu Asp  Glu Glu Gly
    1025                1030                1035

Glu

<210> SEQ ID NO 4
<211> LENGTH: 745
<212> TYPE: PRT
<213> ORGANISM: Homo sapien

<400> SEQUENCE: 4

Met Gly Val Pro Phe Phe Ser Ser Leu Arg Cys Met Val Asp Leu Gly
1               5                   10                  15

Pro Cys Trp Ala Gly Gly Leu Thr Ala Glu Met Lys Leu Leu Leu Ala
            20                  25                  30

Leu Ala Gly Leu Leu Ala Ile Leu Ala Thr Pro Gln Pro Ser Glu Gly
        35                  40                  45

Ala Ala Pro Ala Val Leu Gly Glu Val Asp Thr Ser Leu Val Leu Ser
    50                  55                  60

Ser Met Glu Glu Ala Lys Gln Leu Val Asp Lys Ala Tyr Lys Glu Arg
65                  70                  75                  80
```

-continued

```
Arg Glu Ser Ile Lys Gln Arg Leu Arg Ser Gly Ala Ser Pro Met
                 85                  90                  95
Glu Leu Leu Ser Tyr Phe Lys Gln Pro Val Ala Ala Thr Arg Thr Ala
            100                 105                 110
Val Arg Ala Ala Asp Tyr Leu His Val Ala Leu Asp Leu Leu Glu Arg
            115                 120                 125
Lys Leu Arg Ser Leu Trp Arg Arg Pro Phe Asn Val Thr Asp Val Leu
130             135                 140
Thr Pro Ala Gln Leu Asn Val Leu Ser Lys Ser Ser Gly Cys Ala Tyr
145                 150                 155                 160
Gln Asp Val Gly Val Thr Cys Pro Glu Gln Asp Lys Tyr Arg Thr Ile
                165                 170                 175
Thr Gly Met Cys Asn Asn Arg Arg Ser Pro Thr Leu Gly Ala Ser Asn
                180                 185                 190
Arg Ala Phe Val Arg Trp Leu Pro Ala Glu Tyr Glu Asp Gly Phe Ser
            195                 200                 205
Leu Pro Tyr Gly Trp Thr Pro Gly Val Lys Arg Asn Gly Phe Pro Val
210                 215                 220
Ala Leu Ala Arg Ala Val Ser Asn Glu Ile Val Arg Phe Pro Thr Asp
225                 230                 235                 240
Gln Leu Thr Pro Asp Gln Glu Arg Ser Leu Met Phe Met Gln Trp Gly
                245                 250                 255
Gln Leu Leu Asp His Asp Leu Asp Phe Thr Pro Glu Pro Ala Ala Arg
                260                 265                 270
Ala Ser Phe Val Thr Gly Val Asn Cys Glu Thr Ser Cys Val Gln Gln
            275                 280                 285
Pro Pro Cys Phe Pro Leu Lys Ile Pro Pro Asn Asp Pro Arg Ile Lys
290                 295                 300
Asn Gln Ala Asp Cys Ile Pro Phe Phe Arg Ser Cys Pro Ala Cys Pro
305                 310                 315                 320
Gly Ser Asn Ile Thr Ile Arg Asn Gln Ile Asn Ala Leu Thr Ser Phe
                325                 330                 335
Val Asp Ala Ser Met Val Tyr Gly Ser Glu Glu Pro Leu Ala Arg Asn
            340                 345                 350
Leu Arg Asn Met Ser Asn Gln Leu Gly Leu Leu Ala Val Asn Gln Arg
            355                 360                 365
Phe Gln Asp Asn Gly Arg Ala Leu Leu Pro Phe Asp Asn Leu His Asp
370                 375                 380
Asp Pro Cys Leu Leu Thr Asn Arg Ser Ala Arg Ile Pro Cys Phe Leu
385                 390                 395                 400
Ala Gly Asp Thr Arg Ser Ser Glu Met Pro Glu Leu Thr Ser Met His
                405                 410                 415
Thr Leu Leu Leu Arg Glu His Asn Arg Leu Ala Thr Glu Leu Lys Ser
            420                 425                 430
Leu Asn Pro Arg Trp Asp Gly Glu Arg Leu Tyr Gln Glu Ala Arg Lys
            435                 440                 445
Ile Val Gly Ala Met Val Gln Ile Ile Thr Tyr Arg Asp Tyr Leu Pro
450                 455                 460
Leu Val Leu Gly Pro Thr Ala Met Arg Lys Tyr Leu Pro Thr Tyr Arg
465                 470                 475                 480
Ser Tyr Asn Asp Ser Val Asp Pro Arg Ile Ala Asn Val Phe Thr Asn
                485                 490                 495
Ala Phe Arg Tyr Gly His Thr Leu Ile Gln Pro Phe Met Phe Arg Leu
```

```
                500                 505                 510
Asp Asn Arg Tyr Gln Pro Met Glu Pro Asn Pro Arg Val Pro Leu Ser
            515                 520                 525

Arg Val Phe Ala Ser Trp Arg Val Val Leu Glu Gly Gly Ile Asp
        530                 535                 540

Pro Ile Leu Arg Gly Leu Met Ala Thr Pro Ala Lys Leu Asn Arg Gln
545                 550                 555                 560

Asn Gln Ile Ala Val Asp Glu Ile Arg Glu Arg Leu Phe Glu Gln Val
                565                 570                 575

Met Arg Ile Gly Leu Asp Leu Pro Ala Leu Asn Met Gln Arg Ser Arg
            580                 585                 590

Asp His Gly Leu Pro Gly Tyr Asn Ala Trp Arg Arg Phe Cys Gly Leu
        595                 600                 605

Pro Gln Pro Glu Thr Val Gly Gln Leu Gly Thr Val Leu Arg Asn Leu
    610                 615                 620

Lys Leu Ala Arg Lys Leu Met Glu Gln Tyr Gly Thr Pro Asn Asn Ile
625                 630                 635                 640

Asp Ile Trp Met Gly Gly Val Ser Glu Pro Leu Lys Arg Lys Gly Arg
                645                 650                 655

Val Gly Pro Leu Leu Ala Cys Ile Ile Gly Thr Gln Phe Arg Lys Leu
            660                 665                 670

Arg Asp Gly Asp Arg Phe Trp Trp Glu Asn Glu Gly Val Phe Ser Met
        675                 680                 685

Gln Gln Arg Gln Ala Leu Ala Gln Ile Ser Leu Pro Arg Ile Ile Cys
    690                 695                 700

Asp Asn Thr Gly Ile Thr Thr Val Ser Lys Asn Asn Ile Phe Met Ser
705                 710                 715                 720

Asn Ser Tyr Pro Arg Asp Phe Val Asn Cys Ser Thr Leu Pro Ala Leu
                725                 730                 735

Asn Leu Ala Ser Trp Arg Glu Ala Ser
            740                 745

<210> SEQ ID NO 5
<211> LENGTH: 374
<212> TYPE: PRT
<213> ORGANISM: Homo sapien

<400> SEQUENCE: 5

Glu Glu Glu Ile Ala Ala Leu Val Ile Asp Asn Gly Ser Gly Met Cys
1               5                   10                  15

Lys Ala Gly Phe Ala Gly Asp Asp Ala Pro Arg Ala Val Phe Pro Ser
            20                  25                  30

Ile Val Gly Arg Pro Arg His Gln Gly Val Met Val Gly Met Gly Gln
        35                  40                  45

Lys Asp Ser Tyr Val Gly Asp Glu Ala Gln Ser Lys Arg Gly Ile Leu
    50                  55                  60

Thr Leu Lys Tyr Pro Ile Glu His Gly Ile Val Thr Asn Trp Asp Asp
65                  70                  75                  80

Met Glu Lys Ile Trp His His Thr Phe Tyr Asn Glu Leu Arg Val Ala
                85                  90                  95

Pro Glu Glu His Pro Val Leu Leu Thr Glu Ala Pro Leu Asn Pro Lys
            100                 105                 110

Ala Asn Arg Glu Lys Met Thr Gln Ile Met Phe Glu Thr Phe Asn Thr
        115                 120                 125
```

```
Pro Ala Met Tyr Val Ala Ile Gln Ala Val Leu Ser Leu Tyr Ala Ser
    130                 135                 140
Gly Arg Thr Thr Gly Ile Val Met Asp Ser Gly Asp Gly Val Thr His
145                 150                 155                 160
Thr Val Pro Ile Tyr Glu Gly Tyr Ala Leu Pro His Ala Ile Leu Arg
                165                 170                 175
Leu Asp Leu Ala Gly Arg Asp Leu Thr Asp Tyr Leu Met Lys Ile Leu
            180                 185                 190
Thr Glu Arg Gly Tyr Ser Phe Thr Thr Thr Ala Glu Arg Glu Ile Val
        195                 200                 205
Arg Asp Ile Lys Glu Lys Leu Cys Tyr Val Ala Leu Asp Phe Glu Gln
210                 215                 220
Glu Met Ala Thr Ala Ala Ser Ser Ser Ser Leu Glu Lys Ser Tyr Glu
225                 230                 235                 240
Leu Pro Asp Gly Gln Val Ile Thr Ile Gly Asn Glu Arg Phe Arg Cys
                245                 250                 255
Pro Glu Ala Leu Phe Gln Pro Ser Phe Leu Gly Met Glu Ser Cys Gly
            260                 265                 270
Ile His Glu Thr Thr Phe Asn Ser Ile Met Lys Cys Asp Val Asp Ile
        275                 280                 285
Arg Lys Asp Leu Tyr Ala Asn Thr Val Leu Ser Gly Gly Thr Thr Met
290                 295                 300
Tyr Pro Gly Ile Ala Asp Arg Met Gln Lys Glu Ile Thr Ala Leu Ala
305                 310                 315                 320
Pro Ser Thr Met Lys Ile Lys Ile Ile Ala Pro Pro Glu Arg Lys Tyr
                325                 330                 335
Ser Val Trp Ile Gly Gly Ser Ile Leu Ala Ser Leu Ser Thr Phe Gln
            340                 345                 350
Gln Met Trp Ile Ser Lys Gln Glu Tyr Asp Glu Ser Gly Pro Ser Ile
        355                 360                 365
Val His Arg Lys Cys Phe
    370

<210> SEQ ID NO 6
<211> LENGTH: 2429
<212> TYPE: PRT
<213> ORGANISM: Homo sapien

<400> SEQUENCE: 6

Met Val Ala Leu Ser Leu Lys Ile Ser Ile Gly Asn Val Val Lys Thr
1               5                   10                  15
Met Gln Phe Glu Pro Ser Thr Met Val Tyr Asp Ala Cys Arg Ile Ile
                20                  25                  30
Arg Glu Arg Ile Pro Glu Ala Pro Ala Gly Pro Pro Ser Asp Phe Gly
            35                  40                  45
Leu Phe Leu Ser Asp Asp Asp Pro Lys Lys Gly Ile Trp Leu Glu Ala
        50                  55                  60
Gly Lys Ala Leu Asp Tyr Tyr Met Leu Arg Asn Gly Asp Thr Met Glu
65                  70                  75                  80
Tyr Arg Lys Lys Gln Arg Pro Leu Lys Ile Arg Met Leu Asp Gly Thr
                85                  90                  95
Val Lys Thr Ile Met Val Asp Asp Ser Lys Thr Val Thr Asp Met Leu
            100                 105                 110
Met Thr Ile Cys Ala Arg Ile Gly Ile Thr Asn His Asp Glu Tyr Ser
        115                 120                 125
```

-continued

```
Leu Val Arg Glu Leu Met Glu Glu Lys Lys Glu Ile Thr Gly Thr
    130                 135                 140
Leu Arg Lys Asp Lys Thr Leu Leu Arg Asp Glu Lys Lys Met Glu Lys
145                 150                 155                 160
Leu Lys Gln Lys Leu His Thr Asp Asp Glu Leu Asn Trp Leu Asp His
                165                 170                 175
Gly Arg Thr Leu Arg Glu Gln Gly Val Glu Glu His Glu Thr Leu Leu
            180                 185                 190
Leu Arg Arg Lys Phe Phe Tyr Ser Asp Gln Asn Val Asp Ser Arg Asp
        195                 200                 205
Pro Val Gln Leu Asn Leu Leu Tyr Val Gln Ala Arg Asp Asp Ile Leu
    210                 215                 220
Asn Gly Ser His Pro Val Ser Phe Asp Lys Ala Cys Glu Phe Ala Gly
225                 230                 235                 240
Phe Gln Cys Gln Ile Gln Phe Gly Pro His Asn Glu Gln Lys His Lys
                245                 250                 255
Ala Gly Phe Leu Asp Leu Lys Asp Phe Leu Pro Lys Glu Tyr Val Lys
            260                 265                 270
Gln Lys Gly Glu Arg Lys Ile Phe Gln Ala His Lys Asn Cys Gly Gln
        275                 280                 285
Met Ser Glu Ile Glu Ala Lys Val Arg Tyr Val Lys Leu Ala Arg Ser
    290                 295                 300
Leu Lys Thr Tyr Gly Val Ser Phe Phe Leu Val Lys Glu Lys Met Lys
305                 310                 315                 320
Gly Lys Asn Lys Leu Val Pro Arg Leu Leu Gly Ile Thr Lys Glu Cys
                325                 330                 335
Val Met Arg Val Asp Glu Lys Thr Lys Glu Val Ile Gln Glu Trp Asn
            340                 345                 350
Leu Thr Asn Ile Lys Arg Trp Ala Ala Ser Pro Lys Ser Phe Thr Leu
        355                 360                 365
Asp Phe Gly Asp Tyr Gln Asp Gly Tyr Tyr Ser Val Gln Thr Thr Glu
    370                 375                 380
Gly Glu Gln Ile Ala Gln Leu Ile Ala Gly Tyr Ile Asp Ile Ile Leu
385                 390                 395                 400
Lys Lys Lys Lys Ser Lys Asp His Phe Gly Leu Glu Gly Asp Glu Glu
                405                 410                 415
Ser Thr Met Leu Glu Asp Ser Val Ser Pro Lys Lys Ser Thr Val Leu
            420                 425                 430
Gln Gln Gln Tyr Asn Arg Val Gly Lys Val Glu His Gly Ser Val Ala
        435                 440                 445
Leu Pro Ala Ile Met Arg Ser Gly Ala Ser Gly Pro Glu Asn Phe Gln
    450                 455                 460
Val Gly Ser Met Pro Pro Ala Gln Gln Gln Ile Thr Ser Gly Gln Met
465                 470                 475                 480
His Arg Gly His Met Pro Pro Leu Thr Ser Ala Gln Gln Ala Leu Thr
                485                 490                 495
Gly Thr Ile Asn Ser Ser Met Gln Ala Val Gln Ala Ala Gln Ala Thr
            500                 505                 510
Leu Asp Asp Phe Asp Thr Leu Pro Pro Leu Gly Gln Asp Ala Ala Ser
        515                 520                 525
Lys Ala Trp Arg Lys Asn Lys Met Asp Glu Ser Lys His Glu Ile His
    530                 535                 540
```

```
Ser Gln Val Asp Ala Ile Thr Ala Gly Thr Ala Ser Val Val Asn Leu
545                 550                 555                 560

Thr Ala Gly Asp Pro Ala Glu Thr Asp Tyr Thr Ala Val Gly Cys Ala
            565                 570                 575

Val Thr Thr Ile Ser Ser Asn Leu Thr Glu Met Ser Arg Gly Val Lys
                580                 585                 590

Leu Leu Ala Ala Leu Leu Glu Asp Glu Gly Ser Gly Arg Pro Leu
        595                 600                 605

Leu Gln Ala Ala Lys Gly Leu Ala Gly Ala Val Ser Glu Leu Leu Arg
610                 615                 620

Ser Ala Gln Pro Ala Ser Ala Glu Pro Arg Gln Asn Leu Leu Gln Ala
625                 630                 635                 640

Ala Gly Asn Val Gly Gln Ala Ser Gly Glu Leu Leu Gln Gln Ile Gly
            645                 650                 655

Glu Ser Asp Thr Asp Pro His Phe Gln Asp Ala Leu Met Gln Leu Ala
                660                 665                 670

Lys Ala Val Ala Ser Ala Ala Ala Leu Val Leu Lys Ala Lys Ser
        675                 680                 685

Val Ala Gln Arg Thr Glu Asp Ser Gly Leu Gln Thr Gln Val Ile Ala
690                 695                 700

Ala Ala Thr Gln Cys Ala Leu Ser Thr Ser Gln Leu Val Ala Cys Thr
705                 710                 715                 720

Lys Val Val Ala Pro Thr Ile Ser Ser Pro Val Cys Gln Glu Gln Leu
                725                 730                 735

Val Glu Ala Gly Arg Leu Val Ala Lys Ala Val Glu Gly Cys Val Ser
            740                 745                 750

Ala Ser Gln Ala Ala Thr Glu Asp Gly Gln Leu Leu Arg Gly Val Gly
            755                 760                 765

Ala Ala Ala Thr Ala Val Thr Gln Ala Leu Asn Glu Leu Leu Gln His
770                 775                 780

Val Lys Ala His Ala Thr Gly Ala Gly Pro Ala Gly Arg Tyr Asp Gln
785                 790                 795                 800

Ala Thr Asp Thr Ile Leu Thr Val Thr Glu Asn Ile Phe Ser Ser Met
                805                 810                 815

Gly Asp Ala Gly Glu Met Val Arg Gln Ala Arg Ile Leu Ala Gln Ala
            820                 825                 830

Thr Ser Asp Leu Val Asn Ala Ile Lys Ala Asp Ala Glu Gly Glu Ser
        835                 840                 845

Asp Leu Glu Asn Ser Arg Lys Leu Leu Ser Ala Lys Ile Leu Ala
850                 855                 860

Asp Ala Thr Ala Lys Met Val Glu Ala Ala Lys Gly Ala Ala Ala His
865                 870                 875                 880

Pro Asp Ser Glu Glu Gln Gln Gln Arg Leu Arg Glu Ala Ala Glu Gly
            885                 890                 895

Leu Arg Met Ala Thr Asn Ala Ala Ala Gln Asn Ala Ile Lys Lys Lys
        900                 905                 910

Leu Val Gln Arg Leu Glu His Ala Ala Lys Gln Ala Ala Ala Ser Ala
            915                 920                 925

Thr Gln Thr Ile Ala Ala Ala Gln His Ala Ala Ser Thr Pro Lys Ala
        930                 935                 940

Ser Ala Gly Pro Gln Pro Leu Leu Val Gln Ser Cys Lys Ala Val Ala
945                 950                 955                 960

Glu Gln Ile Pro Leu Leu Val Gln Gly Val Arg Gly Ser Gln Ala Gln
```

-continued

```
                965                 970                 975
Pro Asp Ser Pro Ser Ala Gln Leu Ala Leu Ile Ala Ala Ser Gln Ser
                    980                 985                 990
Phe Leu Gln Pro Gly Gly Lys Met Val Ala Ala Ala Lys Ala Ser Val
                995                1000                1005
Pro Thr Ile Gln Asp Gln Ala Ser Ala Met Gln Leu Ser Gln Cys
   1010                1015                1020
Ala Lys Asn Leu Gly Thr Ala Leu Ala Glu Leu Arg Thr Ala Ala
   1025                1030                1035
Gln Lys Ala Gln Glu Ala Cys Gly Pro Leu Glu Met Asp Ser Ala
   1040                1045                1050
Leu Ser Val Val Gln Asn Leu Glu Lys Asp Leu Gln Glu Val Lys
   1055                1060                1065
Ala Ala Ala Arg Asp Gly Lys Leu Lys Pro Leu Pro Gly Glu Thr
   1070                1075                1080
Met Glu Lys Cys Thr Gln Asp Leu Gly Asn Ser Thr Lys Ala Val
   1085                1090                1095
Ser Ser Ala Ile Ala Gln Leu Leu Gly Glu Val Ala Gln Gly Asn
   1100                1105                1110
Glu Asn Tyr Ala Gly Ile Ala Ala Arg Asp Val Ala Gly Gly Leu
   1115                1120                1125
Arg Ser Leu Ala Gln Ala Ala Arg Gly Val Ala Ala Leu Thr Ser
   1130                1135                1140
Asp Pro Ala Val Gln Ala Ile Val Leu Asp Thr Ala Ser Asp Val
   1145                1150                1155
Leu Asp Lys Ala Ser Ser Leu Ile Glu Glu Ala Lys Lys Ala Ala
   1160                1165                1170
Gly His Pro Gly Asp Pro Glu Ser Gln Gln Arg Leu Ala Gln Val
   1175                1180                1185
Ala Lys Ala Val Thr Gln Ala Leu Asn Arg Cys Val Ser Cys Leu
   1190                1195                1200
Pro Gly Gln Arg Asp Val Asp Asn Ala Leu Arg Ala Val Gly Asp
   1205                1210                1215
Ala Ser Lys Arg Leu Leu Ser Asp Ser Leu Pro Pro Ser Thr Gly
   1220                1225                1230
Thr Phe Gln Glu Ala Gln Ser Arg Leu Asn Glu Ala Ala Ala Gly
   1235                1240                1245
Leu Asn Gln Ala Ala Thr Glu Leu Val Gln Ala Ser Arg Gly Thr
   1250                1255                1260
Pro Gln Asp Leu Ala Arg Ala Ser Gly Arg Phe Gly Gln Asp Phe
   1265                1270                1275
Ser Thr Phe Leu Glu Ala Gly Val Glu Met Ala Gly Gln Ala Pro
   1280                1285                1290
Ser Gln Glu Asp Arg Ala Gln Val Val Ser Asn Leu Lys Gly Ile
   1295                1300                1305
Ser Met Ser Ser Ser Lys Leu Leu Leu Ala Ala Lys Ala Leu Ser
   1310                1315                1320
Thr Asp Pro Ala Ala Pro Asn Leu Lys Ser Gln Leu Ala Ala Ala
   1325                1330                1335
Ala Arg Ala Val Thr Asp Ser Ile Asn Gln Leu Ile Thr Met Cys
   1340                1345                1350
Thr Gln Gln Ala Pro Gly Gln Lys Glu Cys Asp Asn Ala Leu Arg
   1355                1360                1365
```

```
Glu Leu Glu Thr Val Arg Glu Leu Leu Glu Asn Pro Val Gln Pro
    1370            1375            1380

Ile Asn Asp Met Ser Tyr Phe Gly Cys Leu Asp Ser Val Met Glu
    1385            1390            1395

Asn Ser Lys Val Leu Gly Glu Ala Met Thr Gly Ile Ser Gln Asn
    1400            1405            1410

Ala Lys Asn Gly Asn Leu Pro Glu Phe Gly Asp Ala Ile Ser Thr
    1415            1420            1425

Ala Ser Lys Ala Leu Cys Gly Phe Thr Glu Ala Ala Ala Gln Ala
    1430            1435            1440

Ala Tyr Leu Val Gly Val Ser Asp Pro Asn Ser Gln Ala Gly Gln
    1445            1450            1455

Gln Gly Leu Val Glu Pro Thr Gln Phe Ala Arg Ala Asn Gln Ala
    1460            1465            1470

Ile Gln Met Ala Cys Gln Ser Leu Gly Glu Pro Gly Cys Thr Gln
    1475            1480            1485

Ala Gln Val Leu Ser Ala Ala Thr Ile Val Ala Lys His Thr Ser
    1490            1495            1500

Ala Leu Cys Asn Ser Cys Arg Leu Ala Ser Ala Arg Thr Thr Asn
    1505            1510            1515

Pro Thr Ala Lys Arg Gln Phe Val Gln Ser Ala Lys Glu Val Ala
    1520            1525            1530

Asn Ser Thr Ala Asn Leu Val Lys Thr Ile Lys Ala Leu Asp Gly
    1535            1540            1545

Ala Phe Thr Glu Glu Asn Arg Ala Gln Cys Arg Ala Ala Thr Ala
    1550            1555            1560

Pro Leu Leu Glu Ala Val Asp Asn Leu Ser Ala Phe Ala Ser Asn
    1565            1570            1575

Pro Glu Phe Ser Ser Ile Pro Ala Gln Ile Ser Pro Glu Gly Arg
    1580            1585            1590

Ala Ala Met Glu Pro Ile Val Ile Ser Ala Lys Thr Met Leu Glu
    1595            1600            1605

Ser Ala Gly Gly Leu Ile Gln Thr Ala Arg Ala Leu Ala Val Asn
    1610            1615            1620

Pro Arg Asp Pro Pro Ser Trp Ser Val Leu Ala Gly His Ser Arg
    1625            1630            1635

Thr Val Ser Asp Ser Ile Lys Lys Leu Ile Thr Ser Met Arg Asp
    1640            1645            1650

Lys Ala Pro Gly Gln Leu Glu Cys Glu Thr Ala Ile Ala Ala Leu
    1655            1660            1665

Asn Ser Cys Leu Arg Asp Leu Asp Gln Ala Ser Leu Ala Ala Val
    1670            1675            1680

Ser Gln Gln Leu Ala Pro Leu Gln Glu Ile Ser His Leu Ile Glu
    1685            1690            1695

Pro Leu Ala Asn Ala Ala Arg Ala Glu Ala Ser Gln Leu Gly His
    1700            1705            1710

Lys Val Ser Gln Met Ala Gln Tyr Phe Glu Pro Leu Thr Leu Ala
    1715            1720            1725

Ala Val Gly Ala Ala Ser Lys Thr Leu Ser His Pro Gln Gln Met
    1730            1735            1740

Ala Leu Leu Asp Gln Thr Lys Thr Leu Ala Glu Ser Ala Leu Gln
    1745            1750            1755
```

```
Leu Leu Tyr Thr Ala Lys Glu Ala Gly Gly Asn Pro Lys Leu Asp
    1760                1765                1770

Glu Gly Pro Met Gly Glu Pro Glu Gly Ser Phe Val Asp Tyr Gln
    1775                1780                1785

Thr Thr Met Val Arg Thr Ala Lys Ala Ile Ala Val Thr Val Gln
    1790                1795                1800

Glu Met Ile Gly Ser His Ile Lys His Arg Val Gln Glu Leu Gly
    1805                1810                1815

His Gly Cys Ala Ala Leu Val Thr Lys Ala Gly Ala Leu Gln Cys
    1820                1825                1830

Ser Pro Ser Asp Ala Tyr Thr Lys Lys Glu Leu Ile Glu Cys Ala
    1835                1840                1845

Arg Arg Val Ser Glu Lys Val Ser His Val Leu Ala Ala Leu Gln
    1850                1855                1860

Ala Gly Asn Arg Gly Thr Gln Ala Cys Ile Thr Ala Ala Ser Ala
    1865                1870                1875

Val Ser Gly Ile Ile Ala Asp Leu Asp Thr Thr Ile Met Phe Ala
    1880                1885                1890

Thr Ala Gly Thr Leu Asn Arg Glu Gly Thr Glu Thr Phe Ala Asp
    1895                1900                1905

His Arg Glu Gly Ile Leu Lys Thr Ala Lys Val Leu Val Glu Asp
    1910                1915                1920

Thr Lys Val Leu Val Gln Asn Ala Ala Gly Ser Gln Glu Lys Leu
    1925                1930                1935

Ala Gln Ala Ala Gln Ser Ser Val Ala Thr Ile Thr Arg Leu Ala
    1940                1945                1950

Asp Val Val Lys Leu Gly Ala Ala Ser Leu Gly Ala Glu Asp Pro
    1955                1960                1965

Glu Thr Gln Val Val Leu Ile Asn Ala Val Lys Asp Val Ala Lys
    1970                1975                1980

Ala Leu Gly Asp Leu Ile Ser Ala Thr Lys Ala Ala Ala Gly Lys
    1985                1990                1995

Val Gly Asp Asp Pro Ala Val Trp Gln Leu Lys Asn Ser Ala Lys
    2000                2005                2010

Val Met Val Thr Asn Val Thr Ser Leu Leu Lys Thr Val Lys Ala
    2015                2020                2025

Val Glu Asp Glu Ala Thr Lys Gly Thr Arg Ala Leu Glu Ala Thr
    2030                2035                2040

Thr Glu His Ile Arg Gln Glu Leu Ala Pro Pro Ala Lys Thr Ser
    2045                2050                2055

Thr Pro Glu Asp Phe Ile Arg Met Thr Lys Gly Ile Thr Met Ala
    2060                2065                2070

Thr Ala Lys Ala Val Ala Ala Gly Asn Ser Cys Arg Gln Glu Asp
    2075                2080                2085

Val Ile Ala Thr Ala Asn Leu Ser Arg Arg Ala Ile Ala Asp Met
    2090                2095                2100

Leu Arg Ala Cys Lys Glu Ala Ala Tyr His Pro Glu Val Ala Pro
    2105                2110                2115

Asp Val Arg Leu Arg Ala Leu His Tyr Gly Arg Glu Cys Ala Asn
    2120                2125                2130

Gly Tyr Leu Glu Leu Leu Asp His Val Leu Leu Thr Leu Gln Lys
    2135                2140                2145

Pro Ser Pro Glu Leu Lys Gln Gln Leu Thr Gly His Ser Lys Arg
```

```
            2150                2155                2160

Val Ala Gly Ser Val Thr Glu Leu Ile Gln Ala Ala Glu Ala Met
        2165                2170                2175

Lys Gly Thr Glu Trp Val Asp Pro Glu Asp Pro Thr Val Ile Ala
        2180                2185                2190

Glu Asn Glu Leu Leu Gly Ala Ala Ala Ile Glu Ala Ala Ala
        2195                2200                2205

Lys Lys Leu Glu Gln Leu Lys Pro Arg Ala Lys Pro Lys Glu Ala
        2210                2215                2220

Asp Glu Ser Leu Asn Phe Glu Glu Gln Ile Leu Glu Ala Ala Lys
        2225                2230                2235

Ser Ile Ala Ala Ala Thr Ser Ala Leu Val Lys Ala Ala Ser Ala
        2240                2245                2250

Ala Gln Arg Glu Leu Val Ala Gln Gly Lys Val Gly Ala Ile Pro
        2255                2260                2265

Ala Asn Ala Leu Asp Asp Gly Gln Trp Ser Gln Gly Leu Ile Ser
        2270                2275                2280

Ala Ala Arg Met Val Ala Ala Thr Asn Asn Leu Cys Glu Ala
        2285                2290                2295

Ala Asn Ala Ala Val Gln Gly His Ala Ser Gln Glu Lys Leu Ile
        2300                2305                2310

Ser Ser Ala Lys Gln Val Ala Ala Ser Thr Ala Gln Leu Leu Val
        2315                2320                2325

Ala Cys Lys Val Lys Ala Asp Gln Asp Ser Glu Ala Met Lys Arg
        2330                2335                2340

Leu Gln Ala Ala Gly Asn Ala Val Lys Arg Ala Ser Asp Asn Leu
        2345                2350                2355

Val Lys Ala Ala Gln Lys Ala Ala Ala Phe Glu Glu Gln Glu Asn
        2360                2365                2370

Glu Thr Val Val Val Lys Glu Lys Met Val Gly Gly Ile Ala Gln
        2375                2380                2385

Ile Ile Ala Ala Gln Glu Glu Met Leu Arg Lys Glu Arg Glu Leu
        2390                2395                2400

Glu Glu Ala Arg Lys Lys Leu Ala Gln Ile Arg Gln Gln Gln Tyr
        2405                2410                2415

Lys Phe Leu Pro Ser Glu Leu Arg Asp Glu His
        2420                2425

<210> SEQ ID NO 7
<211> LENGTH: 351
<212> TYPE: PRT
<213> ORGANISM: Homo sapien

<400> SEQUENCE: 7

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
                20                  25                  30

Ser Ile Val Gly Arg Pro Arg His Gln Gly Val Met Val Gly Met Gly
            35                  40                  45

Gln Lys Asp Ser Tyr Val Gly Asp Glu Ala Gln Ser Lys Arg Gly Ile
        50                  55                  60

Leu Thr Leu Lys Tyr Pro Ile Glu His Gly Ile Val Thr Asn Trp Asp
65                  70                  75                  80
```

```
Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Ala Ile Leu Arg Leu Asp Leu Ala Gly Arg Asp
145                 150                 155                 160

Leu Thr Asp Tyr Leu Met Lys Ile Leu Thr Glu Arg Gly Tyr Ser Phe
                165                 170                 175

Thr Thr Thr Ala Glu Arg Glu Ile Val Arg Asp Ile Lys Glu Lys Leu
            180                 185                 190

Cys Tyr Val Ala Leu Asp Phe Glu Gln Glu Met Ala Thr Ala Ala Ser
        195                 200                 205

Ser Ser Ser Leu Glu Lys Ser Tyr Glu Leu Pro Asp Gly Gln Val Ile
    210                 215                 220

Thr Ile Gly Asn Glu Arg Phe Arg Cys Pro Glu Ala Leu Phe Gln Pro
225                 230                 235                 240

Ser Phe Leu Gly Met Glu Ser Cys Gly Ile His Glu Thr Thr Phe Asn
                245                 250                 255

Ser Ile Met Lys Cys Asp Val Asp Ile Arg Lys Asp Leu Tyr Ala Asn
            260                 265                 270

Thr Val Leu Ser Gly Gly Thr Thr Met Tyr Pro Gly Ile Ala Asp Arg
        275                 280                 285

Met Gln Lys Glu Ile Thr Ala Leu Ala Pro Ser Thr Met Lys Ile Lys
    290                 295                 300

Ile Ile Ala Pro Pro Glu Arg Lys Tyr Ser Val Trp Ile Gly Gly Ser
305                 310                 315                 320

Ile Leu Ala Ser Leu Ser Thr Phe Gln Gln Met Trp Ile Ser Lys Gln
                325                 330                 335

Glu Tyr Asp Glu Ser Gly Pro Ser Ile Val His Arg Lys Cys Phe
            340                 345                 350

<210> SEQ ID NO 8
<211> LENGTH: 467
<212> TYPE: PRT
<213> ORGANISM: Homo sapien

<400> SEQUENCE: 8

Met Pro Lys Asp Ser Ala Phe Pro Arg Ala Pro Ala Ala Gly Arg Glu
1               5                   10                  15

Asn Gly Gly Gly Gly Asp Gly Arg Ala Leu Leu Lys Gln Gln Leu Trp
            20                  25                  30

Ser Phe Pro Gln Gly Arg Gly Arg Ser Gly Ser Leu Thr Arg Thr Gly
        35                  40                  45

Phe Arg Val Thr Ala Ser Tyr Cys Ser Cys Cys Ser Thr Arg Gln
    50                  55                  60

Ser Gly Ser Ala Ser Ser Ser Cys Ala Ser Phe Ser Gly Ser Thr Ser
65                  70                  75                  80

Ser Trp Ser Ala Ala Arg Cys Gln Thr Ala Ser Phe Ala Gly Ser Asp
                85                  90                  95

Ala Gly Val Arg Gly Val Ser Glu Leu Gly Leu Ala Arg Gly His Thr
            100                 105                 110
```

Val Thr Thr Ser Cys Val Pro Arg Phe Val Arg Thr Met Cys Ala
            115                 120                 125
Val Leu Gly Leu Val Ala Arg Gln Glu Asp Ser Gly Leu Arg Asp His
    130                 135                 140
Ser Val Arg Val Leu Ile Ser Asn His Val Thr Pro Phe Asp His Asn
145                 150                 155                 160
Ile Val Asn Leu Leu Thr Thr Cys Ser Thr Pro Leu Leu Asn Ser Pro
                165                 170                 175
Pro Ser Phe Val Cys Trp Ser Arg Gly Phe Met Glu Met Asn Gly Arg
            180                 185                 190
Gly Glu Leu Val Glu Ser Leu Lys Arg Phe Cys Ala Ser Thr Arg Leu
    195                 200                 205
Pro Pro Thr Pro Leu Leu Phe Pro Glu Glu Ala Thr Asn Gly
            210                 215                 220
Arg Glu Gly Leu Leu Arg Phe Ser Ser Trp Pro Phe Ser Ile Gln Asp
225                 230                 235                 240
Val Val Gln Pro Leu Thr Leu Gln Val Gln Arg Pro Leu Val Ser Val
                245                 250                 255
Thr Val Ser Asp Ala Ser Trp Val Ser Glu Leu Leu Trp Ser Leu Phe
            260                 265                 270
Val Pro Phe Thr Val Tyr Gln Val Arg Trp Leu Arg Pro Val His Arg
    275                 280                 285
Gln Leu Gly Glu Ala Asn Glu Glu Phe Ala Leu Arg Val Gln Gln Leu
    290                 295                 300
Val Ala Lys Glu Leu Gly Gln Thr Gly Thr Arg Leu Thr Pro Ala Asp
305                 310                 315                 320
Lys Ala Glu His Met Lys Arg Gln Arg His Pro Arg Leu Arg Pro Gln
                325                 330                 335
Ser Ala Gln Ser Ser Phe Pro Pro Ser Pro Gly Pro Ser Pro Asp Val
            340                 345                 350
Gln Leu Ala Thr Leu Ala Gln Arg Val Lys Glu Val Leu Pro His Val
    355                 360                 365
Pro Leu Gly Val Ile Gln Arg Asp Leu Ala Lys Thr Gly Cys Val Asp
    370                 375                 380
Leu Thr Ile Thr Asn Leu Leu Glu Gly Ala Val Ala Phe Met Pro Glu
385                 390                 395                 400
Asp Ile Thr Lys Gly Thr Gln Ser Leu Leu Thr Ala Ser Ala Ser Lys
                405                 410                 415
Phe Pro Ser Ser Gly Pro Val Thr Pro Gln Pro Thr Ala Leu Thr Phe
            420                 425                 430
Ala Lys Ser Ser Trp Ala Arg Gln Glu Ser Leu Gln Glu Arg Lys Gln
    435                 440                 445
Ala Leu Tyr Glu Tyr Ala Arg Arg Arg Phe Thr Glu Arg Arg Ala Gln
    450                 455                 460
Glu Ala Asp
465

<210> SEQ ID NO 9
<211> LENGTH: 1301
<212> TYPE: PRT
<213> ORGANISM: Homo sapien

<400> SEQUENCE: 9

Met Glu Met Val Gly Phe Leu Pro Lys Thr Arg Arg Gln Ile Phe Ser

-continued

```
1               5                   10                  15
Leu Leu Ser Ala Ile Leu His Leu Gly Asn Ile Cys Tyr Lys Lys
                20                  25                  30

Thr Tyr Arg Asp Asp Ser Ile Asp Ile Cys Asn Pro Glu Val Leu Pro
                35                  40                  45

Ile Val Ser Glu Leu Leu Glu Val Lys Glu Met Leu Phe Glu Ala
    50                  55                  60

Leu Val Thr Arg Lys Thr Val Thr Val Gly Lys Leu Ile Leu Pro
65                  70                  75                  80

Tyr Lys Leu Ala Glu Ala Val Thr Val Arg Asn Ser Met Ala Lys Ser
                85                  90                  95

Leu Tyr Ser Ala Leu Phe Asp Trp Ile Val Phe Arg Ile Asn His Ala
                100                 105                 110

Leu Leu Asn Ser Lys Asp Leu Glu His Asn Thr Lys Thr Leu Ser Ile
                115                 120                 125

Gly Val Leu Asp Ile Phe Gly Phe Glu Asp Tyr Glu Asn Asn Ser Phe
130                 135                 140

Glu Gln Phe Cys Ile Asn Phe Ala Asn Glu Arg Leu Gln His Tyr Phe
145                 150                 155                 160

Asn Gln His Ile Phe Lys Leu Glu Gln Glu Glu Tyr Arg Thr Glu Gly
                165                 170                 175

Ile Ser Trp His Asn Ile Asp Tyr Ile Asp Asn Thr Cys Cys Ile Asn
                180                 185                 190

Leu Ile Ser Lys Lys Pro Thr Gly Leu Leu His Leu Leu Asp Glu Glu
                195                 200                 205

Ser Asn Phe Pro Gln Ala Thr Asn Gln Thr Leu Leu Asp Lys Phe Lys
210                 215                 220

His Gln His Glu Asp Asn Ser Tyr Ile Glu Phe Pro Ala Val Met Glu
225                 230                 235                 240

Pro Ala Phe Ile Ile Lys His Tyr Ala Gly Lys Val Lys Tyr Gly Val
                245                 250                 255

Lys Asp Phe Arg Glu Lys Asn Thr Asp His Met Arg Pro Asp Ile Val
                260                 265                 270

Ala Leu Leu Arg Ser Ser Lys Asn Ala Phe Ile Ser Gly Met Ile Gly
                275                 280                 285

Ile Asp Pro Val Ala Val Phe Arg Trp Ala Ile Leu Arg Ala Phe Phe
                290                 295                 300

Arg Ala Met Val Ala Phe Arg Glu Ala Gly Lys Arg Asn Ile His Arg
305                 310                 315                 320

Lys Thr Gly His Asp Asp Thr Ala Pro Cys Ala Ile Leu Lys Ser Met
                325                 330                 335

Asp Ser Phe Ser Phe Leu Gln His Pro Val His Gln Arg Ser Leu Glu
                340                 345                 350

Ile Leu Gln Arg Cys Lys Glu Glu Lys Tyr Ser Lys Ala Thr Asn Pro
                355                 360                 365

Asp Lys Leu Leu Ser His Ile His Leu Glu Met Glu Thr Arg Ser Ile
                370                 375                 380

Leu His Gln Gly Ile Thr Arg Lys Asn Pro Arg Thr Pro Leu Ser Asp
385                 390                 395                 400

Leu Gln Gly Met Asn Ala Leu Asn Glu Lys Asn Gln His Asp Thr Phe
                405                 410                 415

Asp Ile Ala Trp Asn Gly Arg Thr Gly Ile Arg Gln Ser Arg Leu Ser
                420                 425                 430
```

```
Ser Gly Thr Ser Leu Leu Asp Lys Asp Gly Ile Phe Ala Asn Ser Thr
            435                 440                 445
Ser Ser Lys Leu Leu Glu Arg Ala His Gly Ile Leu Thr Arg Asn Lys
        450                 455                 460
Asn Phe Lys Ser Lys Pro Ala Leu Pro Lys His Leu Leu Glu Val Asn
465                 470                 475                 480
Ser Leu Lys His Leu Thr Arg Leu Thr Leu Gln Asp Arg Ile Thr Lys
                485                 490                 495
Ser Leu Leu His Leu His Lys Lys Lys Pro Pro Ser Ile Ser Ala
            500                 505                 510
Gln Phe Gln Ala Ser Leu Ser Lys Leu Met Glu Thr Leu Gly Gln Ala
        515                 520                 525
Glu Pro Tyr Phe Val Lys Cys Ile Arg Ser Asn Ala Glu Lys Leu Pro
            530                 535                 540
Leu Arg Phe Ser Asp Val Leu Val Leu Arg Gln Leu Arg Tyr Thr Gly
545                 550                 555                 560
Met Leu Glu Thr Val Arg Ile Arg Gln Ser Gly Tyr Ser Ser Lys Tyr
                565                 570                 575
Ser Phe Gln Asp Phe Val Ser His Phe His Val Leu Leu Pro Arg Asn
            580                 585                 590
Ile Ile Pro Ser Lys Phe Asn Ile Gln Asp Phe Phe Arg Lys Ile Asn
            595                 600                 605
Leu Asn Pro Asp Asn Tyr Gln Val Gly Lys Thr Met Val Phe Leu Lys
    610                 615                 620
Glu Gln Glu Arg Gln His Leu Gln Asp Leu Leu His Gln Glu Val Leu
625                 630                 635                 640
Arg Arg Ile Ile Leu Leu Gln Arg Trp Phe Arg Val Leu Leu Cys Arg
                645                 650                 655
Gln His Phe Leu His Leu Arg Gln Ala Ser Val Ile Ile Gln Arg Phe
            660                 665                 670
Trp Arg Asn Tyr Leu Asn Gln Lys Gln Val Arg Asp Ala Ala Val Gln
        675                 680                 685
Lys Asp Ala Phe Val Met Ala Ser Ala Ala Leu Leu Gln Ala Ser
    690                 695                 700
Trp Arg Ala His Leu Glu Arg Gln Arg Tyr Leu Glu Leu Arg Ala Ala
705                 710                 715                 720
Ala Ile Val Ile Gln Gln Lys Trp Arg Asp Tyr Tyr Arg Arg His
                725                 730                 735
Met Ala Ala Ile Cys Ile Gln Ala Arg Trp Lys Ala Tyr Arg Glu Ser
            740                 745                 750
Lys Arg Tyr Gln Glu Gln Arg Lys Lys Ile Ile Leu Leu Gln Ser Thr
        755                 760                 765
Cys Arg Gly Phe Arg Ala Arg Gln Arg Phe Lys Ala Leu Lys Glu Gln
    770                 775                 780
Arg Leu Arg Glu Thr Lys Pro Glu Val Gly Leu Val Asn Ile Lys Gly
785                 790                 795                 800
Tyr Gly Ser Leu Glu Ile Gln Gly Ser Asp Pro Ser Gly Trp Glu Asp
                805                 810                 815
Cys Ser Phe Asp Asn Arg Ile Lys Ala Ile Glu Glu Cys Lys Ser Val
            820                 825                 830
Ile Glu Ser Asn Arg Ile Ser Arg Glu Ser Ser Val Asp Cys Leu Lys
            835                 840                 845
```

-continued

```
Glu Ser Pro Asn Lys Gln Gln Glu Arg Ala Gln Ser Gln Ser Gly Val
            850                 855                 860
Asp Leu Gln Glu Asp Val Leu Val Arg Glu Arg Pro Arg Ser Leu Glu
865                 870                 875                 880
Asp Leu His Gln Lys Lys Val Gly Arg Ala Lys Arg Glu Ser Arg Arg
                        885                 890                 895
Met Arg Glu Leu Glu Gln Ala Ile Phe Ser Leu Glu Leu Leu Lys Val
            900                 905                 910
Arg Ser Leu Gly Gly Ile Ser Pro Ser Glu Asp Arg Arg Trp Ser Thr
                915                 920                 925
Glu Leu Val Pro Glu Gly Leu Gln Ser Pro Arg Gly Thr Pro Asp Ser
            930                 935                 940
Glu Ser Ser Gln Gly Ser Leu Glu Leu Leu Ser Tyr Glu Glu Ser Gln
945                 950                 955                 960
Lys Ser Lys Leu Glu Ser Val Ile Ser Asp Glu Gly Asp Leu Gln Phe
                965                 970                 975
Pro Ser Pro Lys Ile Ser Ser Pro Lys Phe Asp Ser Arg Asp Asn
            980                 985                 990
Ala Leu Ser Ala Ser Asn Glu Thr Ser Ser Ala Glu His Leu Lys Asp
            995                 1000                1005
Gly Thr Met Lys Glu Met Val Val Cys Ser Ser Glu Ser Ile Thr
        1010                1015                1020
Cys Lys Pro Gln Leu Lys Asp Ser Phe Ile Ser Asn Ser Leu Pro
        1025                1030                1035
Thr Phe Phe Tyr Ile Pro Gln Gln Asp Pro Leu Lys Thr Asn Ser
        1040                1045                1050
Gln Leu Asp Thr Ser Ile Gln Arg Asn Lys Leu Leu Glu Asn Glu
        1055                1060                1065
Asp Thr Ala Gly Glu Ala Leu Thr Leu Asp Ile Asn Arg Glu Thr
        1070                1075                1080
Arg Arg Tyr His Cys Ser Gly Lys Asp Gln Ile Val Pro Ser Leu
        1085                1090                1095
Asn Thr Glu Ser Ser Asn Pro Val Leu Lys Lys Leu Glu Lys Leu
        1100                1105                1110
Asn Thr Glu Lys Glu Glu Arg Gln Lys Gln Leu Gln Gln Gln Asn
        1115                1120                1125
Glu Lys Glu Met Met Glu Gln Ile Arg Gln Gln Thr Asp Ile Leu
        1130                1135                1140
Glu Lys Glu Arg Lys Ala Phe Lys Thr Ile Glu Lys Pro Arg Ile
        1145                1150                1155
Gly Glu Cys Leu Val Ala Pro Ser Ser Tyr Gln Ser Lys Gln Arg
        1160                1165                1170
Val Glu Arg Pro Ser Ser Leu Leu Ser Leu Asn Thr Ser Asn Lys
        1175                1180                1185
Gly Glu Leu Asn Val Leu Gly Ser Leu Ser Leu Lys Asp Ala Ala
        1190                1195                1200
Leu Ala Gln Lys Asp Ser Ser Ala His Leu Pro Pro Lys Asp
        1205                1210                1215
Arg Pro Val Thr Val Phe Phe Glu Arg Lys Gly Ser Pro Cys Gln
        1220                1225                1230
Ser Ser Thr Val Lys Glu Leu Ser Lys Thr Asp Arg Met Gly Thr
        1235                1240                1245
Gln Leu Asn Val Ala Cys Lys Leu Ser Asn Asn Arg Ile Ser Lys
```

```
                1250               1255              1260
Arg Glu His Phe Arg Pro Thr Gln Ser Tyr Ser His Asn Ser Asp
        1265              1270              1275

Asp Leu Ser Arg Glu Gly Asn Ala Arg Pro Ile Phe Phe Thr Pro
        1280              1285              1290

Lys Asp Asn Met Ser Ile Pro Leu
        1295              1300

<210> SEQ ID NO 10
<211> LENGTH: 165
<212> TYPE: PRT
<213> ORGANISM: Homo sapien

<400> SEQUENCE: 10

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
            165

<210> SEQ ID NO 11
<211> LENGTH: 131
<212> TYPE: PRT
<213> ORGANISM: Homo sapien

<400> SEQUENCE: 11

Met Ser Cys Gln Lys Ala Val Leu Glu Leu Asn Ile Gly Ser Gln Leu
1               5                   10                  15

Gly Pro Lys Ser Pro Glu Arg Thr Glu Gly Val Thr Ala Phe Glu Asp
            20                  25                  30

Tyr Gly Thr Gly Leu Leu Glu Asn Gln Leu Ser Val Gly Asp Phe Val
        35                  40                  45

Lys Ile Gln Lys Ala Phe Glu Asp Gly Asp Ile Trp Leu Thr Glu Gln
    50                  55                  60

His Tyr Glu Trp Leu Lys Thr Arg Gln Lys Leu Gly Leu Leu Thr Trp
65                  70                  75                  80

Met Lys Cys Arg Ser Cys Ile Cys Glu Arg Ala Met Val Leu Gly Thr
                85                  90                  95

Val Pro Thr Ala Lys Glu Asn His Leu Tyr Val Gln Arg Arg Leu His
```

<210> SEQ ID NO 12
<211> LENGTH: 644
<212> TYPE: PRT
<213> ORGANISM: Homo sapien

<400> SEQUENCE: 12

```
Met Ser Arg Gln Phe Ser Ser Arg Ser Gly Tyr Arg Ser Gly Gly Gly
1               5                   10                  15

Phe Ser Ser Gly Ser Ala Gly Ile Ile Asn Tyr Gln Arg Arg Thr Thr
                20                  25                  30

Ser Ser Ser Thr Arg Arg Ser Gly Gly Gly Gly Arg Phe Ser Ser
            35                  40                  45

Cys Gly Gly Gly Gly Ser Phe Gly Ala Gly Gly Phe Gly Ser
50                      55                  60

Arg Ser Leu Val Asn Leu Gly Gly Ser Lys Ser Ile Ser Ile Ser Val
65                  70                  75                  80

Ala Arg Gly Gly Gly Arg Gly Ser Gly Phe Gly Gly Gly Tyr Gly Gly
                85                  90                  95

Gly Gly Phe Gly Gly Gly Phe Gly Gly Gly Phe Gly Gly
                100                 105                 110

Gly Ile Gly Gly Gly Phe Gly Phe Gly Ser Gly Gly Gly
                115                 120                 125

Phe Gly Gly Gly Phe Gly Gly Gly Tyr Gly Gly Gly Tyr Gly
        130                 135                 140

Pro Val Cys Pro Pro Gly Gly Ile Gln Glu Val Thr Ile Asn Gln Ser
145                 150                 155                 160

Leu Leu Gln Pro Leu Asn Val Glu Ile Asp Pro Glu Ile Gln Lys Val
                165                 170                 175

Lys Ser Arg Glu Arg Glu Gln Ile Lys Ser Leu Asn Asn Gln Phe Ala
                180                 185                 190

Ser Phe Ile Asp Lys Val Arg Phe Leu Glu Gln Gln Asn Gln Val Leu
                195                 200                 205

Gln Thr Lys Trp Glu Leu Leu Gln Gln Val Asp Thr Ser Thr Arg Thr
        210                 215                 220

His Asn Leu Glu Pro Tyr Phe Glu Ser Phe Ile Asn Asn Leu Arg Arg
225                 230                 235                 240

Arg Val Asp Gln Leu Lys Ser Asp Gln Ser Arg Leu Asp Ser Glu Leu
                245                 250                 255

Lys Asn Met Gln Asp Met Val Glu Asp Tyr Arg Asn Lys Tyr Glu Asp
                260                 265                 270

Glu Ile Asn Lys Arg Thr Asn Ala Glu Asn Glu Phe Val Thr Ile Lys
                275                 280                 285

Lys Asp Val Asp Gly Ala Tyr Met Thr Lys Val Asp Leu Gln Ala Lys
        290                 295                 300

Leu Asp Asn Leu Gln Gln Glu Ile Asp Phe Leu Thr Ala Leu Tyr Gln
305                 310                 315                 320

Ala Glu Leu Ser Gln Met Gln Thr Gln Ile Ser Glu Thr Asn Val Ile
                325                 330                 335
```

```
Leu Ser Met Asp Asn Asn Arg Ser Leu Asp Leu Asp Ser Ile Ile Ala
                340                 345                 350

Glu Val Lys Ala Gln Tyr Glu Asp Ile Ala Gln Lys Ser Lys Ala Glu
            355                 360                 365

Ala Glu Ser Leu Tyr Gln Ser Lys Tyr Glu Glu Leu Gln Ile Thr Ala
        370                 375                 380

Gly Arg His Gly Asp Ser Val Arg Asn Ser Lys Ile Glu Ile Ser Glu
385                 390                 395                 400

Leu Asn Arg Val Ile Gln Arg Leu Arg Ser Glu Ile Asp Asn Val Lys
                405                 410                 415

Lys Gln Ile Ser Asn Leu Gln Gln Ser Ile Ser Asp Ala Glu Gln Arg
            420                 425                 430

Gly Glu Asn Ala Leu Lys Asp Ala Lys Asn Lys Leu Asn Asp Leu Glu
        435                 440                 445

Asp Ala Leu Gln Gln Ala Lys Glu Asp Leu Ala Arg Leu Leu Arg Asp
    450                 455                 460

Tyr Gln Glu Leu Met Asn Thr Lys Leu Ala Leu Asp Leu Glu Ile Ala
465                 470                 475                 480

Thr Tyr Arg Thr Leu Leu Glu Gly Glu Ser Arg Met Ser Gly Glu
                485                 490                 495

Cys Ala Pro Asn Val Ser Val Ser Val Ser Thr Ser His Thr Thr Ile
            500                 505                 510

Ser Gly Gly Gly Ser Arg Gly Gly Gly Gly Gly Tyr Gly Ser Gly
            515                 520                 525

Gly Ser Ser Tyr Gly Ser Gly Gly Ser Tyr Gly Ser Gly Gly
        530                 535                 540

Gly Gly Gly Gly Arg Gly Ser Tyr Gly Ser Gly Ser Ser Tyr Gly
545                 550                 555                 560

Ser Gly Gly Ser Tyr Gly Ser Gly Gly Gly Gly His Gly
            565                 570                 575

Ser Tyr Gly Ser Gly Ser Ser Gly Gly Tyr Arg Gly Gly Ser Gly
        580                 585                 590

Gly Gly Gly Gly Ser Ser Gly Gly Arg Gly Ser Gly Gly Ser
            595                 600                 605

Ser Gly Gly Ser Ile Gly Gly Arg Gly Ser Ser Ser Gly Gly Val Lys
610                 615                 620

Ser Ser Gly Gly Ser Ser Ser Val Lys Phe Val Ser Thr Thr Tyr Ser
625                 630                 635                 640

Gly Val Thr Arg

<210> SEQ ID NO 13
<211> LENGTH: 53
<212> TYPE: PRT
<213> ORGANISM: Homo sapien

<400> SEQUENCE: 13

Ser Phe Thr Gly Leu Gly Trp Glu Ile Arg Met His Cys Glu Leu Phe
1               5                   10                  15

Phe Asn Ser Phe Gln Gly Phe Phe Val Ser Ile Ile Tyr Cys Tyr Cys
            20                  25                  30

Asn Gly Glu Ile Gly Arg Leu Leu Cys Met Asp Lys Ile Pro Ala Thr
        35                  40                  45

Ala Ser Leu Thr Pro
    50
```

<210> SEQ ID NO 14
<211> LENGTH: 201
<212> TYPE: PRT
<213> ORGANISM: Homo sapien

<400> SEQUENCE: 14

```
Met Glu Tyr Leu Ile Gly Ile Gln Gly Pro Asp Tyr Val Leu Val Ala
1               5                   10                  15

Ser Asp Arg Val Ala Ala Ser Asn Ile Val Gln Met Lys Asp Asp His
            20                  25                  30

Asp Lys Met Phe Lys Met Ser Glu Lys Ile Leu Leu Leu Cys Val Gly
        35                  40                  45

Glu Ala Gly Asp Thr Val Gln Phe Ala Glu Tyr Ile Gln Lys Asn Val
    50                  55                  60

Gln Leu Tyr Lys Met Arg Asn Gly Tyr Glu Leu Ser Pro Thr Ala Ala
65                  70                  75                  80

Ala Asn Phe Thr Arg Arg Asn Leu Ala Asp Cys Leu Arg Ser Arg Thr
                85                  90                  95

Pro Tyr His Val Asn Leu Leu Leu Ala Gly Tyr Asp Glu His Glu Gly
            100                 105                 110

Pro Ala Leu Tyr Tyr Met Asp Tyr Leu Ala Ala Leu Ala Lys Ala Pro
        115                 120                 125

Phe Ala Ala His Gly Tyr Gly Ala Phe Leu Thr Leu Ser Ile Leu Asp
    130                 135                 140

Arg Tyr Tyr Thr Pro Thr Ile Ser Arg Glu Arg Ala Val Glu Leu Leu
145                 150                 155                 160

Arg Lys Cys Leu Glu Glu Leu Gln Lys Arg Phe Ile Leu Asn Leu Pro
                165                 170                 175

Thr Phe Ser Val Arg Ile Ile Asp Lys Asn Gly Ile His Asp Leu Asp
            180                 185                 190

Asn Ile Ser Phe Pro Lys Gln Gly Ser
        195                 200
```

<210> SEQ ID NO 15
<211> LENGTH: 175
<212> TYPE: PRT
<213> ORGANISM: Homo sapien

<400> SEQUENCE: 15

```
Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125
```

Phe Leu Glu Thr His Phe Leu Asp Glu Val Lys Leu Ile Lys Lys
130                 135                 140

Met Gly Asp His Leu Thr Asn Leu His Arg Leu Gly Pro Glu Ala
145                 150                 155                 160

Gly Leu Gly Glu Tyr Leu Phe Glu Arg Leu Thr Leu Lys His Asp
                165                 170                 175

<210> SEQ ID NO 16
<211> LENGTH: 95
<212> TYPE: PRT
<213> ORGANISM: Homo sapien

<400> SEQUENCE: 16

Met Ala Lys Pro Ala Gln Gly Ala Lys Tyr Arg Gly Ser Ile His Asp
1               5                   10                  15

Phe Pro Gly Phe Asp Pro Asn Gln Asp Ala Glu Ala Leu Tyr Thr Ala
                20                  25                  30

Met Lys Gly Phe Gly Ser Asp Lys Glu Ala Ile Leu Asp Ile Ile Thr
            35                  40                  45

Ser Arg Ser Asn Arg Gln Arg Gln Glu Val Cys Gln Ser Tyr Lys Ser
50                  55                  60

Leu Tyr Gly Lys Asp Leu Ile Ala Asp Leu Lys Tyr Glu Leu Thr Gly
65                  70                  75                  80

Lys Phe Glu Arg Leu Ile Val Gly Gly Leu Ser Asp Val Gly Thr
                85                  90                  95

<210> SEQ ID NO 17
<211> LENGTH: 125
<212> TYPE: PRT
<213> ORGANISM: Homo sapien

<400> SEQUENCE: 17

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
                20                  25                  30

Ser Ile Val Gly Arg Pro Arg His Gln Gly Val Met Val Gly Met Gly
            35                  40                  45

Gln Lys Asp Ser Tyr Val Gly Asp Glu Ala Gln Ser Lys Arg Gly Ile
50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Asp Ser Leu Leu
            115                 120                 125

<210> SEQ ID NO 18
<211> LENGTH: 584
<212> TYPE: PRT
<213> ORGANISM: Homo sapien

<400> SEQUENCE: 18

Met Ser Val Arg Tyr Ser Ser Ser Lys His Tyr Ser Ser Ser Arg Ser
1               5                   10                  15

Gly Gly Gly Gly Gly Gly Gly Cys Gly Gly Gly Gly Gly Val Ser

```
                  20                  25                  30
Ser Leu Arg Ile Ser Ser Ser Lys Gly Ser Leu Gly Gly Gly Phe Ser
            35                  40                  45
Ser Gly Gly Phe Ser Gly Gly Ser Phe Ser Arg Gly Ser Ser Gly Gly
        50                  55                  60
Gly Cys Phe Gly Gly Ser Ser Gly Gly Tyr Gly Leu Gly Gly Phe
65                  70                  75                  80
Gly Gly Gly Ser Phe Arg Gly Ser Tyr Gly Ser Ser Phe Gly Gly
                85                  90                  95
Ser Tyr Gly Gly Ile Phe Gly Gly Ser Phe Gly Gly Ser Phe
            100                 105                 110
Gly Gly Gly Ser Phe Gly Gly Gly Phe Gly Gly Gly Phe Gly
        115                 120                 125
Gly Gly Phe Gly Gly Gly Phe Gly Gly Asp Gly Leu Leu Ser Gly
        130                 135                 140
Asn Glu Lys Val Thr Met Gln Asn Leu Asn Asp Arg Leu Ala Ser Tyr
145                 150                 155                 160
Leu Asp Lys Val Arg Ala Leu Glu Glu Ser Asn Tyr Glu Leu Glu Gly
                165                 170                 175
Lys Ile Lys Glu Trp Tyr Glu Lys His Gly Asn Ser His Gln Gly Glu
            180                 185                 190
Pro Arg Asp Tyr Ser Lys Tyr Tyr Lys Thr Ile Asp Asp Leu Lys Asn
            195                 200                 205
Gln Ile Leu Asn Leu Thr Thr Asp Asn Ala Asn Ile Leu Leu Gln Ile
        210                 215                 220
Asp Asn Ala Arg Leu Ala Ala Asp Asp Phe Arg Leu Lys Tyr Glu Asn
225                 230                 235                 240
Glu Val Ala Leu Arg Gln Ser Val Glu Ala Asp Ile Asn Gly Leu Arg
                245                 250                 255
Arg Val Leu Asp Glu Leu Thr Leu Thr Lys Ala Asp Leu Glu Met Gln
            260                 265                 270
Ile Glu Ser Leu Thr Glu Glu Leu Ala Tyr Leu Lys Lys Asn His Glu
        275                 280                 285
Glu Glu Met Lys Asp Leu Arg Asn Val Ser Thr Gly Asp Val Asn Val
        290                 295                 300
Glu Met Asn Ala Ala Pro Gly Val Asp Leu Thr Gln Leu Leu Asn Asn
305                 310                 315                 320
Met Arg Ser Gln Tyr Glu Gln Leu Ala Glu Gln Asn Arg Lys Asp Ala
                325                 330                 335
Glu Ala Trp Phe Asn Glu Lys Ser Lys Glu Leu Thr Thr Glu Ile Asp
            340                 345                 350
Asn Asn Ile Glu Gln Ile Ser Ser Tyr Lys Ser Glu Ile Thr Glu Leu
            355                 360                 365
Arg Arg Asn Val Gln Ala Leu Glu Ile Glu Leu Gln Ser Gln Leu Ala
        370                 375                 380
Leu Lys Gln Ser Leu Glu Ala Ser Leu Ala Glu Thr Glu Gly Arg Tyr
385                 390                 395                 400
Cys Val Gln Leu Ser Gln Ile Gln Ala Gln Ile Ser Ala Leu Glu Glu
                405                 410                 415
Gln Leu Gln Gln Ile Arg Ala Glu Thr Glu Cys Gln Asn Thr Glu Tyr
            420                 425                 430
Gln Gln Leu Leu Asp Ile Lys Ile Arg Leu Glu Asn Glu Ile Gln Thr
        435                 440                 445
```

```
Tyr Arg Ser Leu Leu Glu Gly Glu Gly Ser Gly Gly Gly Arg
    450                 455                 460

Gly Gly Gly Ser Phe Gly Gly Tyr Gly Gly Ser Ser Gly Gly
465                 470                 475                 480

Gly Ser Ser Gly Gly Gly His Gly Gly His Gly Gly Ser Ser Gly
                485                 490                 495

Gly Gly Tyr Gly Gly Gly Ser Ser Gly Gly Ser Ser Gly Gly Gly
            500                 505                 510

Tyr Gly Gly Gly Ser Ser Gly His Gly Gly Ser Ser Gly
        515                 520                 525

Gly Tyr Gly Gly Gly Ser Ser Gly Gly Gly Gly Tyr Gly Gly
    530                 535                 540

Gly Ser Ser Gly Gly Gly Ser Ser Gly Gly Gly Tyr Gly Gly
545                 550                 555                 560

Ser Ser Ser Gly Gly His Lys Ser Ser Ser Ser Gly Ser Val Gly Glu
                565                 570                 575

Ser Ser Ser Lys Gly Pro Arg Tyr
            580
```

<210> SEQ ID NO 19
<211> LENGTH: 156
<212> TYPE: PRT
<213> ORGANISM: Homo sapien

<400> SEQUENCE: 19

```
Met Ser Lys Ser Glu Ser Pro Lys Glu Pro Glu Gln Leu Arg Lys Leu
1               5                   10                  15

Phe Ile Gly Gly Leu Ser Phe Glu Thr Thr Asp Glu Ser Leu Arg Ser
                20                  25                  30

His Phe Glu Gln Trp Gly Thr Leu Thr Asp Cys Val Val Met Arg Asp
            35                  40                  45

Pro Asn Thr Lys Arg Ser Arg Gly Phe Gly Phe Val Thr Tyr Ala Thr
        50                  55                  60

Val Glu Glu Val Asp Ala Ala Met Asn Ala Arg Pro His Lys Val Asp
65              70                  75                  80

Gly Arg Val Val Glu Pro Lys Arg Ala Val Ser Arg Glu Asp Ser Gln
                85                  90                  95

Arg Pro Gly Ala His Leu Thr Val Lys Lys Ile Phe Val Gly Gly Phe
            100                 105                 110

Gly Gly Ser Arg Gly Gly Gly Gly Tyr Gly Gly Ser Gly Asp Gly Tyr
        115                 120                 125

Asn Gly Phe Gly Asn Asp Gly Ser Asn Phe Gly Gly Gly Ser Tyr
    130                 135                 140

Asn Asp Phe Gly Asn Tyr Asn Asn Gln Ser Ser Asn
145                 150                 155
```

<210> SEQ ID NO 20
<211> LENGTH: 93
<212> TYPE: PRT
<213> ORGANISM: Homo sapien

<400> SEQUENCE: 20

```
Met Ser Gly Leu Arg Val Tyr Ser Thr Ser Val Thr Gly Ser Arg Glu
1               5                   10                  15

Ile Lys Ser Gln Gln Ser Glu Val Thr Arg Ile Leu Asp Gly Lys Arg
                20                  25                  30
```

```
Ile Gln Tyr Gln Leu Val Asp Ile Ser Gln Asp Asn Ala Leu Arg Asp
            35                  40                  45

Glu Met Arg Ala Leu Ala Gly Asn Pro Lys Ala Thr Pro Pro Gln Ile
 50                  55                  60

Val Asn Gly Asp Gln Tyr Cys Gly Asp Tyr Glu Leu Phe Val Glu Ala
 65                  70                  75                  80

Val Glu Gln Asn Thr Leu Gln Glu Phe Leu Lys Leu Ala
                 85                  90

<210> SEQ ID NO 21
<211> LENGTH: 184
<212> TYPE: PRT
<213> ORGANISM: Homo sapien

<400> SEQUENCE: 21

Met Arg Glu Tyr Lys Leu Val Val Leu Gly Ser Gly Gly Val Gly Lys
 1               5                  10                  15

Ser Ala Leu Thr Val Gln Phe Val Gln Gly Ile Phe Val Glu Lys Tyr
            20                  25                  30

Asp Pro Thr Ile Glu Asp Ser Tyr Arg Lys Gln Val Glu Val Asp Ala
            35                  40                  45

Gln Gln Cys Met Leu Glu Ile Leu Asp Thr Ala Gly Thr Glu Gln Phe
 50                  55                  60

Thr Ala Met Arg Asp Leu Tyr Met Lys Asn Gly Gln Gly Phe Ala Leu
 65                  70                  75                  80

Val Tyr Ser Ile Thr Ala Gln Ser Thr Phe Asn Asp Leu Gln Asp Leu
            85                  90                  95

Arg Glu Gln Ile Leu Arg Val Lys Asp Thr Asp Asp Val Pro Met Ile
            100                 105                 110

Leu Val Gly Asn Lys Cys Asp Leu Glu Asp Glu Arg Val Val Gly Lys
            115                 120                 125

Glu Gln Gly Gln Asn Leu Ala Arg Gln Trp Asn Asn Cys Ala Phe Leu
            130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Pro Gly Lys Ala Arg
                165                 170                 175

Lys Lys Ser Ser Cys Gln Leu Leu
            180

<210> SEQ ID NO 22
<211> LENGTH: 375
<212> TYPE: PRT
<213> ORGANISM: Homo sapien

<400> SEQUENCE: 22

Met Asp Asp Asp Ile Ala Ala Leu Val Val Asp Asn Gly Ser Gly Met
 1               5                  10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
            35                  40                  45

Gln Lys Asp Ser Tyr Val Gly Asp Glu Ala Gln Ser Lys Arg Gly Ile
 50                  55                  60

Leu Thr Leu Lys Tyr Pro Ile Glu His Gly Ile Val Thr Asn Trp Asp
 65                  70                  75                  80
```

-continued

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375

<210> SEQ ID NO 23
<211> LENGTH: 1075
<212> TYPE: PRT
<213> ORGANISM: Homo sapien

<400> SEQUENCE: 23

Met Val Val Glu Val Asp Ser Met Pro Ala Ala Ser Ser Val Lys Lys
1               5                   10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
        35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val

-continued

```
                65                  70                  75                  80
Gly Ala Ser Gly Asp His Asp Ser Ala Met Lys Thr Leu Arg Asn
                        85                  90                  95
Lys Met Gly Lys Trp Cys Cys His Cys Phe Pro Cys Cys Arg Gly Ser
                100                 105                 110
Ser Lys Ser Lys Val Gly Ala Trp Gly Asp Tyr Asp Ser Ala Phe
            115                 120                 125
Met Glu Pro Arg Tyr His Val Arg Gly Glu Asp Leu Asp Lys Leu His
    130                 135                 140
Arg Ala Ala Trp Trp Gly Lys Val Pro Arg Lys Asp Leu Ile Val Met
145                 150                 155                 160
Leu Arg Asp Thr Asp Val Asn Lys Gln Asp Lys Gln Lys Arg Thr Ala
                165                 170                 175
Leu His Leu Ala Ser Ala Asn Gly Asn Ser Glu Val Val Lys Leu Leu
            180                 185                 190
Leu Asp Arg Arg Cys Gln Leu Asn Val Leu Asp Asn Lys Lys Arg Thr
        195                 200                 205
Ala Leu Ile Lys Ala Val Gln Cys Gln Glu Asp Glu Cys Ala Leu Met
    210                 215                 220
Leu Leu Glu His Gly Thr Asp Pro Asn Ile Pro Asp Glu Tyr Gly Asn
225                 230                 235                 240
Thr Thr Leu His Tyr Ala Ile Tyr Asn Glu Asp Lys Leu Met Ala Lys
                245                 250                 255
Ala Leu Leu Leu Tyr Gly Ala Asp Ile Glu Ser Lys Asn Lys His Gly
            260                 265                 270
Leu Thr Pro Leu Leu Leu Gly Val His Glu Gln Lys Gln Gln Val Val
        275                 280                 285
Lys Phe Leu Ile Lys Lys Lys Ala Asn Leu Asn Ala Leu Asp Arg Tyr
    290                 295                 300
Gly Arg Thr Ala Leu Ile Leu Ala Val Cys Cys Gly Ser Ala Ser Ile
305                 310                 315                 320
Val Ser Leu Leu Leu Glu Gln Asn Ile Asp Val Ser Ser Gln Asp Leu
                325                 330                 335
Ser Gly Gln Thr Ala Arg Glu Tyr Ala Val Ser Ser His His His Val
            340                 345                 350
Ile Cys Gln Leu Leu Ser Asp Tyr Lys Glu Lys Gln Met Leu Lys Ile
        355                 360                 365
Ser Ser Glu Asn Ser Asn Pro Glu Gln Asp Leu Lys Leu Thr Ser Glu
    370                 375                 380
Glu Glu Ser Gln Arg Phe Lys Gly Ser Glu Asn Ser Gln Pro Glu Lys
385                 390                 395                 400
Met Ser Gln Glu Pro Glu Ile Asn Lys Asp Gly Asp Arg Glu Val Glu
                405                 410                 415
Glu Glu Met Lys Lys His Glu Ser Asn Asn Val Gly Leu Leu Glu Asn
            420                 425                 430
Leu Thr Asn Gly Val Thr Ala Gly Asn Gly Asp Asn Gly Leu Ile Pro
        435                 440                 445
Gln Arg Lys Ser Arg Thr Pro Glu Asn Gln Gln Phe Pro Asp Asn Glu
    450                 455                 460
Ser Glu Glu Tyr His Arg Ile Cys Glu Leu Leu Ser Asp Tyr Lys Glu
465                 470                 475                 480
Lys Gln Met Pro Lys Tyr Ser Ser Glu Asn Ser Asn Pro Glu Gln Asp
                485                 490                 495
```

```
Leu Lys Leu Thr Ser Glu Glu Ser Gln Arg Leu Lys Gly Ser Glu
            500                 505                 510

Asn Gly Gln Pro Glu Lys Arg Ser Gln Glu Pro Glu Ile Asn Lys Asp
        515                 520                 525

Gly Asp Arg Glu Leu Glu Asn Phe Met Ala Ile Glu Glu Met Lys Lys
    530                 535                 540

His Arg Ser Thr His Val Gly Phe Pro Glu Asn Leu Thr Asn Gly Ala
545                 550                 555                 560

Thr Ala Gly Asn Gly Asp Asp Gly Leu Ile Pro Pro Arg Lys Ser Arg
                565                 570                 575

Thr Pro Glu Ser Gln Gln Phe Pro Asp Thr Glu Asn Glu Glu Tyr His
            580                 585                 590

Ser Asp Glu Gln Asn Asp Thr Gln Lys Gln Phe Cys Glu Glu Gln Asn
        595                 600                 605

Thr Gly Ile Leu His Asp Glu Ile Leu Ile His Glu Glu Lys Gln Ile
    610                 615                 620

Glu Val Val Glu Lys Met Asn Ser Glu Leu Ser Leu Ser Cys Lys Lys
625                 630                 635                 640

Glu Lys Asp Ile Leu His Glu Asn Ser Thr Leu Arg Glu Glu Ile Ala
                645                 650                 655

Met Leu Arg Leu Glu Leu Asp Thr Met Lys His Gln Ser Gln Leu Arg
            660                 665                 670

Glu Lys Lys Tyr Leu Glu Asp Ile Glu Ser Val Lys Lys Arg Asn Asp
        675                 680                 685

Asn Leu Leu Lys Ala Leu Gln Leu Asn Glu Leu Thr Met Asp Asp Asp
    690                 695                 700

Thr Ala Val Leu Val Ile Asp Asn Gly Ser Gly Met Cys Lys Ala Gly
705                 710                 715                 720

Phe Ala Gly Asp Asp Ala Pro Arg Ala Val Phe Pro Ser Ile Val Gly
                725                 730                 735

Arg Pro Arg Gln Gln Gly Met Met Gly Met His Gln Lys Glu Ser
            740                 745                 750

Tyr Val Gly Lys Glu Ala Gln Ser Lys Arg Gly Ile Leu Thr Leu Lys
            755                 760                 765

Tyr Pro Met Glu His Gly Ile Ile Thr Asn Trp Asp Asp Met Glu Lys
        770                 775                 780

Ile Trp His His Thr Phe Tyr Asn Glu Leu Arg Val Ala Pro Glu Glu
785                 790                 795                 800

His Pro Val Leu Leu Thr Glu Ala Thr Leu Asn Pro Lys Ala Asn Arg
                805                 810                 815

Glu Lys Met Thr Gln Ile Met Phe Glu Thr Phe Asn Thr Pro Ala Met
            820                 825                 830

Tyr Val Ala Ile Gln Ala Val Leu Ser Leu Tyr Thr Ser Gly Arg Thr
        835                 840                 845

Thr Gly Ile Val Met Asp Ser Gly Asp Gly Val Thr His Thr Val Pro
    850                 855                 860

Ile Tyr Glu Gly Asn Ala Leu Pro His Ala Thr Leu Arg Leu Asp Leu
865                 870                 875                 880

Ala Gly Arg Glu Leu Pro Asp Tyr Leu Met Lys Ile Leu Thr Glu His
                885                 890                 895

Gly Tyr Arg Phe Thr Thr Met Ala Glu Arg Glu Ile Val Arg Asp Ile
            900                 905                 910
```

```
Lys Glu Lys Leu Cys Tyr Val Ala Leu Asp Phe Glu Gln Met Ala
        915                 920                 925

Thr Val Ala Ser Ser Ser Leu Glu Lys Ser Tyr Glu Leu Pro Asp
    930                 935                 940

Gly Gln Val Ile Thr Ile Gly Asn Glu Arg Phe Arg Cys Pro Glu Ala
945                 950                 955                 960

Leu Phe Gln Pro Cys Phe Leu Gly Met Glu Ser Cys Gly Ile His Glu
                965                 970                 975

Thr Thr Phe Asn Ser Ile Met Lys Ser Asp Val Asp Ile Arg Lys Asp
                980                 985                 990

Leu Tyr Thr Asn Thr Val Leu Ser Gly Gly Thr Thr Met Tyr Pro Gly
        995                 1000                1005

Met Ala His Arg Met Gln Lys Glu Ile Ala Ala Leu Ala Pro Ser
    1010                1015                1020

Met Met Lys Ile Arg Ile Ile Ala Pro Pro Lys Arg Lys Tyr Ser
    1025                1030                1035

Val Trp Val Gly Gly Ser Ile Leu Ala Ser Leu Ser Thr Phe Gln
    1040                1045                1050

Gln Met Trp Ile Ser Lys Gln Glu Tyr Asp Glu Ser Gly Pro Ser
    1055                1060                1065

Ile Val His Arg Lys Cys Leu
    1070                1075

<210> SEQ ID NO 24
<211> LENGTH: 111
<212> TYPE: PRT
<213> ORGANISM: Homo sapien

<400> SEQUENCE: 24

Met Phe Gly Gly Pro Gly Thr Gly Ser Arg Pro Ser Thr Arg Ser
1               5                   10                  15

Tyr Val Thr Thr Ser Thr Arg Thr Tyr Ser Leu Gly Ser Ala Leu Arg
                20                  25                  30

Pro Ser Thr Ser Arg Ser Leu Tyr Thr Ser Pro Gly Gly Ala Tyr
            35                  40                  45

Val Thr Arg Ser Ser Ala Val Arg Leu Arg Ser Ser Val Pro Gly Val
50                  55                  60

Arg Leu Leu Gln Asp Ser Val Asp Phe Ser Leu Ala Asp Ala Ile Asn
65                  70                  75                  80

Thr Glu Phe Lys Asn Thr Arg Thr Asn Glu Lys Val Glu Leu Gln Glu
                85                  90                  95

Leu Asn Asp Arg Phe Ala Asn Tyr Ile Asp Lys Val Arg Phe Leu
                100                 105                 110

<210> SEQ ID NO 25
<211> LENGTH: 105
<212> TYPE: PRT
<213> ORGANISM: Homo sapien

<400> SEQUENCE: 25

Met Ala Lys Ile Ser Ser Pro Thr Glu Thr Glu Arg Cys Ile Glu Ser
1               5                   10                  15

Leu Ile Ala Val Phe Gln Lys Tyr Ala Gly Lys Asp Gly Tyr Asn Tyr
                20                  25                  30

Thr Leu Ser Lys Thr Glu Phe Leu Ser Phe Met Asn Thr Glu Leu Ala
                35                  40                  45
```

Ala Phe Thr Lys Asn Gln Lys Asp Pro Gly Val Leu Asp Arg Met Met
 50                  55                  60

Lys Lys Leu Asp Thr Asn Ser Asp Gly Gln Leu Asp Phe Ser Glu Phe
 65                  70                  75                  80

Leu Asn Leu Ile Gly Gly Leu Ala Met Ala Cys His Asp Ser Phe Leu
                 85                  90                  95

Lys Ala Val Pro Ser Gln Lys Arg Thr
            100                 105

<210> SEQ ID NO 26
<211> LENGTH: 866
<212> TYPE: PRT
<213> ORGANISM: Homo sapien

<400> SEQUENCE: 26

Met Phe Ser Met Arg Ile Val Cys Leu Val Leu Ser Val Val Gly Thr
 1               5                  10                  15

Ala Trp Thr Ala Asp Ser Gly Glu Gly Asp Phe Leu Ala Glu Gly Gly
                 20                  25                  30

Gly Val Arg Gly Pro Arg Val Val Glu Arg His Gln Ser Ala Cys Lys
             35                  40                  45

Asp Ser Asp Trp Pro Phe Cys Ser Asp Glu Asp Trp Asn Tyr Lys Cys
 50                  55                  60

Pro Ser Gly Cys Arg Met Lys Gly Leu Ile Asp Glu Val Asn Gln Asp
 65                  70                  75                  80

Phe Thr Asn Arg Ile Asn Lys Leu Lys Asn Ser Leu Phe Glu Tyr Gln
                 85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
290                 295                 300

Thr Gly Asn Arg Asn Pro Gly Ser Ser Gly Thr Gly Gly Thr Ala Thr
305                 310                 315                 320

-continued

Trp Lys Pro Gly Ser Ser Gly Pro Gly Ser Thr Gly Ser Trp Asn Ser
            325                 330                 335
Gly Ser Ser Gly Thr Gly Ser Thr Gly Asn Gln Asn Pro Gly Ser Pro
            340                 345                 350
Arg Pro Gly Ser Thr Gly Thr Trp Asn Pro Gly Ser Ser Glu Arg Gly
            355                 360                 365
Ser Ala Gly His Trp Thr Ser Glu Ser Ser Val Ser Gly Ser Thr Gly
            370                 375                 380
Gln Trp His Ser Glu Ser Gly Ser Phe Arg Pro Asp Ser Pro Gly Ser
385                 390                 395                 400
Gly Asn Ala Arg Pro Asn Asn Pro Asp Trp Thr Phe Glu Glu Val
            405                 410                 415
Ser Gly Asn Val Ser Pro Gly Thr Arg Arg Glu Tyr His Thr Glu Lys
            420                 425                 430
Leu Val Thr Ser Lys Gly Asp Lys Glu Leu Arg Thr Gly Lys Glu Lys
            435                 440                 445
Val Thr Ser Gly Ser Thr Thr Thr Arg Arg Ser Cys Ser Lys Thr
            450                 455                 460
Val Thr Lys Thr Val Ile Gly Pro Asp Gly His Lys Glu Val Thr Lys
465                 470                 475                 480
Glu Val Val Thr Ser Glu Asp Gly Ser Asp Cys Pro Glu Ala Met Asp
            485                 490                 495
Leu Gly Thr Leu Ser Gly Ile Gly Thr Leu Asp Gly Phe Arg His Arg
            500                 505                 510
His Pro Asp Glu Ala Ala Phe Phe Asp Thr Ala Ser Thr Gly Lys Thr
            515                 520                 525
Phe Pro Gly Phe Phe Ser Pro Met Leu Gly Glu Phe Val Ser Glu Thr
            530                 535                 540
Glu Ser Arg Gly Ser Glu Ser Gly Ile Phe Thr Asn Thr Lys Glu Ser
545                 550                 555                 560
Ser Ser His His Pro Gly Ile Ala Glu Phe Pro Ser Arg Gly Lys Ser
            565                 570                 575
Ser Ser Tyr Ser Lys Gln Phe Thr Ser Ser Thr Ser Tyr Asn Arg Gly
            580                 585                 590
Asp Ser Thr Phe Glu Ser Lys Ser Tyr Lys Met Ala Asp Glu Ala Gly
            595                 600                 605
Ser Glu Ala Asp His Glu Gly Thr His Ser Thr Lys Arg Gly His Ala
610                 615                 620
Lys Ser Arg Pro Val Arg Asp Cys Asp Asp Val Leu Gln Thr His Pro
625                 630                 635                 640
Ser Gly Thr Gln Ser Gly Ile Phe Asn Ile Lys Leu Pro Gly Ser Ser
            645                 650                 655
Lys Ile Phe Ser Val Tyr Cys Asp Gln Glu Thr Ser Leu Gly Gly Trp
            660                 665                 670
Leu Leu Ile Gln Gln Arg Met Asp Gly Ser Leu Asn Phe Asn Arg Thr
            675                 680                 685
Trp Gln Asp Tyr Lys Arg Gly Phe Gly Ser Leu Asn Asp Glu Gly Glu
            690                 695                 700
Gly Glu Phe Trp Leu Gly Asn Asp Tyr Leu His Leu Leu Thr Gln Arg
705                 710                 715                 720
Gly Ser Val Leu Arg Val Glu Leu Glu Asp Trp Ala Gly Asn Glu Ala
            725                 730                 735

```
Tyr Ala Glu Tyr His Phe Arg Val Gly Ser Ala Glu Gly Tyr Ala
                740                 745                 750

Leu Gln Val Ser Ser Tyr Glu Gly Thr Ala Gly Asp Ala Leu Ile Glu
        755                 760                 765

Gly Ser Val Glu Glu Gly Ala Glu Tyr Thr Ser His Asn Asn Met Gln
    770                 775                 780

Phe Ser Thr Phe Asp Arg Asp Ala Asp Gln Trp Glu Glu Asn Cys Ala
785                 790                 795                 800

Glu Val Tyr Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
                820                 825                 830

Ser Pro Tyr Glu Ile Glu Asn Gly Val Val Trp Val Ser Phe Arg Gly
                835                 840                 845

Ala Asp Tyr Ser Leu Arg Ala Val Arg Met Lys Ile Arg Pro Leu Val
        850                 855                 860

Thr Gln
865

<210> SEQ ID NO 27
<211> LENGTH: 426
<212> TYPE: PRT
<213> ORGANISM: Homo sapien

<400> SEQUENCE: 27

Met Phe Trp Glu Val Ile Ser Asp Glu His Gly Ile Asp Pro Thr Gly
1               5                   10                  15

Thr Tyr His Gly Asp Ser Asp Leu Gln Leu Asp Arg Ile Ser Val Tyr
                20                  25                  30

Tyr Asn Glu Ala Thr Gly Gly Lys Tyr Val Pro Arg Ala Ile Leu Val
            35                  40                  45

Asp Leu Glu Pro Gly Thr Met Asp Ser Val Arg Ser Gly Pro Phe Gly
        50                  55                  60

Gln Ile Phe Arg Pro Asp Asn Phe Val Phe Gly Gln Ser Gly Ala Gly
65              70                  75                  80

Asn Asn Trp Ala Lys Gly His Tyr Thr Glu Gly Ala Glu Leu Val Asp
                85                  90                  95

Ser Val Leu Asp Val Val Arg Lys Glu Ala Glu Ser Cys Asp Cys Leu
            100                 105                 110

Gln Gly Phe Gln Leu Thr His Ser Leu Gly Gly Gly Thr Gly Ser Gly
        115                 120                 125

Met Gly Thr Leu Leu Ile Ser Lys Ile Arg Glu Glu Tyr Pro Asp Arg
130             135                 140

Ile Met Asn Thr Phe Ser Val Val Pro Ser Pro Lys Val Ser Asp Thr
145             150                 155                 160

Val Val Glu Pro Tyr Asn Ala Thr Leu Ser Val His Gln Leu Val Glu
                165                 170                 175

Asn Thr Asp Glu Thr Tyr Cys Ile Asp Asn Glu Ala Leu Tyr Asp Ile
            180                 185                 190

Cys Phe Arg Thr Leu Lys Leu Thr Thr Pro Thr Tyr Gly Asp Leu Asn
        195                 200                 205

His Leu Val Ser Ala Thr Met Ser Gly Val Thr Thr Cys Leu Arg Phe
    210                 215                 220

Pro Gly Gln Leu Asn Ala Asp Leu Arg Lys Leu Ala Val Asn Met Val
225             230                 235                 240
```

-continued

```
Pro Phe Pro Arg Leu His Phe Met Pro Gly Phe Ala Pro Leu Thr
                245                 250                 255

Ser Arg Gly Ser Gln Gln Tyr Arg Ala Leu Thr Val Pro Glu Leu Thr
            260                 265                 270

Gln Gln Val Phe Asp Ala Lys Asn Met Met Ala Ala Cys Asp Pro Arg
            275                 280                 285

His Gly Arg Tyr Leu Thr Val Ala Ala Val Phe Arg Gly Arg Met Ser
        290                 295                 300

Met Lys Glu Val Asp Glu Gln Met Leu Asn Val Gln Asn Lys Asn Ser
305                 310                 315                 320

Ser Tyr Phe Val Glu Trp Ile Pro Asn Asn Val Lys Thr Ala Val Cys
                325                 330                 335

Asp Ile Pro Pro Arg Gly Leu Lys Met Ala Val Thr Phe Ile Gly Asn
            340                 345                 350

Ser Thr Ala Ile Gln Glu Leu Phe Lys Arg Ile Ser Glu Gln Phe Thr
        355                 360                 365

Ala Met Phe Arg Arg Lys Ala Phe Leu His Trp Tyr Thr Gly Glu Gly
    370                 375                 380

Met Asp Glu Met Glu Phe Thr Glu Ala Glu Ser Asn Met Asn Asp Leu
385                 390                 395                 400

Val Ser Glu Tyr Gln Gln Tyr Gln Asp Ala Thr Ala Glu Glu Glu Glu
                405                 410                 415

Asp Phe Gly Glu Glu Ala Glu Glu Ala
            420                 425

<210> SEQ ID NO 28
<211> LENGTH: 172
<212> TYPE: PRT
<213> ORGANISM: Homo sapien

<400> SEQUENCE: 28

Met Ser Ser Lys Lys Ala Lys Thr Lys Thr Thr Lys Lys Arg Pro Gln
1               5                   10                  15

Arg Ala Thr Ser Asn Val Phe Ala Met Phe Asp Gln Ser Gln Ile Gln
            20                  25                  30

Glu Phe Lys Glu Ala Phe Asn Met Ile Asp Gln Asn Arg Asp Gly Phe
        35                  40                  45

Ile Asp Lys Glu Asp Leu His Asp Met Leu Ala Ser Leu Gly Lys Asn
    50                  55                  60

Pro Thr Asp Ala Tyr Leu Asp Ala Met Met Asn Glu Ala Pro Gly Pro
65                  70                  75                  80

Ile Asn Phe Thr Met Phe Leu Thr Met Phe Gly Glu Lys Leu Asn Gly
                85                  90                  95

Thr Asp Pro Glu Asp Val Ile Arg Asn Ala Phe Ala Cys Phe Asp Glu
            100                 105                 110

Glu Ala Thr Gly Thr Ile Gln Glu Asp Tyr Leu Arg Glu Leu Leu Thr
        115                 120                 125

Thr Met Gly Asp Arg Phe Thr Asp Glu Glu Val Asp Glu Leu Tyr Arg
    130                 135                 140

Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp Asp
                165                 170
```

```
<210> SEQ ID NO 29
<211> LENGTH: 323
<212> TYPE: PRT
<213> ORGANISM: Homo sapien

<400> SEQUENCE: 29

Met Ala Ser Ile Trp Val Gly His Arg Gly Thr Val Arg Asp Tyr Pro
1               5                   10                  15

Asp Phe Ser Pro Ser Val Asp Ala Glu Ala Ile Gln Lys Ala Ile Arg
                20                  25                  30

Gly Ile Gly Thr Asp Glu Lys Met Leu Ile Ser Ile Leu Thr Glu Arg
            35                  40                  45

Ser Asn Ala Gln Arg Gln Leu Ile Val Lys Glu Tyr Gln Ala Ala Tyr
    50                  55                  60

Gly Lys Glu Leu Lys Asp Asp Leu Lys Gly Asp Leu Ser Gly His Phe
65                  70                  75                  80

Glu His Leu Met Val Ala Leu Val Thr Pro Pro Ala Val Phe Asp Ala
                85                  90                  95

Lys Gln Leu Lys Lys Ser Met Lys Gly Ala Gly Thr Asn Glu Asp Ala
                100                 105                 110

Leu Ile Glu Ile Leu Thr Thr Arg Thr Ser Arg Gln Met Lys Asp Ile
            115                 120                 125

Ser Gln Ala Tyr Tyr Thr Val Tyr Lys Lys Ser Leu Gly Asp Asp Ile
    130                 135                 140

Ser Ser Glu Thr Ser Gly Asp Phe Arg Lys Ala Leu Leu Thr Leu Ala
145                 150                 155                 160

Asp Gly Arg Arg Asp Glu Ser Leu Lys Val Asp Glu His Leu Ala Lys
                165                 170                 175

Gln Asp Ala Gln Ile Leu Tyr Lys Ala Gly Glu Asn Arg Trp Gly Thr
            180                 185                 190

Asp Glu Asp Lys Phe Thr Glu Ile Leu Cys Leu Arg Ser Phe Pro Gln
    195                 200                 205

Leu Lys Leu Thr Phe Asp Glu Tyr Arg Asn Ile Ser Gln Lys Asp Ile
210                 215                 220

Val Asp Ser Ile Lys Gly Glu Leu Ser Gly His Phe Glu Asp Leu Leu
225                 230                 235                 240

Leu Ala Ile Val Asn Cys Val Arg Asn Thr Pro Ala Phe Leu Ala Glu
                245                 250                 255

Arg Leu His Arg Ala Leu Lys Gly Ile Gly Thr Asp Glu Phe Thr Leu
            260                 265                 270

Asn Arg Ile Met Val Ser Arg Ser Glu Ile Asp Leu Leu Asp Ile Arg
    275                 280                 285

Thr Glu Phe Lys Lys His Tyr Gly Tyr Ser Leu Tyr Ser Ala Ile Lys
            290                 295                 300

Ser Asp Thr Ser Gly Asp Tyr Glu Ile Thr Leu Leu Lys Ile Cys Gly
305                 310                 315                 320

Gly Asp Asp

<210> SEQ ID NO 30
<211> LENGTH: 584
<212> TYPE: PRT
<213> ORGANISM: Homo sapien

<400> SEQUENCE: 30

Met Ser Val Arg Tyr Ser Ser Lys His Tyr Ser Ser Arg Ser
1               5                   10                  15
```

-continued

```
Gly Gly Gly Gly Gly Gly Gly Cys Gly Gly Gly Gly Val Ser
            20                  25              30

Ser Leu Arg Ile Ser Ser Lys Gly Ser Leu Gly Gly Phe Ser
        35              40              45

Ser Gly Gly Phe Ser Gly Ser Phe Arg Gly Ser Ser Gly Gly
50              55                  60

Gly Cys Phe Gly Gly Ser Ser Gly Gly Tyr Gly Gly Leu Gly Gly Phe
65              70                  75              80

Gly Gly Gly Ser Phe Arg Gly Ser Tyr Gly Ser Ser Phe Gly Gly
                85              90              95

Ser Tyr Gly Gly Ile Phe Gly Gly Ser Phe Gly Gly Ser Phe
            100             105             110

Gly Gly Gly Ser Phe Gly Gly Gly Phe Gly Gly Gly Phe Gly
            115             120             125

Gly Gly Phe Gly Gly Gly Phe Gly Gly Asp Gly Gly Leu Leu Ser Gly
        130             135             140

Asn Glu Lys Val Thr Met Gln Asn Leu Asn Asp Arg Leu Ala Ser Tyr
145             150             155             160

Leu Asp Lys Val Arg Ala Leu Glu Glu Ser Asn Tyr Glu Leu Glu Gly
                165             170             175

Lys Ile Lys Glu Trp Tyr Glu Lys His Gly Asn Ser His Gln Gly Glu
            180             185             190

Pro Arg Asp Tyr Ser Lys Tyr Tyr Lys Thr Ile Asp Asp Leu Lys Asn
            195             200             205

Gln Ile Leu Asn Leu Thr Thr Asp Asn Ala Asn Ile Leu Leu Gln Ile
        210             215             220

Asp Asn Ala Arg Leu Ala Ala Asp Asp Phe Arg Leu Lys Tyr Glu Asn
225             230             235             240

Glu Val Ala Leu Arg Gln Ser Val Glu Ala Asp Ile Asn Gly Leu Arg
                245             250             255

Arg Val Leu Asp Glu Leu Thr Leu Thr Lys Ala Asp Leu Glu Met Gln
            260             265             270

Ile Glu Ser Leu Thr Glu Glu Leu Ala Tyr Leu Lys Lys Asn His Glu
        275             280             285

Glu Glu Met Lys Asp Leu Arg Asn Val Ser Thr Gly Asp Val Asn Val
290             295             300

Glu Met Asn Ala Ala Pro Gly Val Asp Leu Thr Gln Leu Leu Asn Asn
305             310             315             320

Met Arg Ser Gln Tyr Glu Gln Leu Ala Glu Gln Asn Arg Lys Asp Ala
            325             330             335

Glu Ala Trp Phe Asn Glu Lys Ser Lys Glu Leu Thr Thr Glu Ile Asp
            340             345             350

Asn Asn Ile Glu Gln Ile Ser Ser Tyr Lys Ser Glu Ile Thr Glu Leu
        355             360             365

Arg Arg Asn Val Gln Ala Leu Glu Ile Glu Leu Gln Ser Gln Leu Ala
370             375             380

Leu Lys Gln Ser Leu Glu Ala Ser Leu Ala Glu Thr Glu Gly Arg Tyr
385             390             395             400

Cys Val Gln Leu Ser Gln Ile Gln Ala Gln Ile Ser Ala Leu Glu Glu
            405             410             415

Gln Leu Gln Gln Ile Arg Ala Glu Thr Glu Cys Gln Asn Thr Glu Tyr
            420             425             430
```

-continued

```
Gln Gln Leu Leu Asp Ile Lys Ile Arg Leu Glu Asn Glu Ile Gln Thr
        435                 440                 445

Tyr Arg Ser Leu Leu Glu Gly Glu Gly Ser Ser Gly Gly Gly Gly Arg
450                 455                 460

Gly Gly Gly Ser Phe Gly Gly Tyr Gly Gly Ser Ser Gly Gly
465                 470                 475                 480

Gly Ser Ser Gly Gly Gly His Gly Gly His Gly Gly Ser Ser Gly
                485                 490                 495

Gly Gly Tyr Gly Gly Ser Ser Gly Gly Ser Ser Gly Gly
                500                 505                 510

Tyr Gly Gly Gly Ser Ser Gly Gly His Gly Gly Ser Ser Ser Gly
            515                 520                 525

Gly Tyr Gly Gly Ser Ser Gly Gly Gly Gly Gly Tyr Gly Gly
        530                 535                 540

Gly Ser Ser Gly Gly Gly Ser Ser Gly Gly Gly Tyr Gly Gly
545                 550                 555                 560

Ser Ser Ser Gly Gly His Lys Ser Ser Ser Gly Ser Val Gly Glu
                565                 570                 575

Ser Ser Ser Lys Gly Pro Arg Tyr
                580
```

<210> SEQ ID NO 31
<211> LENGTH: 214
<212> TYPE: PRT
<213> ORGANISM: Homo sapien

<400> SEQUENCE: 31

```
Met Glu Glu Glu Ile Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu
    210
```

<210> SEQ ID NO 32
<211> LENGTH: 553
<212> TYPE: PRT
<213> ORGANISM: Homo sapien

<400> SEQUENCE: 32

```
Met Leu Ser Val Arg Val Ala Ala Val Val Arg Ala Leu Pro Arg
1               5                   10                  15

Arg Ala Gly Leu Val Ser Arg Asn Ala Leu Gly Ser Ser Phe Ile Ala
                20                  25                  30

Ala Arg Asn Phe His Ala Ser Asn Thr His Leu Gln Lys Thr Gly Thr
            35                  40                  45

Ala Glu Met Ser Ser Ile Leu Glu Glu Arg Ile Leu Gly Ala Asp Thr
        50                  55                  60

Ser Val Asp Leu Glu Glu Thr Gly Arg Val Leu Ser Ile Gly Asp Gly
65                  70                  75                  80

Ile Ala Arg Val His Gly Leu Arg Asn Val Gln Ala Glu Glu Met Val
                85                  90                  95

Glu Phe Ser Ser Gly Leu Lys Gly Met Ser Leu Asn Leu Glu Pro Asp
            100                 105                 110

Asn Val Gly Val Val Val Phe Gly Asn Asp Lys Leu Ile Lys Glu Gly
        115                 120                 125

Asp Ile Val Lys Arg Thr Gly Ala Ile Val Asp Val Pro Val Gly Glu
    130                 135                 140

Glu Leu Leu Gly Arg Val Val Asp Ala Leu Gly Asn Ala Ile Asp Gly
145                 150                 155                 160

Lys Gly Pro Ile Gly Ser Lys Thr Arg Arg Val Gly Leu Lys Ala
                165                 170                 175

Pro Gly Ile Ile Pro Arg Ile Ser Val Arg Glu Pro Met Gln Thr Gly
            180                 185                 190

Ile Lys Ala Val Asp Ser Leu Val Pro Ile Gly Arg Gly Gln Arg Glu
        195                 200                 205

Leu Ile Ile Gly Asp Arg Gln Thr Gly Lys Thr Ser Ile Ala Ile Asp
    210                 215                 220

Thr Ile Ile Asn Gln Lys Arg Phe Asn Asp Gly Ser Asp Glu Lys Lys
225                 230                 235                 240

Lys Leu Tyr Cys Ile Tyr Val Ala Ile Gly Gln Lys Arg Ser Thr Val
                245                 250                 255

Ala Gln Leu Val Lys Arg Leu Thr Asp Ala Asp Ala Met Lys Tyr Thr
            260                 265                 270

Ile Val Val Ser Ala Thr Ala Ser Asp Ala Ala Pro Leu Gln Tyr Leu
        275                 280                 285

Ala Pro Tyr Ser Gly Cys Ser Met Gly Glu Tyr Phe Arg Asp Asn Gly
    290                 295                 300

Lys His Ala Leu Ile Ile Tyr Asp Asp Leu Ser Lys Gln Ala Val Ala
305                 310                 315                 320

Tyr Arg Gln Met Ser Leu Leu Leu Arg Arg Pro Pro Gly Arg Glu Ala
                325                 330                 335

Tyr Pro Gly Asp Val Phe Tyr Leu His Ser Arg Leu Leu Glu Arg Ala
            340                 345                 350

Ala Lys Met Asn Asp Ala Phe Gly Gly Gly Ser Leu Thr Ala Leu Pro
        355                 360                 365

Val Ile Glu Thr Gln Ala Gly Asp Val Ser Ala Tyr Ile Pro Thr Asn
```

|     |     |     |     |     |     |     |     |     |     |     |     |
|---|---|---|---|---|---|---|---|---|---|---|---|
|     |     | 370 |     |     | 375 |     |     |     | 380 |     |     |
| Val | Ile | Ser | Ile | Thr | Asp | Gly | Gln | Ile | Phe | Leu | Glu | Thr | Glu | Leu | Phe |
| 385 |     |     |     |     | 390 |     |     |     | 395 |     |     |     |     |     | 400 |
| Tyr | Lys | Gly | Ile | Arg | Pro | Ala | Ile | Asn | Val | Gly | Leu | Ser | Val | Ser | Arg |
|     |     |     |     | 405 |     |     |     |     | 410 |     |     |     |     | 415 |     |
| Val | Gly | Ser | Ala | Ala | Gln | Thr | Arg | Ala | Met | Lys | Gln | Val | Ala | Gly | Thr |
|     |     |     | 420 |     |     |     |     | 425 |     |     |     |     | 430 |     |     |
| Met | Lys | Leu | Glu | Leu | Ala | Gln | Tyr | Arg | Glu | Val | Ala | Ala | Phe | Ala | Gln |
|     |     | 435 |     |     |     |     | 440 |     |     |     |     | 445 |     |     |     |
| Phe | Gly | Ser | Asp | Leu | Asp | Ala | Ala | Thr | Gln | Gln | Leu | Leu | Ser | Arg | Gly |
|     |     | 450 |     |     |     |     | 455 |     |     |     |     | 460 |     |     |     |
| Val | Arg | Leu | Thr | Glu | Leu | Leu | Lys | Gln | Gly | Gln | Tyr | Ser | Pro | Met | Ala |
| 465 |     |     |     |     | 470 |     |     |     |     | 475 |     |     |     |     | 480 |
| Ile | Glu | Glu | Gln | Val | Ala | Val | Ile | Tyr | Ala | Gly | Val | Arg | Gly | Tyr | Leu |
|     |     |     |     | 485 |     |     |     |     | 490 |     |     |     |     | 495 |     |
| Asp | Lys | Leu | Glu | Pro | Ser | Lys | Ile | Thr | Lys | Phe | Glu | Asn | Ala | Phe | Leu |
|     |     |     | 500 |     |     |     |     | 505 |     |     |     |     | 510 |     |     |
| Ser | His | Val | Val | Ser | Gln | His | Gln | Ala | Leu | Leu | Gly | Thr | Ile | Arg | Ala |
|     |     | 515 |     |     |     |     | 520 |     |     |     |     | 525 |     |     |     |
| Asp | Gly | Lys | Ile | Ser | Glu | Gln | Ser | Asp | Ala | Lys | Leu | Lys | Glu | Ile | Val |
|     |     | 530 |     |     |     |     | 535 |     |     |     |     | 540 |     |     |     |
| Thr | Asn | Phe | Leu | Ala | Gly | Phe | Glu | Ala |
| 545 |     |     |     |     | 550 |     |     |     |